(12) United States Patent
Robin et al.

(10) Patent No.: US 7,285,546 B2
(45) Date of Patent: *Oct. 23, 2007

(54) CEPHALOTAXANES, THEIR METHOD OF PREPARATION AND THEIR USE IN TREATMENT OF CANCERS, LEUKEMIAS, PARASITES INCLUDING THOSE RESISTANT TO USUAL CHEMOTHERAPEUTIC AGENTS AND AS REVERSAL AGENTS

(75) Inventors: Jean-Pierre Robin, Charlottesville, VA (US); Robert Dhal, Pruille le Chetif (FR); Freddy Drouye, Le Genest (FR); Jean-Pierre Marie, Sevres (FR); Nina Radosevic, Charlottesville, VA (US); Julie Robin, Rouillon (FR); Karine Souchaud, Joue-les-Tours (FR); Patricia Bataille, Degre (FR)

(73) Assignee: Stragen Pharma S.A., Geneva (CH)

( * ) Notice: Subject to any disclaimer, the term of this patent is extended or adjusted under 35 U.S.C. 154(b) by 267 days.

This patent is subject to a terminal disclaimer.

(21) Appl. No.: 10/403,506

(22) Filed: Apr. 1, 2003

(65) Prior Publication Data

US 2004/0006064 A1 Jan. 8, 2004

Related U.S. Application Data

(63) Continuation-in-part of application No. 09/710,870, filed on Nov. 14, 2000, now Pat. No. 6,579,869.

(51) Int. Cl.
*A61P 35/02* (2006.01)
*A61P 33/00* (2006.01)
*A61K 31/55* (2006.01)
*C07D 223/00* (2006.01)
*C07D 487/00* (2006.01)

(52) U.S. Cl. .................. 514/214.01; 540/543; 540/581

(58) Field of Classification Search ........... 514/214.01; 540/543, 581
See application file for complete search history.

(56) References Cited

U.S. PATENT DOCUMENTS 6,579,869 B1 * 6/2003 Robin et al. ........... 514/214.01

FOREIGN PATENT DOCUMENTS

WO WO99/48894 A1 9/1999

OTHER PUBLICATIONS

Kano et al., In Vitro Cytotoxic Effects of a Tyrosine Kinase Inhibitor STI571 in Combination With Commonly Used Antileukemic Agents, Blood, vol. 97, No. 7, pp. 1999-2007, Apr. 1, 2001.*
O'Brien et al., Sequential Homoharringtonine and Interferon-.alpha. in the Treatment of Early Chronic Phase Chronic Myelogenous Leukemia, Blood, vol. 93, No. 12, pp. 4149-4153, Jun. 15, 1999.*
Medline abstract of Witte et al., A Phase II Trial of Homoharringtonine and Caracemide in the Treatment of Patients With Advanced Large Bowel Cancer, New Drugs, vol. 17, No. 2, pp. 173-177, 1999.*
Takano et al., Drupangtonine, A Novel Antileukemic Alkaloid From Cephalotaxus Harringtonia Var. Drupacea, Bioorganic & Medicinal Chemistry Letters, vol. 6, No. 14, pp. 1689-1690, 1996.*

(Continued)

*Primary Examiner*—Brenda Coleman
(74) *Attorney, Agent, or Firm*—Buchanan Ingersoll & Rooney PC

(57) ABSTRACT

The present invention concerns a compound of formula (I)

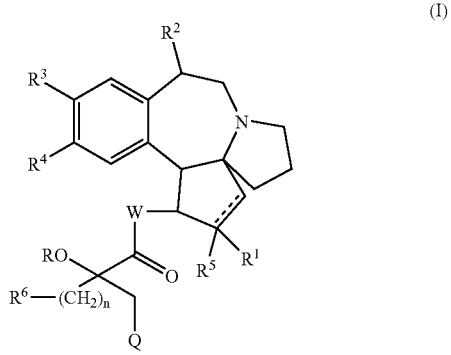

(I)

wherein:

W represents O or NH,

Q represents an unbranched or branched, saturated or unsaturated or aromatic, cyclic or acyclic or heterocyclic hydrocarbon radical containing 1 to 30 carbon atoms including or not heteroatom(s), $R^1$ is H, OH, or $R^1$, $R^2$ form together —O—, $R^3$=$R^4$=OMe or $R^3$ and $R^4$ form together —OCH$_2$O—, R is H, $C_1$-$C_{30}$alkyl or O-protecting group and $R^6$ represents an unbranched or branched, saturated or unsaturated or aromatic, cyclic or acyclic or heterocyclic hydrocarboned radical containing 1 to 30 carbon atoms including or not heteroatom(s), or R and $R^6$ form together —CMe$_2$-, n is 0 to 8, $R^5$ is H, OH, OMe, O—($C_1$-$C_{30}$)-alkyl, O-aryl-($C_1$-$C_{30}$)-alkyl, O—($C_2$-$C_{30}$)-alkenyl, O—($C_3$-$C_{30}$)-cycloalkyl or O-aryl, the dotted line is null or forms a double bond depending on the meaning of $R^1$.

It also concerns their methods of preparation and their use in treatment of cancers, leukemias, parasites and as reversal agents of harringtonines.

19 Claims, No Drawings

OTHER PUBLICATIONS

Kelly et al., Preparation of Harringtonine from Cephalotaxine, Journal of Organic Chemistry, vol. 44, No. 1, pp. 63-67, 1979.*

Jiachong Cheng et al, "Stereospecific synthesis of deoxyharringtonine and homoharringto-nine", Chemical Abstracts, Accession No. 103:160738, XP002163590, Abstract; Figure 313, & Yoaxue Xuebao (1984) 19(3), 178-83.

Hiroshi Morita et al, "Cephalezomines A-F, potent cytotoxic alkaloids from Cephalotaxus harringtonia var. nana", *Tetrahedron* (2000), 56(19), 2929-2934, XP004198001.

Ichiro Takano et al, "New Cephalotaxus Alkaloids from Cephalotaxus harringtonia var. drupacea", *J. Nat. Prod.* (1996), 59(10), 965-967, XP002163587.

Yongkeng Wang et al, "Synthesis of homoharringtonine and separation of its stereomers", Database accession No. 103:71569, XP002163591, Abstract; Figure 315 & Huaxue Xuebao (1985), 43(2), 161-7.

Sayoko Hiranuma et al, "Studies in Cephalotaxus Alkaloids, Stereospecific Total Synthesis of Homoharringtonine", *J. Org. Chem.* (1983), 48(26), 5321-6, XP002087582.

Puzhu Cong, "Mass spectroscopic study of cephalotaxine alkaloids", Chemical Abstracts, Database accession No. 99:54042, XP002163592, Abstract; Figure 318 & Yaoxue Xuebao (1983), 18(3), 215-226.

S. Hiranuma et al, "Synthesis of Hemoharringtonine and its Derivative by Partial Esterificaiton of Cephalotaxine", *Tetrahedron Lett.* (1982), 23(34), 3431-4, XP002163588.

Yulin Li et al, "New synthetic method for harringtonine", Chemical Abstracts, Database accession No. 98:16906, XP002163593, Abstract; Figure 324 & Lanzhou Daxue Xuebao, Ziran Kexueban (1982), 18(3), 126.

Shu-Wen Li et al, "A study on the deoxyharringtonine and its analogs", Chemical Abstracts, Database accession No. 85:108857, XP002163594, Abstract; Figure 328 & Hua Hsueh Hsueh Pao (1975), 33(1), 75-8.

K. L. Mikolajczak et al, "Partial synthesis of harringtonine analogs", *J. Pharm. Sci.*, (1974), 63(8), 1280-3, XP002163589.

PCT/IB 00/01593 International Search Report, date of mailing: Apr. 12, 2001.

CAPLUS Printout for Cheng et al., Stereospecific Synthesis of Deoxyharringtonine and Homoharringtonine, Yaoxue Xuebao, vol. 19, No. 3, pp. 178-183, 1984.

He et al., Stability-Indicating LC Assay of and Impurity Identification in Homoharringtonine Samples, Journal of Pharmaceutical and Biomedical Analysis, vol. 22, No. 3, pp. 541-544, 2000.

* cited by examiner

CEPHALOTAXANES, THEIR METHOD OF PREPARATION AND THEIR USE IN TREATMENT OF CANCERS, LEUKEMIAS, PARASITES INCLUDING THOSE RESISTANT TO USUAL CHEMOTHERAPEUTIC AGENTS AND AS REVERSAL AGENTS

This application is a continuation-in-part (CIP) of application Ser. No. 09/710,870, filed Nov. 14, 2000, now allowed now U.S. Pat. No. 6,579,969, the entire contents of which are herein incorporated by reference.

The present invention concerns new cephalotaxanes, their methods of preparation and their use in treatment of cancers, leukemias, parasites including those resistant to usual chemotherapeutic agents and as reversal agents of harringtonines.

Cephalotaxanes (CTX) are particular alkaloids today only extracted from the Cephalotaxaceae family exhibiting the structural formula (1).

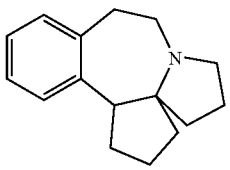

(1)

Several substituents may be encountered on this core: hydroxyl, ether, acyloxy etc. Some double bound or intramolecular bridge achieve to definite cephalotaxanes. Several dozen of cephalotaxanes have been isolated from various cephalotaxus species.

Cephalotaxoids include cephalotaxanes and unnatural analogs of cephalotaxanes.

Cephalotaxines 2 are cephalotaxanes without acyloxy side-chain.

Harringtonines (i.e. harringtonine=HA and homoharringtonine=HHT) are natural esters of cephalotaxines exhibiting generally a strong cytotoxic activity.

Harringtoids include harringtonines and unnatural analogs of harringtonines.

Two harringtonines are very promising drugs in the treatment of certain leukemia such as Chronic Myelogenous Leukemia (CML). Definite activity of HHT was observed in acute myelogenous leukemia (AML), acute promyelocytic leukemia (APL), and myelodysplastic syndrome (MDS) (Warrell Jr Rpet al, 3:617-621, 1985; Feldman E et al, Leukemia 6:1185-88,1992; Feldman E J et al, Leukemia 10:40-42,1996; Kantarjian H et al., Cancer 63:813-817, 1989; Kantarjian H et al., J Clin Oncol 18:3513-3521, 2000). The present applicants have initiated in France compassionate use of HHT in CML patients resistant or not eligible to all existing therapies and several phase II and III clinical trials including in patient with CML and AML are ongoing in France and in the U.S. However, it should be pointed out that harringtonines pertain to the series of natural drugs exhibiting the multiresistance phenomenon which led to relapse of the cancer diseases. This situation is a serious limitation to the use of natural chemotherapeutic agents in the treatment of cancers and leukemia.

Harringtonine inhibit protein synthesis at the level of elongation; however, the ultimate mechanism of action of harringtonines remain unknown. The final result is the self-destruct of the cell. Clinically, harringtonines have a selective action in leukemia of the myeloid series. In addition, harringtonines interact with P Glycoprotein (PGP) and Multiresistance Protein (MRP). PGP, MRP and other efflux pumps are complex molecular entities which are ubiquitous in nature. Their role is to selectively efflux the environmental natural toxic agents, including agents of chemotherapy (anthracyclines, taxanes, epipodophyllotoxins, harringtonine, etc.) It was pointed out that no common structural feature of this natural cytotoxic may be related to molecular recognizing by PGP.

A number of analogs all less active than harringtonines have been synthesized. The more active among these esters are about one magnitude less cytotoxic than harringtonines in vitro (i.e. HA, HHT neoharringtonine, have an activity=$IC_{50}$ ranged from 10 to 30 ng per mL, whereas analogs previously synthesized have an $IC_{50}$ higher than 100 ng/mL). No relation structure activity relationship had been previously found since the discovery of harringtonines.

Therefore, there is a need for new analogs of harringtonines having the same magnitude of cytotoxicity as harringtonines in vitro.

Surprisingly, the present applicant have synthesized a series of CTX analogs exhibiting stronger in vitro inhibition of leukemic cell lines such as K562, than HHT used as reference.

The present invention provides cephalotaxanes having formula (I)

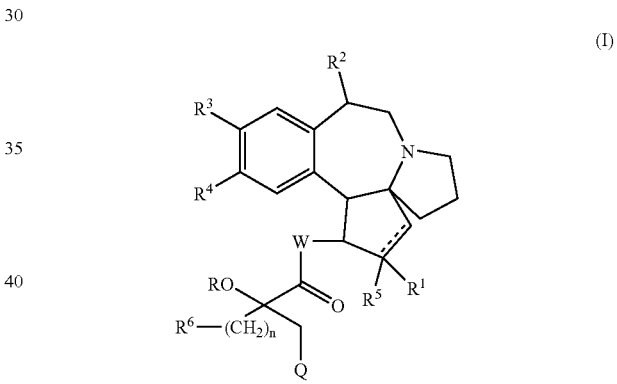

(I)

wherein

W represents O or NH

Q represents an unbranched or branched, saturated or unsaturated or aromatic, cyclic or acyclic or heterocyclic hydrocarboned radical containing 1 to 30 carbon atoms including or not heteroatom(s), $R^1$ is H, OH, OMe, O—($C_1$-$C_{30}$)alkyl, O-aryl($C_1$-$C_{30}$)alkyl, O—($C_2$-$C_{30}$)alkenyl, O—($C_3$-$C_{30}$)cycloalkyl or null and $R^2$ is H or OH, or $R^1$, $R^2$ form together —O—, $R^3$=$R^4$=OMe or $R^3$ and $R^4$ form together —OCH$_2$O—, R is H, $C_1$-$C_{30}$ alkyl or O-protecting group and $R^6$ represents an unbranched or branched, saturated or unsaturated or aromatic, cyclic or acyclic or heterocyclic hydrocarboned radical containing 1 to 30 carbon atoms including or not heteroatom(s), or R and $R^6$ form together —CMe$_2$-, n is 0 to 8, $R^5$ is H, OH, OMe, O—($C_1$-$C_{30}$)alkyl, O-aryl($C_1$-$C_{30}$)alkyl, O—($C_2$-$C_{30}$))alkenyl, O—($C_3$-$C_{30}$)cycloalkyl or O-aryl, the dotted line is null or forms a double bond depending on the meaning of $R^1$, except for compounds where W represents O, the dotted line forms a double bond, $R^1$ is null, $R^2$ is H, $R^3$ and $R^4$ represent —O—CH$_2$—O—, $R^5$ is OMe, Q=CO$_2$R$^7$ and 1°) R=H, $R^6$=—(C—OH)Me$_2$, n=2 or 3, $R^7$ Me or H, 2°) R=H, $R^6$=—(C—H)Me$_2$, n=2 to 4, $R^7$=Me, 3°) R=H, $R^6$=—(C—H)Me$_2$, n 1 or 2, $R^7$=H, 4°) R=H, $R^6$=Ph, n1 to 3, $R^7$=Me, 5°) R=H, $R^6$=—CH=CH-Ph, n=0, $R^7$=Me, 6°) R=H, $R^6$=CH$_3$, n=4, $R^7$=Me, 7°) R and $R^6$ form together —CMe$_2$-, n=2 or 3, $R^7$=Me, W represents O, the dotted line forms a double bond, $R^1$ is null, $R^2$ is OH, $R^3$ and $R^4$ represent —O—CH$_2$—O—, $R^5$ is OMe and R=H, $R^6$=—(C—H)Me$_2$, n=2 or 3, $R^7$=Me W represents O, the dotted line is null, $R^1$ and $R^2$ represent —O—, $R^3$ and $R^4$ represent —O—CH$_2$—O—, $R^5$ is OMe and R=H, $R^6$=—(C—H)Me$_2$, n=2, $R^7$=Me.

The term "O-Protecting group" as used in the present invention refers to a substituent which protects hydroxyl groups against undesirable reactions during synthetic procedures such as those O-protecting groups disclosed in Greene, "Protective Groups In Organic synthesis", (John Wiley & Sons, New York (1981)). O-protecting groups comprise substituted methyl ethers, for example, methoxymethyl, benzyloxymethyl, 2-methoxyethoxymethyl, 2-(trimethylsilyl)ethoxymethyl, t-butyl, benzyl and triphenylmethyl, tetrahydropyranyl ethers, substituted ethyl ethers, for example, 2,2,2-trichloroethyl, silyl ethers, for example, trimethylsilyl, t-butyldimethylsilyl and t-butyidiphenylsilyl; and esters prepared by reacting the hydroxyl group with a carboxylic acid for example, acetate, propionate, benzoate and the like.

The term "$C_1$-$C_{30}$alkyl" as used in the present invention refers to straight or branched chain substituted or unsubstituted alkyl radicals containing from 1 to 30 carbon atoms including, but not limited to, methyl, ethyl, n-propyl, iso-propyl, n-butyl, iso-butyl, sec-butyl, t-butyl, n-pentyl, n-hexyl and the like.

The term "$C_2$-$C_{30}$alkenyl" as used in the present invention refers to straight or branched chain substituted or unsubstituted alkenyl radicals containing from 1 to 30 carbon atoms including, but not limited to, ethenyl, propenyl, butenyi, pentenyl, hexenyl and the like.

The term "aryl" as used in the present invention refers to a monocyclic or bicyclic carbocyclic ring system having one or more aromatic rings including, but not limited to, pheny, naphthyl, tetrahydronaphthyl, indanyl and the like. Aryl groups can be unsubstituted or substituted with one or more substituents.

The term "aryl($C_1$-$C_{30}$)alkyl" as used in the present invention refers to an aryl group such as defined above appended to a $C_1$-$C_{30}$alkyl radical such as defined above, for example, benzyl and the like.

The term "$C_3$-$C_{30}$cycloalkyl" as used herein refers to a carbocyclic ring having 3 to 30 carbon atoms including, but not limited to, cyclopropyl, cyclopentyl, cyclohexyl and the like. Cycloalkyl groups can be unsubstituted or substituted with one or more substituents.

An advantageous embodiment provides compounds of formula (I) wherein
Q=COZ-$R^8$,
Z=O, S, or NH, and

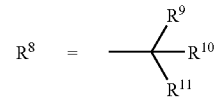

or Z—$R^8$ is NR$^{12}$R$^{13}$, $R^{12}$ and $R^{13}$ representing respectively $R^9$ and $R^{10}$, $R^9$, $R^{10}$, $R^{11}$ are independently H, deuterium, unbranched or branched $C_1$-$C_{30}$-alkyl, optionally containing one heteroatom, and optionally being substituted at the end of a hydrocarbonated chain by a hydroxy or alkoxy group, $C_3$-$C_{30}$-cycloalkyl, aryl, aryl-($C_1$-$C_{30}$)-alkyl, where aryl or the aryl fragment is a mono- or poly-cyclic group, optionally containing one heteroatom selected from O, S or N, and optionally being substituted by a halogen atom, a methoxy group or a nitro group, $C_2$-$C_{30}$-alkenyl, $C_2$-$C_{30}$-alkynyl, $C_1$-$C_{30}$-trihalogenoalkyl, $C_1$-$C_{30}$-alkylamino-($C_1$-$C_{30}$)-alkyl, $C_1$-$C_{30}$-dialkylamino($C_1$-$C_{30}$)-alkyl, or amino-($C_1$-$C_{30}$)-alkyl, or

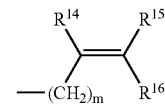

where $R^{14}$, $R^{15}$, $R^{16}$ are independently H, halogen, $C_1$-$C_{30}$-alkyl, $C_3$-$C_{30}$-cycloalkyl, aryl, aryl-($C_1$-$C_{30}$)-alkyl, $C_2$-$C_{30}$-alkenyl or $C_2$-$C_{30}$-alkynyl, $C_1$-$C_{30}$-trihalogenoalkyl, m=0 to 4, each of these groups optionally comprising heteroatom(s), such as in particular S, N or O.

The term "$C_2$-$C_{30}$alkynyl" as used in the present invention refers to straight or branched chain substituted or unsubstituted alkynyl radicals containing from 1 to 30 carbon atoms including, but not limited to, ethynyl, propynyl, butynyl, pentynyl, hexynyl, heptynyl and the like.

The term "$C_1$-$C_{30}$trihalogenoalkyl" as used in the present invention refers to straight or branched chain alkyl radicals containing from 1 to 30 carbon atoms substituted by three halogen atoms.

The term "$C_1$-$C_{30}$alkylamino" as used in the present invention refers to $R^{18}$NH— wherein $R^{18}$ is a $C_1$-$C_{30}$alkyl group such as defined above.

The term "$C_1$-$C_{30}$dialkylamino" as used herein refers to $R^{19}R^{20}$N— wherein $R^{19}$ and $R^{20}$ are independently selected from $C_1$-$C_{30}$alkyl such as defined above.

The term "$C_1$-$C_{30}$aminoalkyl" as used herein refers to a $C_1$-$C_{30}$alkyl radical such as defined above to which is appended an amino group (—NH$_2$).

The term "$C_1$-$C_{30}$alkylamino-($C_1$-$C_{30}$)-alkyl" as used herein, refers to a $C_1$-$C_{30}$alkyl radical such as defined above to which is appended an $C_1$-$C_{30}$alkylamino group such as defined above.

The term "$C_1$-$C_{30}$dialkylamino-($C_1$-$C_{30}$)-alkyl" as used herein refers to a $C_1$-$C_{30}$alkyl radical such as defined above to which is appended an $C_1$-$C_{30}$dialkylamino group such as defined above.

Another advantageous embodiment provides compounds of formula (I) wherein $R^6$=—(C—Y)Me$_2$, —CH=CMe$_2$, or an aryl group or R and $R^6$ form together —C Me$_2$-, Y=H, OH or halogen.

A further advantageous embodiment provides compounds of formula (I) wherein.

the dotted line forms a double bond $R^1$ is null $R^2$ is H $R^3$ and $R^4$ represent —O—CH$_2$—O—

$R^5$ is OMe.

A further aspect of the invention provides compounds of formula (I) wherein:

the dotted line is null $R^1$ and $R^2$ represent —O—

$R^3$ and $R^4$ represent —O—CH$_2$—O—

$R^5$ is OMe.

Yet, a further preferred embodiment provides compounds of formula (I) wherein n=1 or 3.

Another further aspect of the invention provides compounds of formula (I) wherein W represents O.

Advantageously, a compound according to the present invention is selected from the group consisting of the following compounds 1 to 90:

1

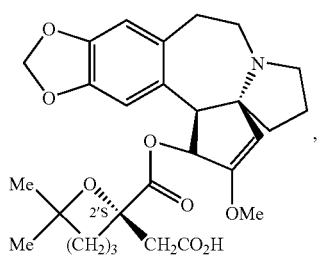

2

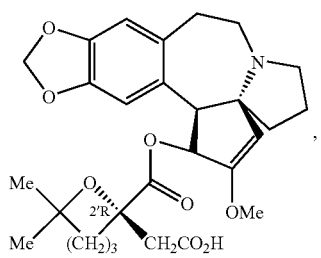

3

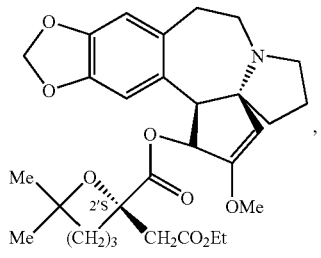

-continued

4

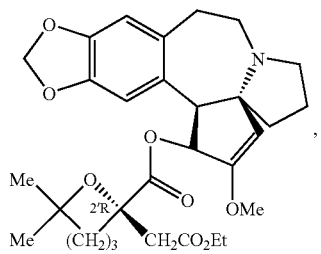

5

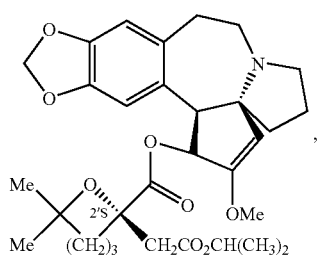

6

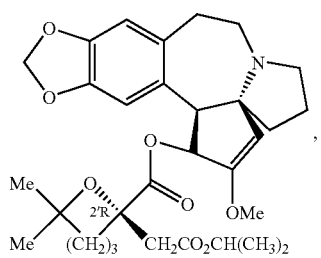

7

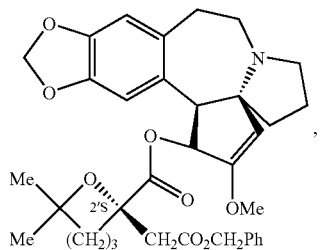

8

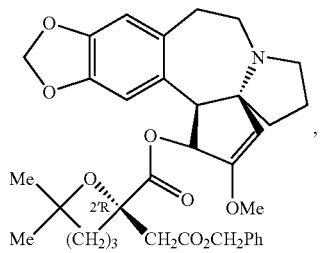

9

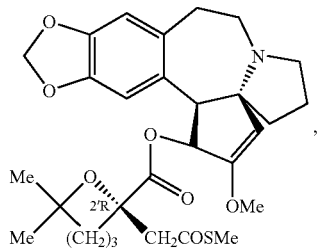

-continued
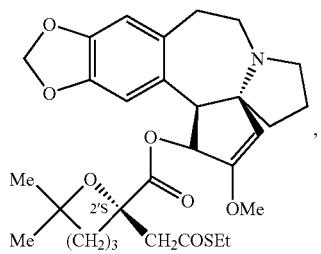
10
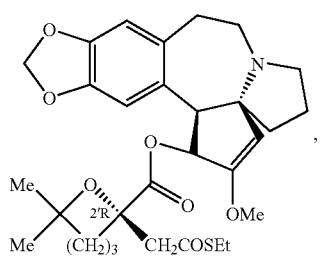
11
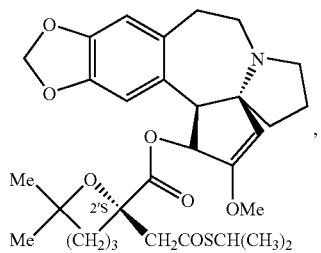
12
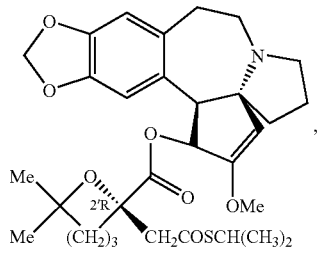
13
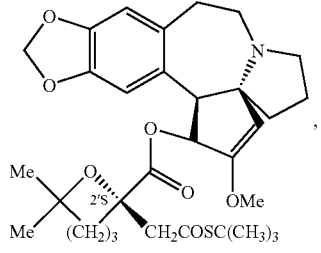
14
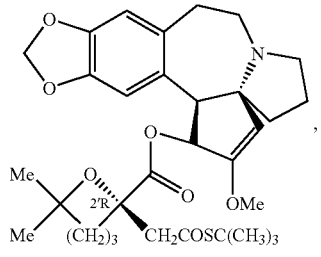
15
-continued
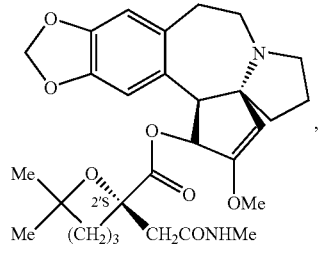
16
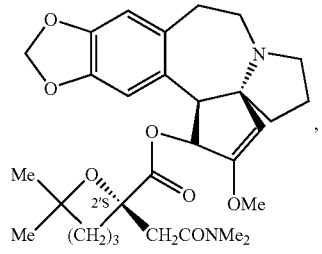
17
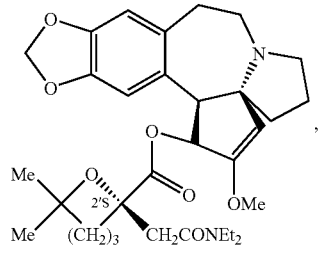
18
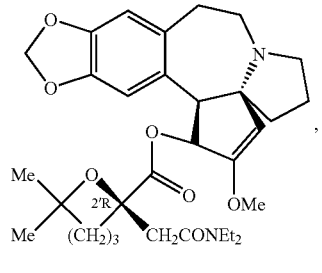
19
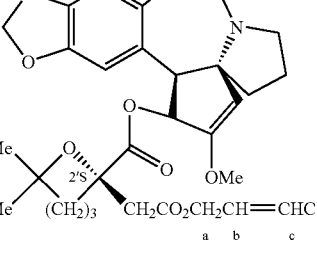
20
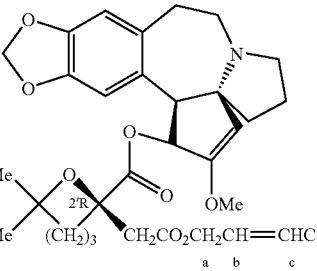
21

-continued
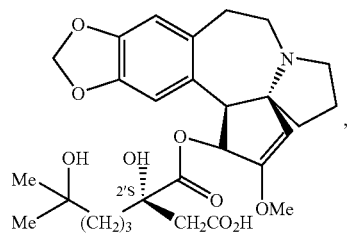
22
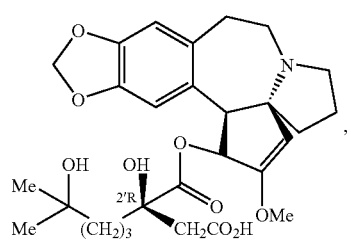
23
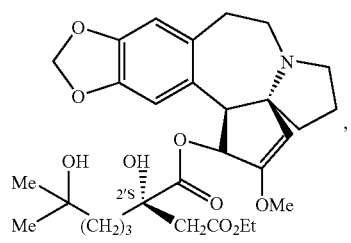
24
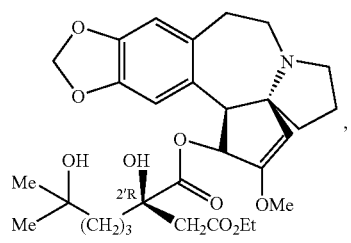
25
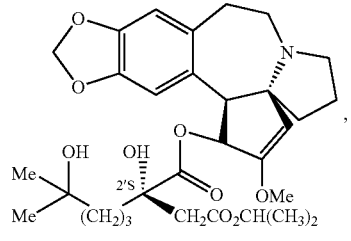
26
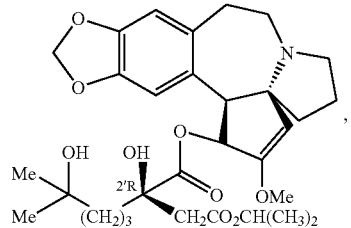
27
-continued
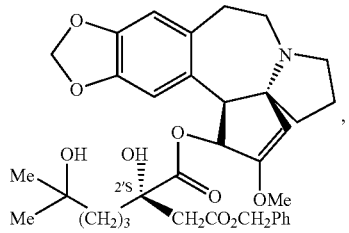
28
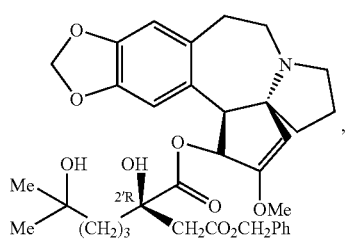
29
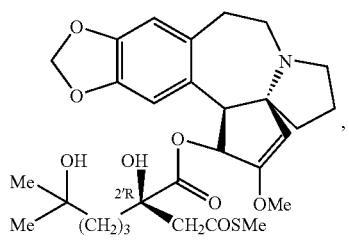
30
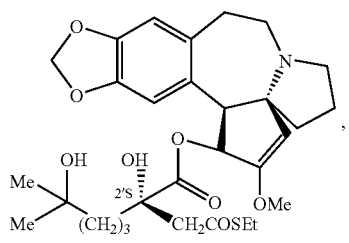
31
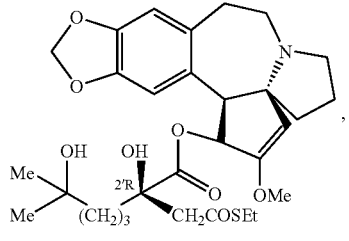
32
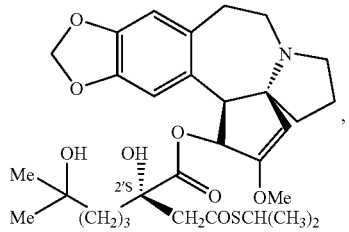
33

34
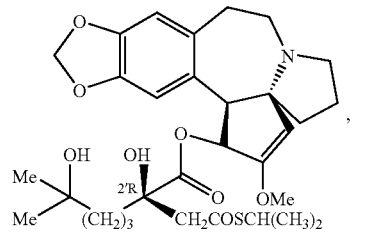
35
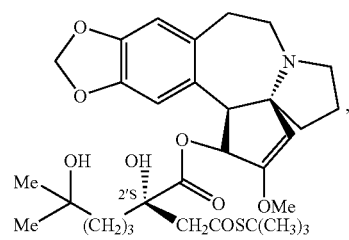
36
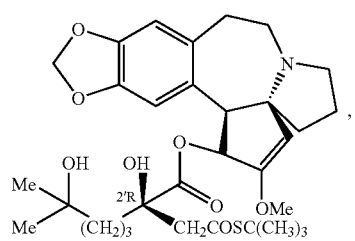
37
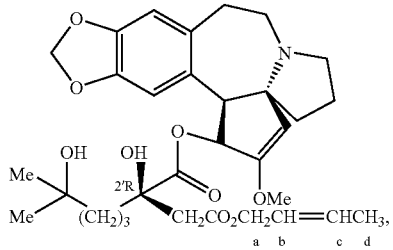
38
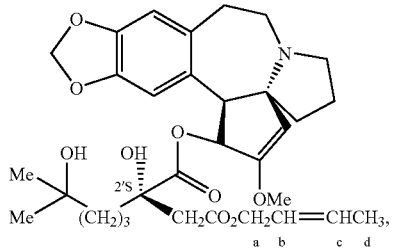
39
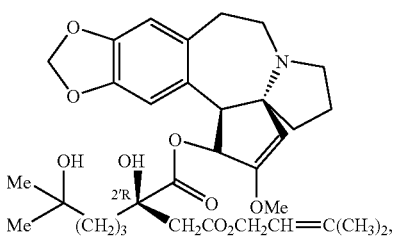
40
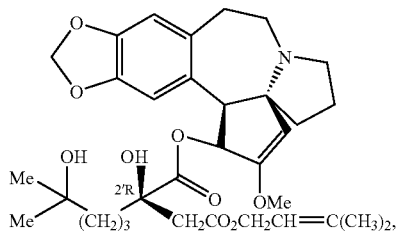
41
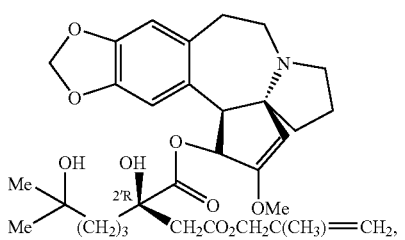
42
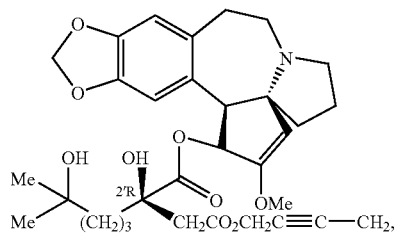
43
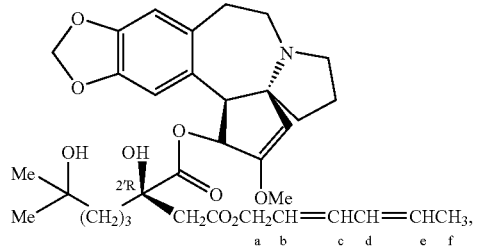
44
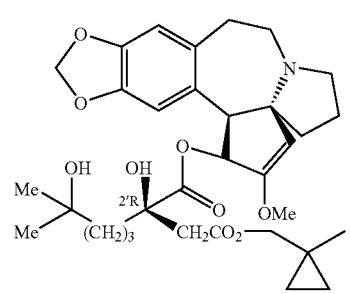
45
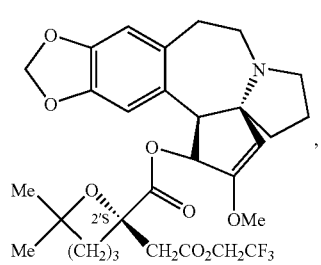

46
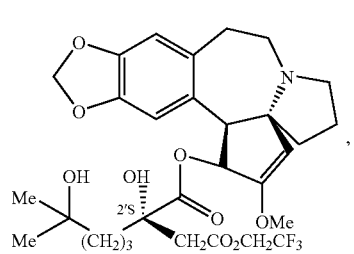
47
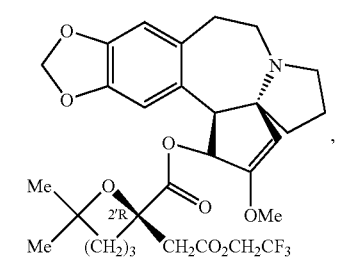
48
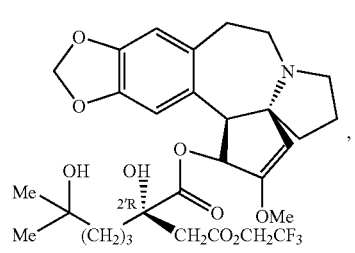
49
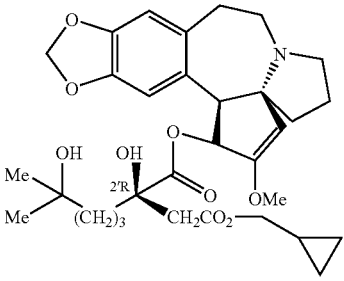
50
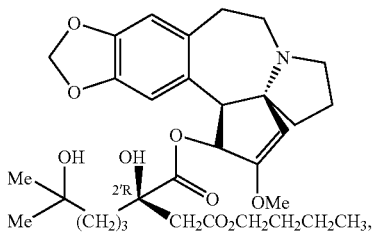
51
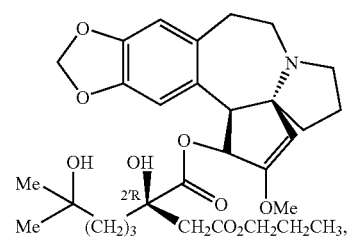
52
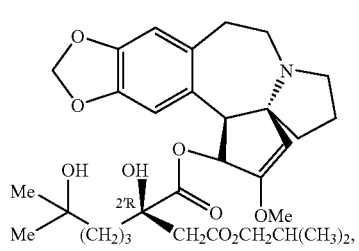
53
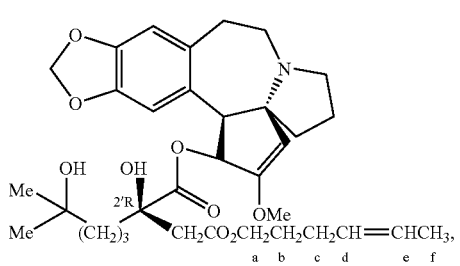
54
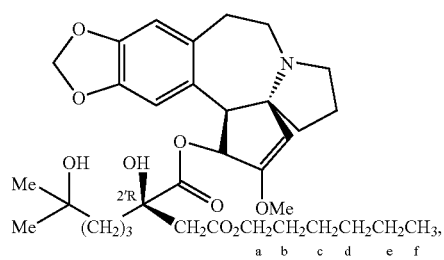
55
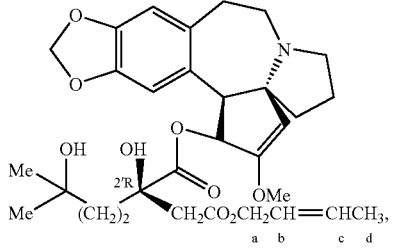
56
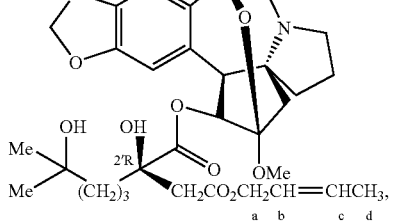
57
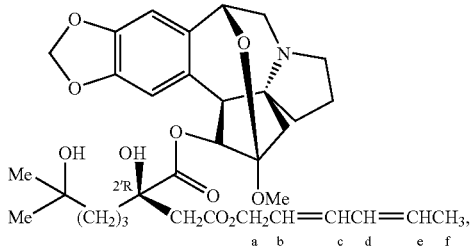

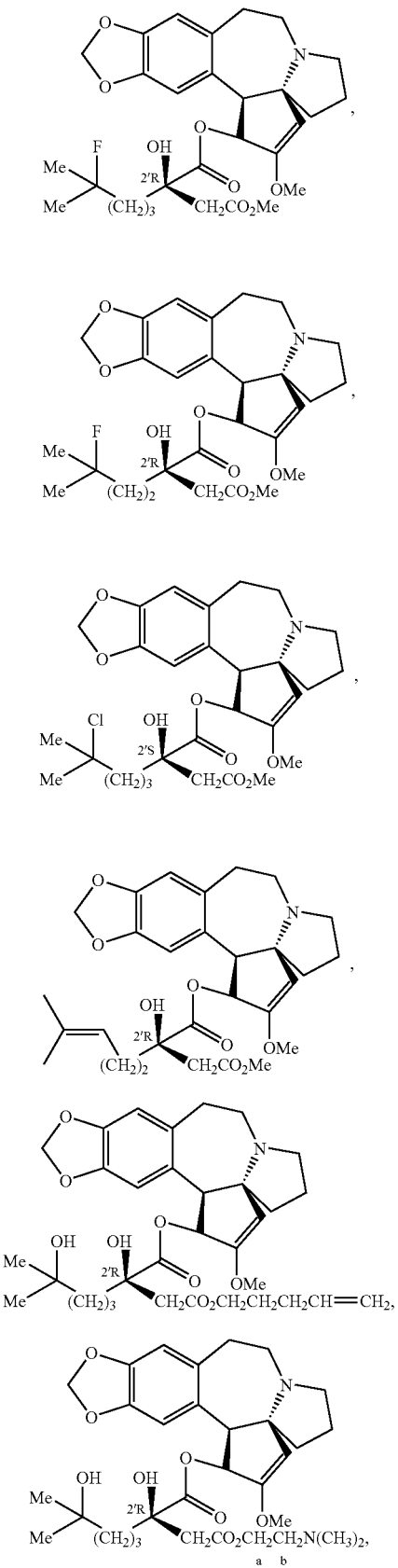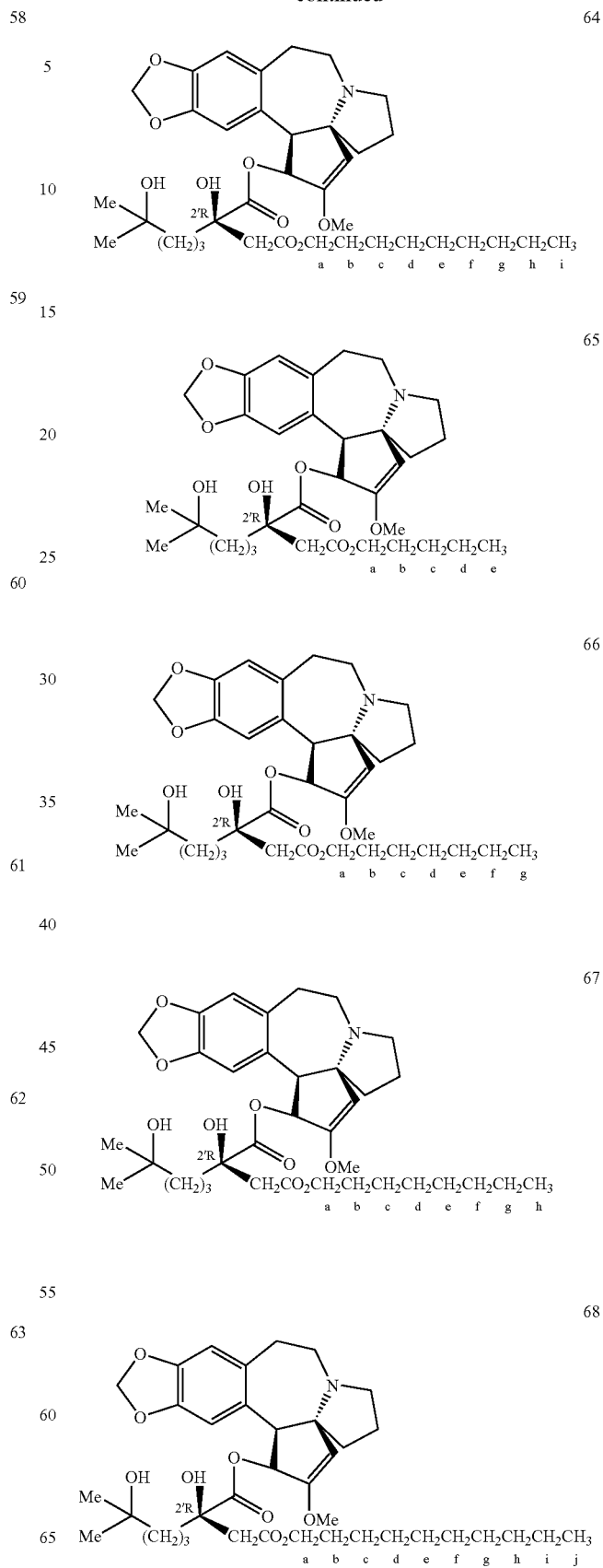

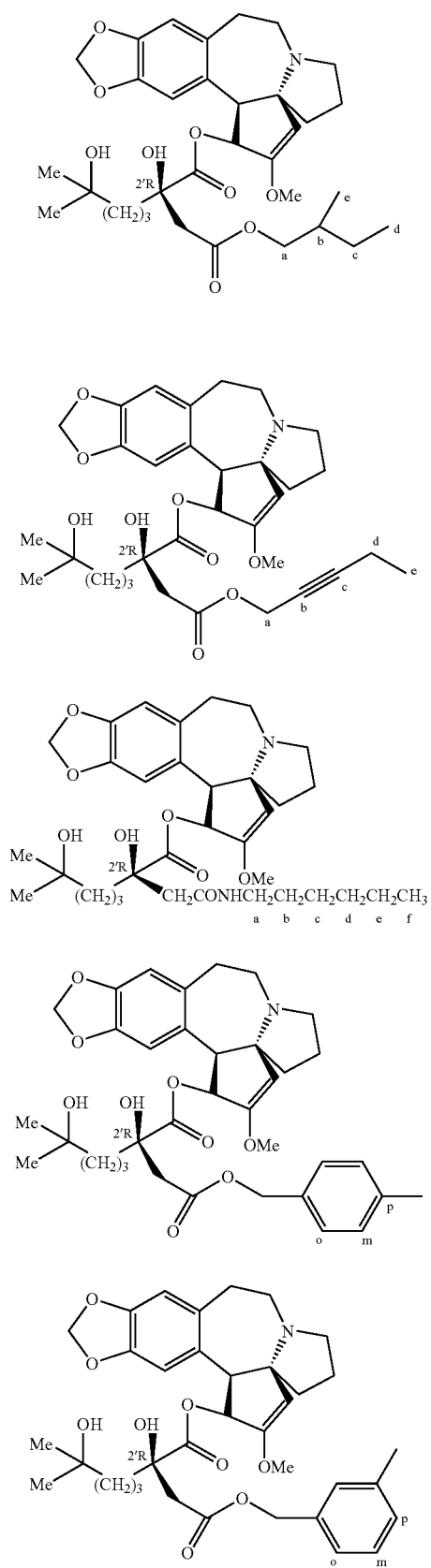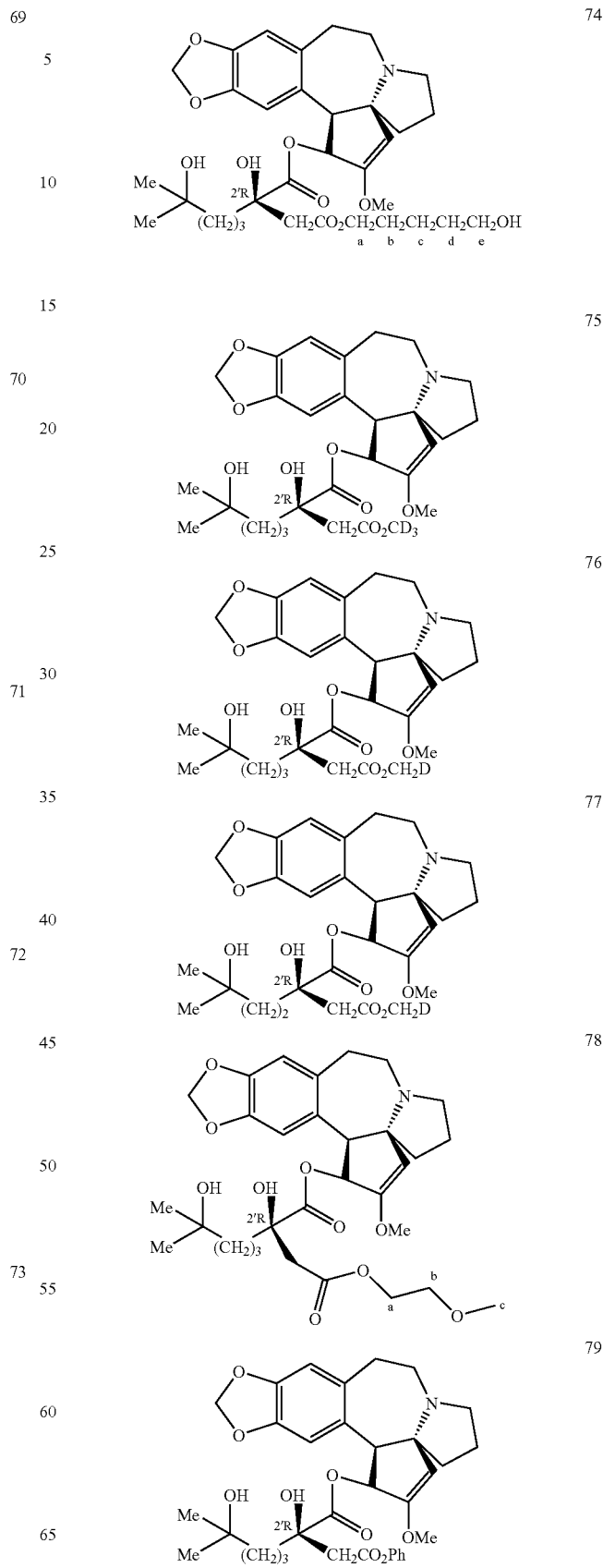

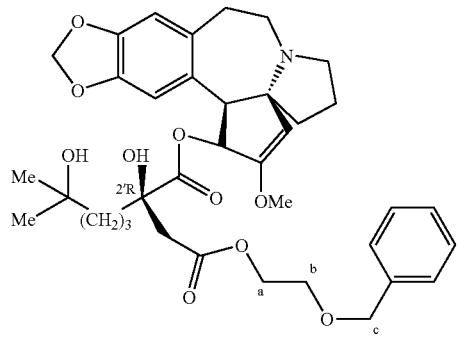
80
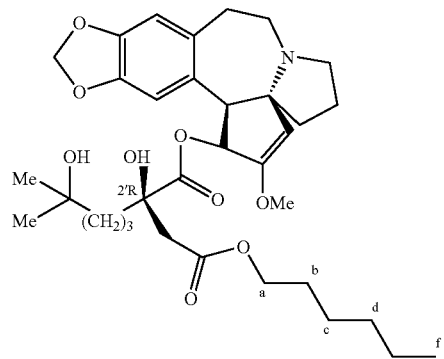
84
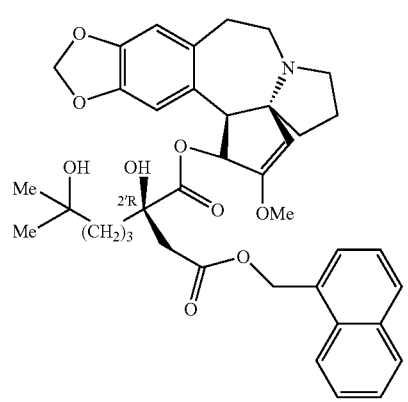
81
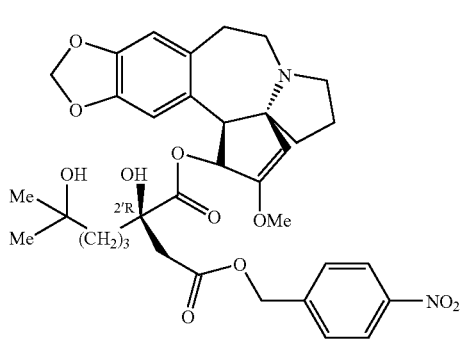
85
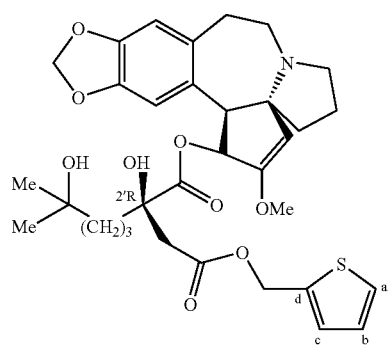
82
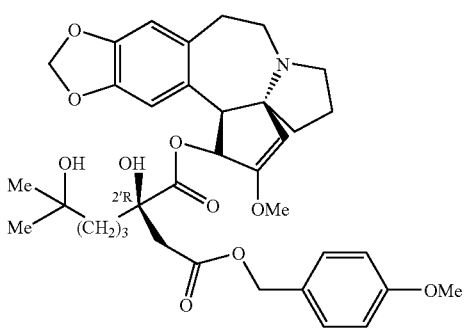
86
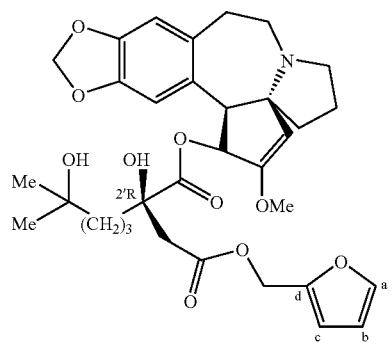
83
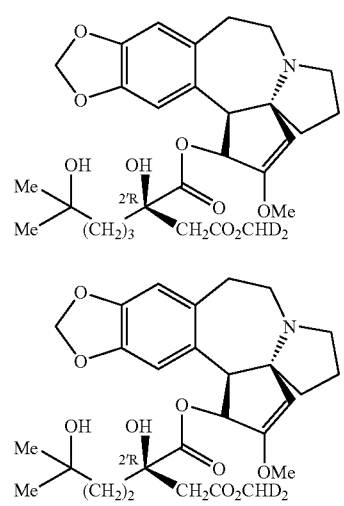
87
88

-continued

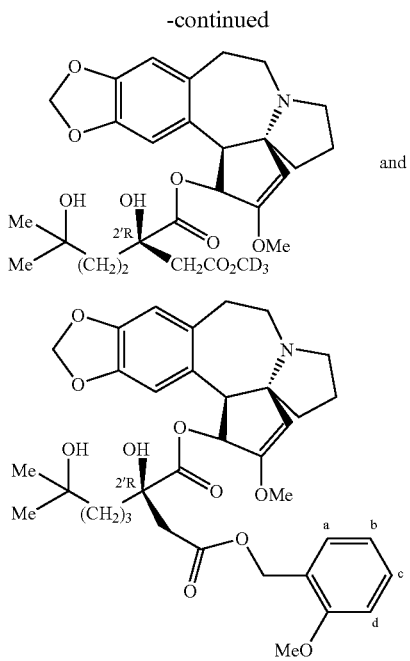

Advantageous compounds of the present invention include those according to formula (I) wherein Q represents COZR$^8$, Z is such as described above and R$^8$ has 6 carbon atoms without any hydrophilic group.

Some of the compounds described herein contain one or more centers of asymmetry and may thus give rise to diastereoisomers and optical isomers. The present invention is meant to comprehend such possible isomers or diastereoisomers alone or in a mixture, such as for example their racemic mixture.

Some of the compounds described herein contain olefinic double bonds and are meant to include both E and Z geometric isomers.

Another aspect of the invention is a process for preparing a compound of formula (I).

A. In the case where W represents NH, it comprises the following steps A1 to A2:

A1: reacting cephalotaxines of formula V:

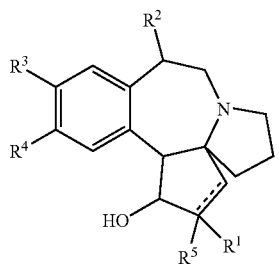

wherein
R$^1$ is H, OH, OMe, O—(C$_1$-C$_{30}$)alkyl, O-aryl(C$_1$-C$_{30}$)alkyl, O—(C$_2$-C$_{30}$)alkenyl, O—(C$_3$-C$_{30}$)cycloalkyl or null and R$^2$ is H or OH, or R$^1$, R$^2$ form together —O—,
R$^3$=R$^4$=OMe or R$^3$ and R$^4$ form together —OCH$_2$O—,
R$^5$ is H, OH, OMe, O—(C$_1$-C$_{30}$)alkyl, O-aryl(C$_1$-C$_{30}$)alkyl, O—(C$_2$-C$_{30}$)alkenyl, O—(C$_3$-C$_{30}$)cycloalkyl or O-aryl,
the doted line is null or forms a double bond depending on the meaning of R$^1$
by methods known by the one skilled in the art to obtain the compounds of formula VI

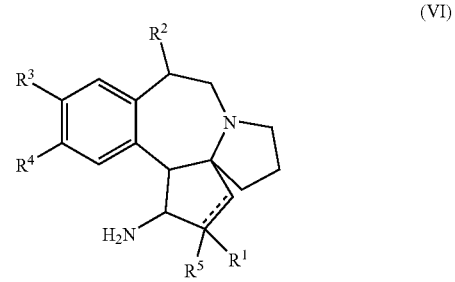

wherein
R$^1$ is H, OH, OMe, O—(C$_1$-C$_{30}$)alkyl, O-aryl(C$_1$-C$_{30}$)alkyl, O—(C$_2$-C$_{30}$)alkenyl, O—(C$_3$-C$_{30}$)cycloalkyl or null and R$^2$ is H or OH, or R$^1$, R$^2$ form together —O—,
R$^3$=R$^4$=OMe or R$^3$ and R$^4$ form together —OCH$_2$O—,
R$^5$ is H, OH, OMe, O—(C$_1$-C$_{30}$)alkyl, O-aryl(C$_1$-C$_{30}$)alkyl, O—(C$_2$-C$_{30}$)alkenyl, O—(C$_3$-C$_{30}$)cycloalkyl or O-aryl,
the doted line is null or forms a double bond depending on the meaning of R$^1$ For example, such methods are the following:
substituting the hydroxyl group of the cephalotaxines of formula V by an halogen or a tosylate by methods known by the one skilled in the art (such as by using SOCl$_2$), then substituting the halogen or the tosylate by the group NH$_2$ by methods known by the one skilled in the art (such as 1) the use of gaseous ammoniac in methylene chloride at 0° C. and 1 atm or 2) the use of NaN$_3$ in DMF followed by 2$_1$) a catalytic hydogenolysis with for example Pd/C as the catalyst or 2$_2$) the use of LiAlH$_4$) to obtain the compounds of formula VI.

A2: reacting the compounds of formula VI by the methods disclosed in WO 99/48894.

B. In the case where W represents O, Q=COR$^8$ and R$^8$ is such as described above, it comprises the step of reacting harringtonines or homoharringtonines commercially available (by SIGMA) with organometallic compounds, advantageously organolithium or grignard reagent.

C. In the case where W represents O, Q=CH$_2$ZR$^8$ or CH$^2$R$^8$ and Z and R$^8$ are such as described above, it comprises the step of reducing harringtonines or homoharringtonines commercially available (by SIGMA) with an hydride, advantageously boron or aluminium hydride D. In the case where W represents O, Q=COZ-R$^8$ and Z and R$^8$ are such as described above, it comprises the following steps i) then ii),
  i) hydrolyzing selectively the compound of formula (IV) which is available commercially

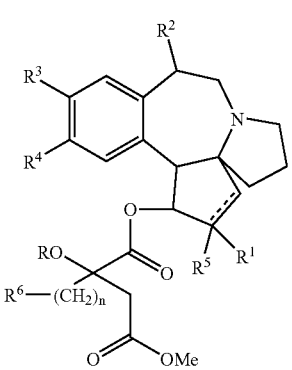

wherein
$R^1$ is H, OH, OMe, O—$(C_1$-$C_{30})$-alkyl, O-aryl —$(C_1$-$C_{30})$-alkyl, O—$(C_2$-$C_{30})$-alkenyl, O—$(C_3$-$C_{30})$-cycloalkyl or null and $R^2$ is H or OH, or $R^1$ and $R^2$ form together —O—
$R^3$=$R^4$=OMe or $R^3$ and $R^4$ form together —OCH$_2$O—
R is H, $C_1$-$C_{30}$alkyl or O-protecting group and $R^6$ represents an unbranched or branched, saturated or unsaturated or aromatic, cyclic or acyclic or heterocyclic hydrocarboned radical containing 1 to 30 carbon atoms, including or not heteroatom(s), or R and $R^6$ form together —CMe$_2$—;
n is 0 to 8.
$R^5$ is H, OH, OMe, O—$(C_1$-$C_{30})$-alkyl, O-aryl-$(C_1$-$C_{30})$-alkyl, O—$(C_2$-$C_{30})$-alkenyl, O—$(C_3$-$C_{30})$-cycloalkyl or O-aryl.
the doted line is null or forms a double bond depending on the meaning of $R^1$, with an agent such as mineral hydroxide, advantageously lithium, potassium or sodium hydroxide, in hydro-organic solvent mixture to give as reaction product, amphoteric acid of formula (III)

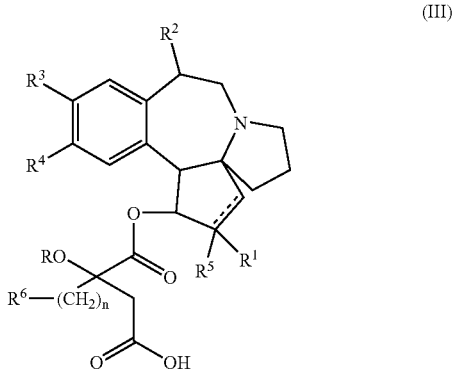

(III)

wherein $R^1$ to $R^5$, R and $R^6$ are defined as above,
ii) performing the esterification of the above obtained amphoteric acid of formula (III) with an esterification agent and a compound of formula $R^8$-ZH; $R^8$ and Z being defined as above and wherein the steps i) and ii) are carried out successively or simultaneously.

Advantageously the compounds of the following formula (II):

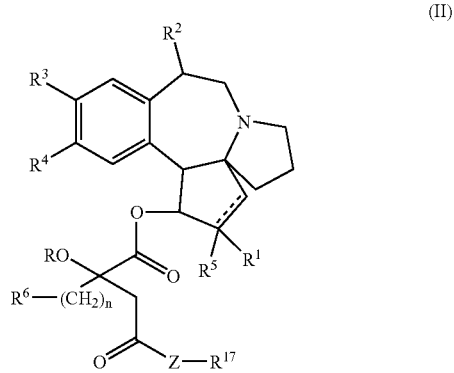

(II)

wherein
$R^1$ is H, OH, OMe, O—$(C_1$-$C_{30})$-alkyl, O-aryl —$(C_1$-$C_{30})$-alkyl, O—$(C_2$-$C_{30})$-alkenyl, O—$(C_3$-$C_{30})$-cycloalkyl or null and $R^2$ is H or OH, or $R^1$ and $R^2$ form together —O—

$R^3$=$R^4$=OMe or $R^3$ and $R^4$ form together —OCH$_2$O—
R is H, $C_1$-$C_{30}$alkyl or O-protecting group and $R^6$ represents an unbranched or branched, saturated or unsaturated or aromatic, cyclic or acyclic or heterocyclic hydrocarboned radical containing 1 to 30 carbon atoms, including or not heteroatom(s), or R and $R^6$ form together —CMe$_2$—
n is 0 to 8.
$R^5$ is H, OH, OMe, O—$(C_1$-$C_{30})$-alkyl, O-aryl-$(C_1$-$C_{30})$-alkyl, O—$(C_2$-$C_{30})$-alkenyl, O—$(C_3$-$C_{30})$-cycloalkyl or O-aryl.
the doted line is null or forms a double bond depending on the meaning of $R^1$,
Z=O or S, and
$R^{17}$ represents $C_1$-$C_{30}$alkyl, $C_2$-$C_{30}$alkenyl, $C_3$-$C_{30}$cycloalkyl, $C_2$-$C_{30}$alkynyl, aryl-$(C_1$-$C_{30})$-alkyl or aryl and advantageously methyl or ethyl, can also be used instead of the compounds of formula IV to prepare, according to the process A, the product of formula (I).

Advantageously, the esterification agent in process A is a lewis acid or a protonic acid.

In an advantageous embodiment of the process A according to the present invention, the amphoteric acid of formula (III) is activated with an imide or by formation of a mixte anhydride or an acid chloride.

Advantageously, the imide is dicyclohexylcarbodiimide or diisopropylcarbodiimide.

More advantageously the mixte anhydride is formed with 2,4,6-trichlorobenzoic acid by contact with 2,4,6-trichlorobenzoyl chloride in the presence of a base.

In another advantageous embodiment of the process A according to the. present invention, the steps i) and ii) are carried out simultaneously, without isolation of the amphoteric acid of formula (III), via a reaction of transesterification performed in presence of an acidic or basic catalyst.

Advantageously, the catalyst is a base, such as an alkaline hydride.

More advantageously, the catalyst is a lewis acid or a protonic acid.

Given their pharmacological properties, the compounds of the present invention may be used in human therapy in the treatment of cancer pathology.

This invention includes also a pharmaceutical composition which comprises a therapeutically effective amount of at least one compound according to the present invention with one or more pharmaceutically acceptable carriers, excipients or diluents.

These pharmaceutical compositions may be formulated for oral, intravenous or subcutaneous administration.

Another aspect of the invention is the use of at least one compound according to the present invention or of the pharmaceutical composition as described above as (i) chemotherapeutic agent, (ii) enhancer of other chemotherapeutic agents (iii) for inhibiting tumors growth, (iv) for inhibiting mammalian parasites.

Yet, another aspect of the invention is the use of at least one compound according to the present invention for the preparation of a pharmaceutical composition as (i) chemotherapeutic agent, (ii) enhancer of other chemotherapeutic agents (iii) for inhibiting tumors growth, (iv) for inhibiting mammalian parasites, or (v) as reversal agents in particular of harringtonines (a reversal agent is an agent able to reverse the cell multiresistance phenomenon).

Finally, the present invention describes a method for treating mammalian tumors which comprises administering to a mammal a therapeutically effective amount of at least one compound according to the present invention.

Another advantages of the compounds according to the present invention, is its activity on leukemic cell lines exhibiting resistance to other agents including harringtonines.

The following examples, which are given without implied limitation, illustrates the present invention.

EXAMPLE 1

Preparation of (−)-cephalotaxyl (2′S)-2-carboxymethyl-6,6-dimethyl-2-tetrahydropyranecarboxylate or 4′-demethyl-anhydro-epi-homoharringtonine

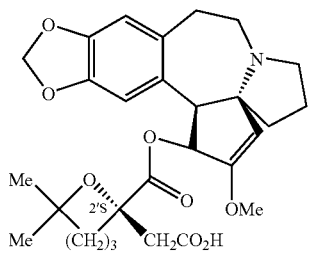

To a stirred solution of anhydro-epi-homoharringtonine (5 g, 9.48 mmol) in ethanol (162.5 ml) was added potassium hydroxide (5.35 mg, 94.8 mmol) and water (50 ml). After stirring 7 hours at ambient temperature and evaporation of ethanol under reduced pressure, the residual aqueous layer is saturated with sodium chloride and extracted with dichloromethane (3×100 ml). The combined organic layers were dried over magnesium sulfate, and evaporated to dryness. The resulting crude product was purified by column chromatography (silica 15-40 μm (50 g), dichloromethane then dichloromethane/methanol, 90:10 to 75:25) to provide the expected compound (4.6 g, 95%). The product thus obtained showed the following characteristics:

$^1$H NMR400 MHz (CDCl$_3$) (δ ppm, J Hz): 6.61 (1H, s, H-14*), 6.58 (1H, s, H-17*), 5.85 (3H, m, H-3+OCH$_2$O), 5.06 (1H, s, H-1), 3.80 (1H, d, J$_{4-3}$=9.6, H-4), 3.68 (3H, s, OCH$_3$), 3.09 (2H, m, H-11β+H-8α), 2.94 (1H, m, H-10α), 2.60 (2H, m, H-8β+H-10β), 2.37 (1H, dd, J$_{AB}$=14.0, J=6.7, H-11α), 2.16 and 1.90 (2H, 2d, J$_{AB}$=12.3, C$\underline{H}_2$CO$_2$), 2.02 (1H, m, H-6$_A$), 1.90 (1H, m, H-6$_B$), 1.76 (2H, m, CH$_2$-7), 1.5-1.2 (6H, m, 3×CH$_2$), 1.26 (3H, s, CH$_3$), 1.05 (3H, s, CH$_3$).

EXAMPLE 2

Preparation of (−)-cephalotaxyl (2′R)-2-carboxymethyl-6,6-dimethyl-2-tetrahydropyrane carboxylate or 4′-demethyl-anhydro-homoharringtonine

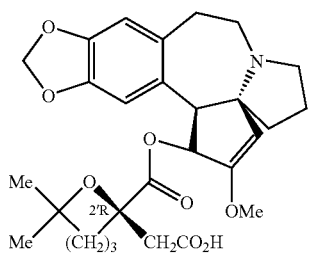

To a stirred solution of anhydro-homoharringtonine (1 g, 1.9 mmol) in ethanol (32.5 ml) was added potassium hydroxide (1.07 g, 19 mmol) and water (10 ml). After stirring 6 hours at ambient temperature and evaporation of ethanol under reduced pressure, the residual aqueous layer is saturated with sodium chloride and extracted with dichloromethane (3×25 ml). The combined organic layers were dried over magnesium sulfate, and evaporated to dryness. The resulting crude product was purified by column chromatography (silica 15-40 μm (10 g), dichloromethane then dichloromethane/methanol, 98:2 to 80:20) to provide the expected compound (678 mg, 69.5%). The product thus obtained showed the following characteristics:

$^1$H NMR 400 MHz (CDCl$_3$) (δ ppm, J Hz): 6.64 (1H, s, H-17), 6.56 (1H, s, H-14), 5.90 (3H, br,s, H-3+OCH$_2$O), 5.07 (1H, s, H-1), 3.80 (1H, d, J$_{4-3}$=9.6, H-4), 3.71 (3H, s, OCH$_3$), 3.09 (2H, m, H-11β+H-8α), 2.95 (1H, dd, J$_{AB}$=11.6, J=6.9, H-10α), 2.59 (2H, m, H-8β+H-10β), 2.37 (1H, dd, J$_{AB}$=14.0, J=6.7, H-11α), 2.07 and 2.02 (2H, 2d, J$_{AB}$=9.6, C$\underline{H}_2$CO$_2$), 1.91 (1H, m, H-6$_A$), 1.75 (3H, m, H-6$_B$+CH$_2$-7), 1.6-1.0 (6H, m, ×CH$_2$), 1.22 (3H, s, CH$_3$), 1.09 (3H, s, CH$_3$).

EXAMPLE 3

Preparation of (−)-cephalotaxyl (2′S)-2-ethoxycarbonylmethyl-6,6-dimethyl-2-tetrahydropyrane carboxylate or 4′-ethyl-4′-demethyl-anhydro-epi-homoharringtonine

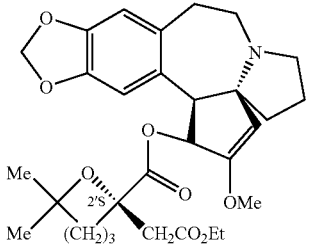

1°) Method A

A mixture of 4′-demethyl-anhydro-epi-homoharringtonine resulting from Example 1 (100 mg, 0.195 mmol) and a solution of boron trifluoride-etherate in ethanol 1.5 M (1.12 ml, 0.973 mmol) was stirred at ambient temperature for 15 hours and at 50° C. for 5 hours. After cooling of the reaction mixture, sodium hydroxide 2N was added to pH 10 and the resulting layer was extracted with dichloromethane (3×10 ml). The combined organic layers were washed with brine (50 ml), dried over magnesium sulfate and evaporated to dryness to provide the expected compound (80 mg crude, 76%). The crude product thus obtained showed the following characteristics:

$^1$-H NMR 400 MHz (CDCl$_3$) δ ppm, J Hz): 6.62 (1H, s, H-14*), 6.58 (1H, s, H-17*), 5.85 (3H, m, H-3+OCH$_2$O), 5.02 (1H, s, H-1), 4.05 (2H, m, OC$\underline{H}_2$CH$_3$), 3.79 (1H, d, J$_{4-3}$=9.6, H-4), 3.65 (3H, s, OCH$_3$), 3.26 (1H, m, H-11β), 3.13 (1H, m, H-8α), 2.99 (1H, m, H-10α), 2.66 (2H, m, H-8β+H-10β), 2.43 (1H, dd, JAB=14.5, J=6.7, H-11α), 2.12 and 1.78 (2H, 2d, $J_{AB}$=14.2, C$\underline{H}_2$CO2), 2.04 (1H, m, H-6$_A$), 1.88 (1H, m, H-6$_B$), 1.78 (2H, m, CH$_2$-7), 1.5-0.9 (6H, m, 3×CH$_2$), 1.22 (3H, t, J=7.2, OCH$_2$C$\underline{H}_3$), 1.16 (3H, s, CH3), 1.02 (3H, s, CH$_3$).

2°) Method B

Sodium hydride 60% (0.5 mg, 0.037 mmol) was added to a solution of anhydro-epi-homoharringtonine (39 mg, 0.074 mmol) resulting from Example 1 in dry ethanol (1 ml) and the resulting mixture was stirred at ambient temperature for 48 hours. After addition of water (5 ml) the resulting aqueous layer was extracted with ether (2×5 ml). The combined organic layers were washed with brine (2×100 ml), dried over magnesium sulfate and evaporated to dryness to provide the expected product (24 mg crude, 60%). The product thus obtained showed identical characteristics to this obtained with method A.

3°) Method C

To a stirred mixture of 4'-demethyl-anhydro-epi-homoharringtonine (50 mg, 0097 mmol) resulting from Example 1 in dry dichloromethane (0.35 ml) was added at 0° C. triethylamine (dried over potassium hydroxide) (13 μl, 0.097 mmol) and 2,4,6-trichlorobenzoyl chloride (15 μl, 0.097 mmol) over a period of 10 minutes. After stirring at ambient temperature for 2 hours a solution of 4-dimethylaminopyridine (23.8 mg, 0.195 mmol) and ethanol (10 μl, 0.175 mmol) in dry dichloromethane (0.15 ml) was added. After stirring at ambient temperature for 2.5 hours, the reaction mixture was diluted with dichloromethane (5 ml). The resulting organic layer was successively washed with water (5 ml) with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product thus obtained (44 mg crude, 85%) showed identical characteristics to this obtained with method A.

EXAMPLE 4

Preparation of (−)-cephalotaxyl (2'R)-2-ethoxycarbonylmethyl-6,6-dimethyl-2-tetrahydropyrane carboxylate or 4'-ethyl-4'-demethyl-anhydro-homoharringtonine

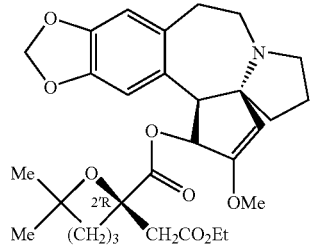

To a stirred mixture of 4'-demethyl-anhydro-homoharringtonine (256 mg, 0.498 mmol) resulting from Example 2 in dry dichloromethane (1.8 ml) was added at 0° C. triethylamine (dried over potassium hydroxide) (69 μl, 0.498 mmol) and 2,4,6-trichlorobenzoyl chloride (78 μl, 0.498 mmol) over a period of 10 minutes. After stirring at ambient temperature for 2.5 hours a solution of 4-dimethylaminopyridine (121 mg, 0.996 mmol) and ethanol (58 μl, 0.996 mmol) in dry dichloromethane (0.8 ml) was added. After stirring at ambient temperature for 15 hours, the reaction mixture was diluted with dichloromethane (5 ml). The resulting organic layer was successively washed with water (7 ml), with saturated sodium hydrogen carbonate solution (7 ml), with brine (5 ml). After a last extraction of the combined aqueous layers with dichloromethane (10 ml) the combined organic layers were dried over magnesium sulfate and evaporated to dryness. The resulting crude product was purified by column chromatography (silica 15-40 μm (8 g), dichloromethane then dichloromethane/methanol, 99:1 to 97:3) to provide the expected compound (241 mg, 89%). The product thus obtained showed the following characteristics:

IR (film) (cm-1): 1735 (CO2), 1657 (C=C—O), 1504 (Ar), 1221 (C—O), 1141 (C—O), 1080 (C—O), 1034 (C—O), 930.

$^1$H NMR 400 MHz (CDCl$_3$) (δ ppm, J Hz): 6.62 (1H, s, H-14*), 6.58 (1H, s, H-17*), 5.92 (1H, d, $J_{3-4}$=9.5, H-3), 5.89 and 5.81 (2H, 2s, OCH$_2$O), 5.06 (1H, s, H-1), 4.06 (2H, m, OC$\underline{H}_2$CH$_3$), 3.78 (1H, d, H-4), 3.72 (3H, s, OCH$_3$), 3.20 (2H, m, H-11β+H-8α), 3.01 (1H, m, H-10α), 2.67 (2H, m, H-8β+H-10β), 2.41 (1H, m, H-11α), 2.14 and 1.66 (2H, 2d, JAB=14.4, C$\underline{H}_2$CO$_2$), 2.06 (1H, m, H-6$_A$), 1.80 (1H, m, H-6$_B$), 1.68 (2H, m, CH$_2$-7), 1.65-1.2 (6H, m, 3×CH$_2$), 1.21 (3H, t, J=7.1, OCH$_2$C$\underline{H}_3$), 1.10 (3H, s, CH$_3$), 1.01 (3H, s, CH$_3$).

EXAMPLE 5

Preparation of (−)-cephalotaxyl (2'S)-2-isopropyloxycarbonylmethyl-6,6-dimethyl-2-tetrahydropyrane carboxylate or 4'-isopropyl-4'-demethyl-anhydro-epi-homoharringtonine

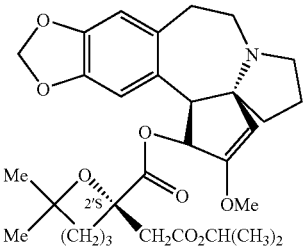

A mixture of 4'-demethyl-anhydro-epi-homoharringtonine resulting from Example 1 (100 mg, 0.195 mmol) and a solution of boron trifluoride-etherate in isopropanol 6 M (1.5 ml, 3.9 mmol) was stirred at ambient temperature for 15 hours. The reaction mixture was alkalinized to pH 10 with sodium hydroxide 2N (6 ml) and the resulting layer was extracted with dichloromethane (3×10 ml). The combined organic layers were washed with brine (10 ml), dried over magnesium sulfate and evaporated to dryness. The resulting crude product was purified by column chromatography (silica 15-40 μm (2.4 g), dichloromethane then dichloromethane/methanol, 99:1) to provide the expected compound (56 mg, 52%). %). The product thus obtained showed the following characteristics:

$^1$H NMR 400 MHz (CDCl$_3$) (δ ppm, J Hz): 6.61 (1H, s, H-14*), 6.58 (1H, s, H-17*), 5.84 (3H, m, H-3+OCH$_2$O), 5.02 (1H, s, H-1), 4.92 (1H, m, J=6.2, C$\underline{H}$(CH$_3$)$_2$), 3.78 (1H, d, $J_{4-3}$=9.6, H-4) 3.65 (3H, s, OCH$_3$), 3.24 (1H, m, H-11β), 3.09 (1H, m, H-8α), 2.94 (1H, m, H-10α), 2.60 (2H, m, H-8μ+H-10β), 2.40 (1H, dd, JAB=14.4, J=6.6, H-11α), 2.08 and 1.71 (2H, 2d, $J_{AB}$=13.8, C$\underline{H}_2$CO$_2$), 2.01 (1H, m, H-6$_A$), 1.9-1.0 (6H, m, 3×CH$_2$), 1.86 (1H, m, H-6$_B$), 1.75 (2H, m, CH$_2$-7), 1.20 (6H, d, J=6.2, CH(C$\underline{H}$$_3$)$_2$), 1.12 (3H, s, CH$_3$), 1.01 (3H, s, CH$_3$).

EXAMPLE 6

Preparation of (−)-cephalotaxyl (2'R)-2-isopropyloxycarbonylmethyl-6,6-dimethyl-2-tetrahydropyrane carboxylate or 4'-isopropyl-4'-demethyl-anhydro-homoharringtonine

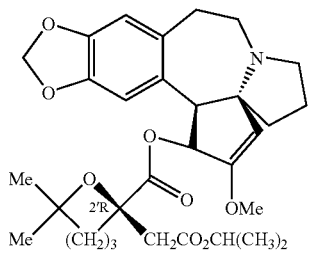

To a stirred mixture of 4'-demethyl-anhydro-homoharringtonine (255 mg, 0.498 mmol) resulting from Example 2 in dry dichloromethane (1.8 ml) was added at 0° C. triethylamine (dried over potassium hydroxide) (69 μl, 0.498 mmol) and 2,4,6-trichlorobenzoyl chloride (78 μl, 0.498 mmol) over a period of 10 minutes. After stirring at ambient temperature for 2.5 hours a solution of 4-dimethylaminopyridine (121 mg, 0.996 mmol) and isopropanol (76 μl, 0.996 mmol) in dry dichloromethane (0.8 ml) was added. After stirring at ambient temperature for 15 hours, the reaction mixture was diluted with dichloromethane (5 ml). The resulting organic layer was successively washed with water (7 ml), with saturated sodium hydrogen carbonate solution (7 ml), with brine (7 ml). The resulting aqueous layer was extracted with dichloromethane (10 ml), then the combined organic layers after drying over magnesium sulfate were evaporated to dryness. The resulting crude product was purified by column chromatography (silica 15-40 μm (8), dichloromethane then dichloromethane/methanol, 99:1 to 98:2) to provide the expected compound (216 mg, 78%). The product thus obtained showed the following characteristics:

IR (film) (cm$^{-1}$): 1731 (CO$_2$), 1656 (C=C—O), 1504 (Ar), 1223 (C—O), 1142 (C—O), 1108 (C—O), 1036 (C—O), 914. $^1$H NMR 400 MHz (CDCl$_3$) (δ ppm, J Hz): 6.62 (1H, s, H-14*), 6.59 (1H, s, H-17*), 5.91 (1H, d, J$_{3-4}$=9.6, H-3), 5.88 and 5.79 (2H, 2s, OCH$_2$O), 5.04 (1H, s, H-1), 4.93 (1H, m, J=6.3, C$\underline{H}$(CH$_3$)$_2$), 3.79 (1H, d, J$_{4-3}$=9.3, H-4), 3.72 (3H, s, OCH$_3$), 3.19 (2H, m, H-11β+H-8α), 2.99 (1H, m, H-10α), 2.62 (2H, m, H-8β+H-10β), 2.41 (1H, m, H-11α), 2.09 and 1.70 (2H, 2d, J$_{AB}$=14.1, C$\underline{H}$$_2$CO2), 2.04 (1H, m, H-6$_A$), 1.91 (1H, m, H-6$_B$), 1.77 (2H, m, CH$_2$-7), 1.65-1.2 (6H, m, 3×CH$_2$), 1.19 (6H, d, J=6.3, CH(C$\underline{H}$$_3$)$_2$), 1.11 (3H, s, CH$_3$), 1.02 (3H, s, CH$_3$).

EXAMPLE 7

Preparation of (−)-cephalotaxyl (2'S)-2-benzyloxycarbonylmethyl-6,6-dimethyl-2-tetrahydropyrane carboxylate or 4'-benzyl-4'-demethyl-anhydro-epi-homoharringtonine

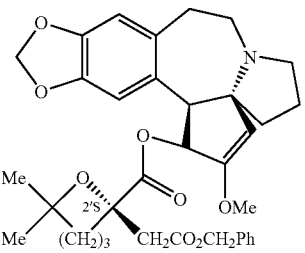

To a stirred mixture of 4'-demethyl-anhydro-epi-homoharringtonine (62 mg, 0.12 mmol) resulting from Example 1 in dry dichloromethane (0.43 ml) was added at 0° C. triethylamine (dried over potassium hydroxide) (17 μl, 0.12 mmol) and 2,4,6-trichlorobenzoyl chloride (19 μl, 0.12 mmol) over a period of 10 minutes. After stirring at ambient temperature for 2.5 hours a solution of 4-dimethylaminopyridine (29 mg, 0.14 mmol) and benzylic alcohol (25 μl, 0.24 mmol) in dry dichloromethane (0.19 ml) was added. After stirring at ambient temperature for 15 hours, the reaction mixture was diluted with dichloromethane (5 ml). The resulting organic layer was successively washed with water (5 ml), with saturated sodium hydrogen carbonate solution (5 ml), with brine (5 ml). The resulting, aqueous layer was extracted with dichloromethane (10 ml), then the combined organic layers after drying over magnesium sulfate were evaporated to dryness. The resulting crude product was purified by column chromatography (silica 15-40 μm (3 g), dichloromethane then dichloromethane/methanol, 99.5:0.5 to 98.5:1.5) to provide the expected compound (40 mg, 55%). The product thus obtained showed the following characteristics:

$^1$H NMR 400 MHz (CDCl3) (δ ppm, J Hz): 7.35,(5H, m, Ph), 6.58 (1H, s, H-17), 6.47 (1H, s, H-14), 5.81 and 5.71 (2H, 2d, J$_{AB}$=1.4, OCH$_2$O), 5.81 (1H, d, J=9.2, H-3), 5.08 and 4.99 (2H, 2d, J$_{AB}$=12.4 OC$\underline{H}$$_2$Ph), 5.0 (1H, s, H-1), 3.70 (1H, d, J$_{4-3}$=9.7, H-4), 3.63 (3H, s, OCH$_3$), 3.23 (1H, m, H-11β), 3.08 (1H, m, H-8α), 2.93 (1H, m, H-10α), 2.59 (2H, m, (H-8β+H-10β), 2.37 (1H, dd, J$_{AB}$=14.3, J=7.0, H-11α), 2.16 and 1.80 (2H, 2d, J$_{AB}$=14.3, C$\underline{H}$$_2$CO$_2$), 2.0 (1H, m, H-6$_A$), 1.90 (1H, m, H-6$_B$), 1.75 (2H, m, CH$_2$-7), 1.6-0.8 (6H, m, 3×CH$_2$), 1.07 (3H, s, CH$_3$), 1.02 (3H, s, CH$_3$).

EXAMPLE 8

Preparation of (−)-cephalotaxyl (2'R)-2-benzyloxycarbonylmethyl-6,6-dimethyl-2-tetrahydropyrane carboxylate or 4-benzyl-4'-demethyl-anhydro-homoharringtonine

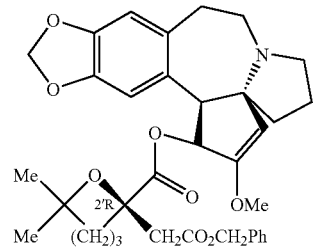

To a stirred mixture of 4'-demethyl-anhydro-homoharringtonine (255 mg, 0.496 mmol) resulting from, Example 2 in dry dichloromethane (1.8 ml) was added at 0° C. triethylamine (dried over potassium hydroxide) (69 □l, 0.496 mmol) and 2,4,6-trichlorobenzoyl chloride (78 μl, 0.496 mmol) over a period of 10 minutes. After stirring at ambient temperature for 2.5 hours a solution of 4-dimethylaminopyridine (121 mg, 0.992 mmol) and benzylic alcohol (102 μl, 0.992 mmol) in dry dichloromethane (0.8 ml) was added. After stirring at ambient temperature for 15 hours, the reaction mixture was diluted with dichloromethane (0.8 ml). The resulting organic layer was successively washed with water (5 ml), with saturated sodium hydrogen carbonate solution (5 ml), with brine (5 ml). The, resulting aqueous layer was extracted with dichloromethane (10 ml), then the combined organic layers after drying over magnesium sulfate were evaporated to dryness. The resulting crude product was purified by column chromatography (silica 15-40 μl (8 g), dichloromethane then dichloromethane/methanol, 99:1 to 98:2) to provide the expected compound (278 mg, 93%). The product thus obtained showed the following characteristics:

IR (film) (cm$^{-1}$): 1737 (CO$_2$), 1656 (C=C—O), 1504 (Ar), 1222 (C—O), 1141 (C—O), 1081 (C—O), 1036 (C—O), 911. $^1$H NMR 400 MHz (CDCl$_3$) (δ ppm, J Hz): 7.34 (5H, m, Ph), 6.60 (1H, s, H-17), 6.52 (1H, s, H-14), 5.91 (1H, d, J=9.8, H-3), 5.77 and 5.61 (2H, 2s, OCH$_2$O), 5.05 (2H, s, OCH$_2$Ph), 5.03 (1H, s, H-1), 3.75 (1H, d, J$_{4-3}$=9.7, H-4), 3.67 (3H, s, OCH$_3$), 3.11 (2H, m, H-11β+H-8α), 2.93 (1H, m, H-10α), 2.59 (2H, m, H-8β+H-10β), 2.36 (1H, dd, J$_{AB}$=14.0, J=6.6, H-11α) 2.18 and 1.66 (2H, 2d, J$_{AB}$=14.5, CH$_2$CO$_2$), 2.0 (1H, m, H-6$_A$), 1.89 (1H, m, H-6$_B$), 1.75 (2H, m, CH$_2$-7), 1.7-1.2 (6H, m, 3×CH$_2$), 1.06 (3H, s, CH$_3$), 1.04 (3H, s, CH$_3$).

EXAMPLE 9

Preparation of (−)-cephalotaxyl (2'R)-2-methylthiocarbonylmethyl-6,6-dimethyl-2-tetrahydropyrane carboxylate or 4'-methylthio-4'-demethoxy-anhydro-homoharringtonine

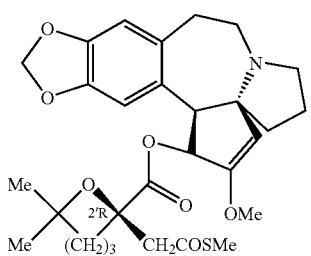

To a stirred mixture of 4'-demethyl-anhydro-homoharringtonine (404 mg, 0.786 mmol) resulting from Example 2 in dry dichloromethane (2.75 ml) was added at 0° C. triethylamine (dried over potassium hydroxide) (105 μl, 0.786 mmol) and 2,4,6-trichlorobenzoyl chloride (123 μl, 0.786 mmol) over a period of 10 minutes. After stirring at ambient temperature for 2.5 hours a solution of 4-dimethylaminopyridine (192 mg, 1.57 mmol) in dry dichloromethane (0.8 ml) and methanethiol (218 μl, 1.57 mmol) were added. After stirring at ambient temperature for 15 hours, the reaction mixture was diluted with dichloromethane (10 ml). The resulting organic layer was successively washed with water (14 ml), with saturated sodium hydrogen carbonate solution (14 ml), with brine (14 ml). The resulting aqueous layer was extracted with dichloromethane (20 ml), then the combined organic layers after drying over magnesium sulfate were evaporated to dryness. The resulting crude product was purified by column chromatography (silica 15-40 μm (12 g), dichloromethane then dichloromethane/methanol, 99:1 to 96:4) to provide the expected compound (228 mg, 53%). The product thus obtained showed the following characteristics:

IR (film) (cm$^{-1}$): 1741 (CO$_2$), 1690 (COS),1656 (C=C—O),1504 (Ar), 1222 (C—O), 1142 (C—O), 1078 (C—O), 1035 (C—O), 913. $^1$H NMR 400 MHz (CDCl$_3$) (δ ppm, J Hz): 6.64 (1H, s, H-14*), 6.58 (1H, s, H-17*), 5.91 (1H, d, J$_{3-4}$=9.7, H-3), 5.88 and 5.84 (2H, 2s, OCH$_2$O), 5.04 (1H, s, H-1), 3.79 (1H, H-4), 3.70 (3H, s, OCH$_3$), 3.10 (2H, m, H-11β+H-8α), 2.95 (1H, m, H-10α), 2.60 (2H, m, H-8β+H-10β), 2.35 (1H, d, J$_{AB}$=14.5, CH$_A$COS) and (1H, m, H-11α), 2.23 (3H, s, SCH$_3$), 2.03 (1H, m, H-6$_A$), 1.90 (1H, m, H-6$_B$), 1.75 (2H, m, CH$_2$-7), 1.8-1.2 (7H, m, 3×CH$_2$+CH$_B$COS), 1.14 (3H, s, CH$_3$),1.03 (3H, s, CH$_3$).

EXAMPLE 10

Preparation of (−)-cephalotaxyl (2'S)-2-ethylthiocarbonylmethyl-6,6-dimethyl-2-tetrahydropyrane carboxylate or 4'-ethylthio-4'-demethoxy-anhydro-epi-homoharringtonine

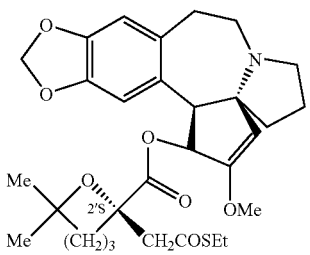

To a stirred mixture of 4'-demethyl-anhydro-epi-homoharringtonine (70 mg, 0.136 mmol) resulting from Example 1 in dry dichloromethane (0.49 ml) was added at 0° C. triethylamine (dried over potassium hydroxide) (19 μl, 0.136 mmol) and 2,4,6-trichlorobenzoyl chloride (21 μl, 0.136 mmol) over a period of 10 minutes. After stirring at ambient temperature for 2.5 hours a solution of 4-dimethylaminopyridine (33 mg, 0.272 mmol) and ethanethiol (20, μl, 0.272 mmol) in dry dichloromethane (0.25 ml) was added. After stirring at ambient temperature for 15 hours, the reaction mixture was diluted with dichloromethane (5 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product was purified by column chromatography (silica 15-40 μm (2 g); dichloromethane/methanol, 99:1) to provide the expected compound (40 mg, 53%). The product thus obtained showed the following characteristics:

$^1$H NMR 400 MHz (CDCl$_3$) (δ ppm, J Hz): 6.64 (1H, s, H-14*), 6.56 (1H, s, H-17*), 5.87 and 5.83 (3H, 2d, J$_{AB}$=1.5, OCH$_2$O+H-3), 5.02 (1H, s, H-1), 3.78 (1H, d, J$_{4-3}$=9.7, H-4), 3.65 (3H, s, OCH$_3$), 3.24 (1H, m, H-11β), 3.09 (1H, m, H-8α), 2.95 (1H, m, H-10α), 2.79 (2H, m, SC$\underline{H}_2$CH$_3$), 2.60 (2H, m, H-8β+H-10β), 2.41 (1H, dd, J$_{AB}$=14.2, J=7.0, H-11α), 2.28 and 1.83 (2H, 2d, J$_{AB}$=14.4, C$\underline{H}_2$COS), 2.01 (1H, m, H-6$_A$), 1.91 (1H, m, H-6$_B$), 1.75 (2H, m, CH$_2$-7), 1.5-0.85 (6H, m, 3×CH$_2$), 1.20 (3H, t, J=7.4, SCH$_2$C$\underline{H}_3$), 1.14 (3H, s, CH$_3$), 1.01 (3H, s, CH$_3$).

EXAMPLE 11

Preparation of (−)-cephalotaxyl (2'R)-2-ethylthio-carbonylmethyl-6,6-dimethyl-2-tetrahydropyrane carboxylate or 4'-ethylthio-4'-demethoxy-anhydro-homoharringtonine

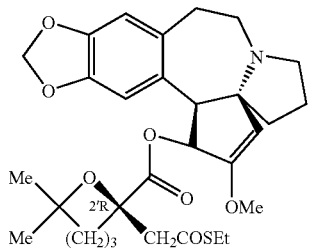

To a stirred mixture of 4'-demethyl-anhydro-homoharringtonine (250 mg, 0.486 mmol) resulting from Example 2 in dry dichloromethane (1.8 ml) was added at 0° C. triethylamine (dried over potassium hydroxide) (68 μl, 0.486 mmol) and 2,4,6-trichlorobenzoyl chloride (76 μl, 0.486 mmol) over a period of 10 minutes. After stirring at ambient temperature for 2.5 hours a solution of 4-dimethylaminopyridine (119 mg, 0.973 mmol) and ethanethiol (72 μl, 0.973 mmol) in dry dichloromethane (0.8 ml) was added. After stirring at ambient temperature for 15 hours, the reaction mixture was diluted with dichloromethane (5 ml). The resulting organic layer was successively washed with water (7 ml), with saturated sodium hydrogen carbonate solution (7 ml), with brine (7 ml). The resulting aqueous layer was extracted with dichloromethane (10 ml), then, the combined organic layers after drying over magnesium sulfate were evaporated to dryness. The resulting crude product was purified by column chromatography (silica 15-40 μm (7 g), dichloromethane then dichloromethane/methanol, 99:1 to 98:2) to provide the expected compound (251 mg, 93%). The product thus obtained showed the following characteristics:

IR (film) (cm$^{-1}$) 1740 (CO$_2$), 1688 (COS), 1657 (C=C—O), 1504 (Ar), 1223 (C—O), 1142 (C—O), 1078 (C—O), 1037 (C—O), 910. $^1$H NMR 400 MHz (CDCl$_3$) (δ ppm, J Hz): 6.64 (1H, s, H-14*), 6.59 (1H, s, H-17*), 5.91 (1H, H-3), 5.90 and 5.85 (2H, 2s, OCH$_2$O), 5.03 (1H, s, H-1), 3.80 (1H, H-4), 3.71 (3H, s, OCH$_3$), 3.14 (2H, m, H-11β+H-8α), 2.88 (1H, m, H-10α), 2.81 (2H, m, SC$\underline{H}_2$CH3), 2.61 (2H, m, H-8□+H-10β), 2.38 (1H, m, H-11□), 2.35 (1H, d, JAB=14.8, C$\underline{H}_A$COS), 2.02 (1H, m, H-6$_A$), 1.91 (1H, m, H-6$_B$), 1.77 (2H, m, CH$_2$-7), 1.65-1.1 (7H, m, 3×CH$_2$+ C$\underline{H}_B$COS), 1.20 (3H, t, J=7.4, SCH$_2$C$\underline{H}_3$),1.14 (3H, s, CH3), 1.02 (3H, s, CH3).

EXAMPLE 12

Preparation of (−)-cephalotaxyl (2'S)-2-isopropylthiocarbonylmethyl-6,6-dimethyl-2-tetrahydropyrane carboxylate or 4'-isopropylthio-4'-demethoxy-anhydro-epi-homoharringtonine

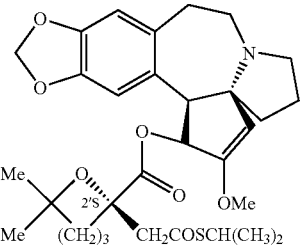

To a stirred mixture of 4'-demethyl-anhydro-epi-homoharringtonine (49 mg, 0.095 mmol) resulting from Example 1 in dry dichloromethane (0.34 ml) was added at 0° C. triethylamine (dried over potassium hydroxide) (13 μl, 0.095 mmol) and 2,4,6-trichlorobenzoyl chloride (15 μl, 0.095 mmol) over a period of 10 minutes. After stirring at ambient temperature for 2.5 hours a solution of 4-dimethylaminopyridine (23 mg, 0:19 mmol) and isopropanethiol (18 μl, 0.19 mmol) in dry dichloromethane (0.2 ml) was added. After stirring at ambient temperature for 15 hours, the reaction mixture was diluted with dichloromethane (5 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product was purified by column chromatography (silica 15-40 □m (1 g), dichloromethane/methanol, 99:1) to provide the expected compound (40 mg, 74%). The product thus obtained showed the following characteristics:

$^1$H NMR 400 MHz (CDCl$_3$) (δ ppm, J Hz): 6.64 (1H, s, H-14*), 6.57 (1H, s, H-17*), 5.87 (3H, 2d, J$_{AB}$=1.4, OCH$_2$O+H-3), 5.02 (1H, s, H-1), 3.78 (1H, d, J$_{4-3}$=9.7, H-4), 3.65 (3H, s, OCH$_3$), 3.55 (1H, m, J=6.9, CH(CH$_3$)$_2$), 3.23 (1H, m, H-11β), 3.09 (1H, m, H-8α), 2.94 (1H, m, H-10α), 2.60 (2H, m, H-8β+H-10β), 2.42 (1H, dd, J$_{AB}$=13.9, J=6.8, H-11α), 2.25 and 1.79 (2H, 2d, J$_{AB}$=14.3, C$\underline{H}_2$COS), 2.04 (1H, m, H-6$_A$), 1.90 (1H, m, H-6$_B$), 1.75 (2H, m, CH$_2$-7), 1.45-0.85 (6H, m, 3×CH$_2$), 1.25 (6H, d, J=6.9, CH(C$\underline{H}_3$)$_2$), 1.14 (3H, s, CH$_3$), 1.01 (3H, s, CH$_3$).

EXAMPLE 13

Preparation of (−)-cephalotaxyl (2'R)-2-isopropylthiocarbonylmethyl-6,6-dimethyl-2-tetrahydropyrane carboxylate or 4'-isopropylthio-4'-demethoxy-anhydro-homoharringtonine

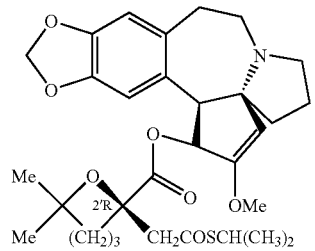

To a stirred mixture of 4'-demethyl-anhydro-homoharringtonine (248 mg, 0.483 mmol) resulting from Example 2 in dry dichloromethane (1.8 ml) was added at 0° C. triethylamine (dried over potassium hydroxide) (67 µl, 0.483 mmol) and 2,4,6-trichlorobenzoyl chloride (76 µl, 0.483 mmol) over, a period of 10 minutes. After stirring at ambient temperature for 2.5 hours a solution of 4-dimethylaminopyridine (120 mg, 0:965 mmol) and isopropanethiol (90 µl, 0.965 mmol) in dry dichloromethane (0.8 ml) was added. After stirring at ambient temperature for 15 hours, the reaction mixture was diluted with dichloromethane (5 ml). The resulting organic layer was successively washed with water (7 ml), with saturated sodium hydrogen carbonate solution (7 ml), with brine (7 ml). The resulting aqueous layer was extracted with dichloromethane (10 ml), then the combined organic layers after drying over magnesium sulfate were evaporated to dryness. The resulting crude product was purified by column chromatography (silica 15-40 □m (8 g), dichloromethane then dichloromethane/methanol, 99:1 to 98:2) to provide the expected compound (267 mg, 97%). The product thus obtained showed the following characteristics:

IR (film) (cm$^{-1}$): 1740 (CO$_2$), 1687 (COS), 1656 (C=C—O), 1504 (Ar), 1223 (C—O), 1142 (C—O), 1078 (C—O), 1036 (C—O), 912. $^1$H NMR 400 MHz (CDCl$_3$) (δ ppm, J Hz): 6.64 (1H, s, H-14*), 6.58 (1H, s, H-17*), 5.91 (1H, d, J$_{3-4}$=9.7, H-3), 5.89 and 5.85 (2H, 2s, OCH$_2$O), 5.04 (1H, s, H-1), 3.79 (1H, d, H-4), 3.71 (3H, s, OCH$_3$), 3.56 (1H, m, J=6.9, CH(CH$_3$)$_2$), 3.18 (2H, m, H-11β+H-8α), 2.99 (1H, m, H-10α), 2.61 (2H, m, H-8β+H-10β), 2.39 (1H, m, H-11α), 2.31 (1H, d, J$_{AB}$=14.3, CH$_A$COS), 2.04 (1H, m, H-6$_A$), 1.92 (1H, m, H-6$_B$), 1.78 (2H, m, CH2-7), 1.7-1.2 (7H, m, 3×CH2+CH$_B$COS), 1.25 and 1.24 (6H, 2d, J=6.8, CH(CH$_3$)$_2$), 1.13 (3H, s, CH3), 1.0 (3H, s, CH3).

EXAMPLE 14

Preparation of (–)-cephalotaxyl (2'S)-2-tert-butylthiocarbonylmethyl-6,6-dimethyl-2-tetrahydropyrane carboxylate or 4'-tert-butylthio-4-demethoxy-anhydro-epi-homoharringtonine

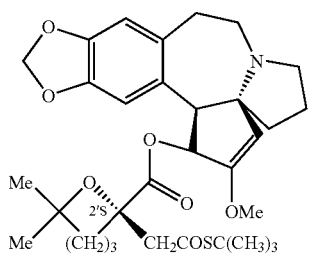

To a stirred mixture of 4'-demethyl-anhydro-epi-homoharringtonine (70 mg, 0.136 mmol) resulting from Example 1 in dry dichloromethane (0.49 ml) was added at 0° C. triethylamine (dried over potassium hydroxide) (19 µl, 0.136 mmol) and 2,4,6-trichlorobenzoyl chloride (21 µl, 0.136 mmol) over a period of 10 minutes. After stirring at ambient temperature for 2.5 hours a solution of 4-dimethylaminopyridine (33 mg, 0.272 mmol) and tert-butanethiol (31 µl, 0.272 mmol) in dry dichloromethane (0.3 ml) was added. After stirring at ambient temperature for 15 hours, the reaction mixture was diluted with dichloromethane (5 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product was purified by column chromatography (silica 15-40 µm (1.5 g), dichloromethane/methanol, 99:1) to provide the expected compound (46 mg, 58%). The product thus obtained showed the following characteristics:

$^1$H NMR 400 MHz (CDCl3) (δ ppm, J Hz): 6.65 (1H, s, H-14*), 6.56 (1H, s, H-17*), 5.87 and 5.84 (2H, 2d, J$_{AB}$=1.5, OCH$_2$O), 5.84 (1H, d, J$_{3-4}$=10.0, H-3), 5.02 (1H, s, H-1), 3.78 (1H, d, J$_{4-3}$=9.6, H-4), 3.64 (3H, s, OCH$_3$), 3.24 (1H, m, H-11β), 3.09 (1H, m, H-8α), 2.96 (1H, m, H-10α), 2.60 (2H, m, H-8β+H-10β), 2.42 (1H, dd, J$_{AB}$=14.3, J=7.0, H-11α), 2.20 and 1.71 (2H, 2d, J$_{AB}$=14.1, CH$_2$COS), 2.01 (1H, m, H-6$_A$), 1.88 (1H, m, H-6$_B$), 1.75 (2H, m, CH$_2$-7), 1.6-0.85 (6H, m, 3×CH$_2$), 1.41 (9H, s, C(CH3) 3), 1.13 (3H, s, CH$_3$), 1.01 (3H, s, CH$_3$).

EXAMPLE 15

Preparation of (–)-cephalotaxyl (2'R)-2-tert-butylthiocarbonylmethyl-6,6-dimethyl-2-tetrahydropyrane carboxylate or 4'-tert-butylthio-4'-demethoxy-anhydro-homoharringtonine

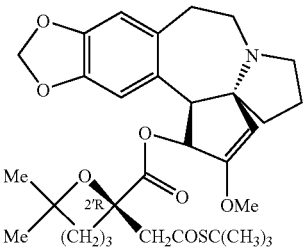

To a stirred mixture of 4'-demethyl-anhydro-homoharringtonine (234 mg, 0.455 mmol) resulting from Example 2 in dry dichloromethane (1.8 ml) was added at 0° C. triethylamine (dried over potassium hydroxide) (63 µl, 0.455 mmol) and 2,4,6-trichlorobenzoyl chloride (72 µl, 0.455 mmol) over a period of 10 minutes. After stirring at ambient temperature for 2.5 hours a solution of 4-dimethylaminopyridine (111 mg, 0.911 mmol) and tert-butanethiol (102 µl, 0.911 mmol) in dry dichloromethane (0.8 ml) was added. After stirring at ambient temperature for 15 hours, the reaction mixture was diluted with dichloromethane (5 ml). The resulting organic layer was successively washed with water (7 ml), with saturated sodium hydrogen carbonate solution (7 ml), with brine (7 ml). The resulting aqueous layer was extracted with dichloromethane (10 ml), then the combined organic layers after drying over magnesium sulfate were evaporated to dryness. The resulting crude product was purified by column chromatography (silica 15-40 µm (6 g), dichloromethane then dichloromethane/methanol, 99:1 to 98:2) to provide the expected compound (212 mg, 81%). The product thus obtained showed the following characteristics:

IR (film) (cm$^{-1}$): 1738 (CO$_2$), 1681 (COS), 1659 (C=C—O), 1504 (Ar), 1222 (C—O), 1141 (C—O), 1077 (C—O), 1037 (C—O), 911. $^1$H NMR 400 MHz (CDCl$_3$) (δ ppm, J Hz): 6.65 (1H, s, H-14*), 6.59 (1H, s, H-17*), 5.89

(3H, m, OCH$_2$O+H-3), 5.03 (1H, s, H-1), 3.76 (1H, H-4), 3.72 (3H, s, OCH$_3$), 3.13 (2H, m, H-11β+H-8α), 3.0 (1H, m, H-10α), 2.63 (2H, m, H-8β+H-10β), 2.40 (1H, m, H-11α), 2.23 (1H, d, J$_{AB}$=12.2, CH$_A$COS), 2.01 (1H, m, H-6A), 1.93 (1H, m, H-6B), 1.78 (2H, m, CH2-7), 1.7-1.2 (6H, m, 3×CH2+CH$_B$COS), 1.41 (9H, s, C(CH$_3$)$_3$), 1.12 (3H, s, CH$_3$), 0.99 (3H, s, CH$_3$).

EXAMPLE 16

Preparation of (–)-cephalotaxyl (2'S)-2-(methylamino)carbonylmethyl-6,6-dimethyl-2-tetrahydropyrane carboxylate or 4'-methylamino-4'-demethoxy-anhydro-epi-homoharringtonine

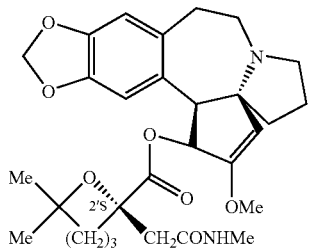

To a stirred mixture of 4'-demethyl-anhydro-epi-homoharringtonine (52 mg, 0.10 mmol) resulting from Example 1 in dry dichloromethane (0.34 ml) was added at 0° C. triethylamine (dried over potassium hydroxide) (14 μl, 0.10 mmol) and 2,4,6-trichlorobenzoyl chloride (15.5 μl, 0.10 mmol) over a period of 10 minutes. After stirring at ambient temperature for 2.5 hours a solution of 4-dimethylaminopyridine (49 mg, 0.40 mmol) in dry dichloromethane (0.3 ml) and methylamine hydrochloride (13.5 mg, 0.20 mmol) were added. After stirring at ambient temperature for 15 hours, the reaction mixture was diluted with dichloromethane (5 ml). The resulting organic layer was successively washed with water (5 ml), with saturated sodium hydrogen carbonate solution (5 ml). The resulting aqueous layer was extracted with dichloromethane (10 ml), then the combined organic layers after drying over magnesium sulfate were evaporated to dryness. The resulting crude product was purified by column chromatography (silica 15-40 μm (2 g), dichloromethane then dichloromethane/methanol, 98:2) to provide the expected compound (47 mg, 89%). The product thus obtained showed the following characteristics:

$^1$H NMR 400 MHz (CDCl$_3$) (δ ppm, J Hz): 6.61 (1H, s, H-14*), 6.59 (1H, s, H-17*), 6.48 (1H, m, NH), 5.85 (3H, m, OCH$_2$O+H-3), 5.03 (1H, s, H-1), 3.79 (1H, d, J$_{4-3}$=9.7, H-4), 3.67 (3H, s, OCH$_3$), 3.17 (1H, m, H-11β), 3.09 (1H, m, H-8α), 2.93 (1H, m, H-10α), 2.74 (3H, d, J=4.9, NHCH$_3$), 2.59 (2H, m, H-8β+H-10β), 2.37 (1H, dd, J$_{AB}$=14.2, J=7.0, H-11α), 2.11 and 1.84 (2H, 2d, J$_{AB}$=14.5, CH$_2$CON), 2.02 (1H, m, H-6$_A$), 1.89 (2H, m, H-6$_B$+CH), 1.75 (2H, m, CH$_2$-7), 1.4-1.1 (5H, m, CH+2×CH$_2$), 1.18 (3H, s, CH$_3$), 0.96 (3H, s, CH$_3$).

EXAMPLE 17

Preparation of (–)-cephalotaxyl (2'S)-2-(dimethylamino)carbonylmethyl-6,6-dimethyl-2-tetrahydropyrane carboxylate or 4'-dimethylamino-4'-demethoxy-anhydro-epi-homoharringtonine

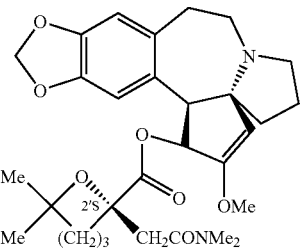

To a stirred mixture of 4'-demethyl-anhydro-epi-homoharringtonine (60 mg, 0.117 mmol) resulting from Example 1 in dry dichloromethane (0.4 ml) was added at 0° C. triethylamine (dried over potassium hydroxide) (16.2 μl, 0.111 mmol) and 2,4,6-trichlorobenzoyl chloride (18 μl, 0.117 mmol) over a period of 10 minutes. After stirring at ambient temperature for 2.5 hours a solution of 4-dimethylaminopyridine (28.6 mg, 0.234 mmol) in dry dichloromethane (0.16 ml) and dimethylamine (in excess) were added. After stirring at ambient temperature for 15 hours, the reaction mixture was diluted with dichloromethane (5 ml). The resulting organic layer was successively washed with water (5 ml), with saturated sodium hydrogen carbonate solution (5 ml), with brine (5 ml). The resulting aqueous, layer was extracted with dichloromethane (10 ml), then the combined organic layers after drying over magnesium sulfate were evaporated to dryness. The resulting crude product was purified by column chromatography (silica 15-40 μm (1.5 g), dichloromethane then dichloromethane/methanol, 99:1 to 98:2) to provide the expected compound (11 mg, 17.4%). The product thus obtained showed the following characteristics:

$^1$H NMR 400 MHz (CDCl$_3$) (δ ppm, J Hz): 6.59 (2H, s, H-17+H-14), 5.88 (1H, d, J3-4=9.7, H-3), 5.84 (2H, s, OCH$_2$O), 5.01 (1H, s, H-1), 3.80 (1H, d, J$_{4-3}$=9.9, H-4), 3.66 (3H, s, OCH$_3$), 3.23 (1H, m, H-11β), 3.09 (1H, m, H-8α), 2.95 (1H, m, H-10α) and (3H, s, NCH$_3$), 2.88 (3H, s, NCH$_3$), 2.60 (2H, m, H-8□+H-10β), 2.37 (1H, m, H-11α), 2.35 and 1.73 (2H, 2d, J$_{AB}$=13.5, CH$_2$CON), 2.01 (2H, m, CH$_2$-6), 1.95-1.10 (8H, m, CH2-7+3×CH$_2$), 1.08 (3H, 5, CH$_3$), 0.96 (3H, s, CH$_3$).

EXAMPLE 18

Preparation of (–)-cephalotaxyl (2'S)-2-(diethylamino)carbonylmethyl-6,6-dimethyl-2-tetrahydropyrane carboxylate or 4'-diethylamino-4'-demethoxy-anhydro-epi-homoharringtonine

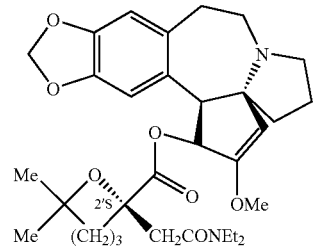

To a stirred mixture of 4'-demethyl-anhydro-epi-homoharringtonine (57 mg, 0.11 mmol) resulting from Example 1 in dry dichloromethane (0.34 ml) was added at 0° C. triethylamine (dried over potassium hydroxide) (15.3 µl, 0.11 mmol) and 2,4,6-trichlorobenzoyl chloride (17.1 µl, 0.11 mmol) over a period of 10 minutes. After stirring at ambient temperature for 2.5 hours a solution of 4-dimethylaminopyridine (27.4 mg, 0.22 mmol) and diethylamine (23 µl, 0.22 mmol) in dry dichloromethane (0.16 ml) was added. After stirring at ambient temperature for 15 hours, the reaction mixture was diluted with dichloromethane (5 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product was purified by column chromatography (silica 15-40 µm (1.5 g), dichmoromethane then dichloromethane/methanol, 99:1 to 98:2) to provide the expected compound (50 mg, 80%). The product thus obtained showed the following characteristics:

$^1$H NMR 400 MHz (CDCl$_3$) (δ ppm, J Hz): 6.60 (1H, s, H-14*), 6.58 (1H, s, H-17*), 5.84 (3H, m, OCH$_2$O+H-3), 5.02 (1H, s, H-1), 3.81 (1H, d, J$_{4-3}$=9.6, H-4), 3.69 (2H, m, NC$\underline{H}_2$CH$_3$), 3.66 (3H, s, OCH$_3$), 3.21 (1H, m, H-11β), 3.08 (1H, m, H-8α), 2.95 (3H, m, H-10α+NC$\underline{H}_2$CH$_3$), 2.60 (2H, m, H-8β+H-10β), 2.41 and 1.71 (2H, 2d, J$_{AB}$=13.3, C$\underline{H}_2$COn), 2.37 (1H, dd, J$_{AB}$=14.2, J=7.0, H-11α), 2.01 (1H, m, H-6$_A$), 2.0-1.0 (6H, m, 3×CH$_2$), 1.89 (1H, m, H-6$_B$), 1.75 (2H, m, CH$_2$-7), 1.10 (9H, m, N(CH$_2$C$\underline{H}_3$)$_2$+CH$_3$), 0.92 (3H, s, CH$_3$).

EXAMPLE 19

Preparation of (−)-cephalotaxyl-(2'R)-2-(diethylamino)carbonylmethyl-6,6-dimethyl-2-tetrahydropyrane carboxylate or 4'-diethylamino-4'-demethoxy-anhydro-homoharringtonine

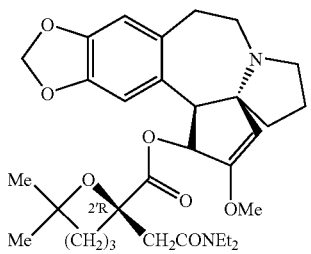

To a stirred mixture of 4'-demethyl-anhydro-homoharringtonine (250 mg, 0.487 mmol) resulting from Example 2 in dry dichloromethane (1.8 ml) was added at 0° C. triethylamine (dried over potassium hydroxide) (65 µl, 0.487 mmol) and 2,4,6-trichlorobenzoyl chloride (76 µl, 0.487 mmol) over a period of 10 minutes. After stirring at ambient temperature for 2.5 hours a, solution of 4-dimethylaminopyridine (119 mg, 0.974 mmol) and diethylamine (105 µl, 0.974 mmol) in dry dichloromethane (0.8 ml) was added. After stirring at ambient temperature for 15 hours, the reaction mixture was diluted with dichloromethane (5 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product was purified by column chromatography (silica 15-40 □m (8 g), dichloromethane then dichloromethane/methanol, 99:1 to 97:3) to provide the expected compound (226 mg, 82%). The product thus obtained showed the following characteristics:

$^1$H NMR 400 MHz (CDCl$_3$) (δ ppm, J Hz): 6.63 (1H, s, H-14*), 6.59 (1H, s, H-17*), 5.86 (1H, d, J$_{3-4}$=9.6, H-3), 5.82 and 5.78 (2H, 2s, OCH$_2$O), 5.04 (1H, s, H-1), 3.81 and 3.72 (2H, 2m, NC$\underline{H}_2$CH$_3$), 3.80 (1H, d, H-4), 3.70 (3H, s, OCH$_3$), 3.12 (2H, m, H-11β+H-8α), 2.90 (3H, m, H-10α+NC$\underline{H}_2$CH$_3$), 2.59 (2H, m, H-8β+H-10β), 2.38 (1H, dd, J$_{AB}$=14.2, J=6.7, H-11α), 2.24 (1H, d, J$_{AB}$=13.1, C$\underline{H}_A$CON), 2.02 (1H, m, H-6$_A$), 1.95-1.15 (10H, m, H-6$_B$+CH$_2$-7+C$\underline{H}_B$CON+3×CH$_2$), 1.06 and 1.03 (6H, 2t, J=7.1, N(CH$_2$C$\underline{H}_3$)$_2$), 1.04 (3H, s, CH$_3$), 0.92 (3H, s, CH$_3$).

EXAMPLE 20

Preparation of (−)-cephalotaxyl (2'S)-2-(but-2-enyl) oxycarbonylmethyl-6,6-dimethyl-2-tetrahydropyrane carboxylate or 4'-(but-2-enyl)-4'-demethyl-anhydro-epi-homoharringtonine

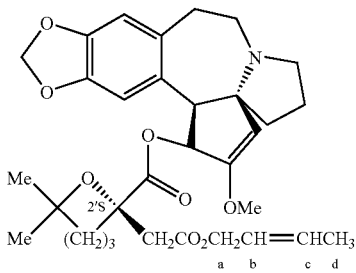

1°) Method A

To a stirred mixture of 4'-demethyl-anhydro-epi-homoharringtonine (60 mg, 0.12 mmol) resulting from Example 1 in dry dichloromethane (0.35 ml) was added at 0° C. triethylamine (dried over potassium hydroxide) (17 µl, 0.12 mmol) and 2,4,6-trichlorobenzoyl chloride (19 µl, 0.12 mmol) over a period of 10 minutes. After stirring at ambient temperature for 2.5 hours a solution of 4-dimethylaminopyridine (29 mg, 0.14 mmol) and crotyl alcohol (17 µl, 0.24 mmol) in dry dichloromethane (0.19 ml) was added. After stirring at ambient temperature for 72 hours, the reaction mixture was diluted with dichloromethane (5 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product was purified by column chromatography (silica 15-40 µm (1 g), dichloromethane then dichloromethane/methanol, 99:1 to 97:3) to provide the expected compound (36 mg, 55%). The product thus obtained showed the following characteristics:

$^1$H NMR 400 MHz (CDCl$_3$) (δ ppm, J Hz): 6.61 (1H, s, H-17*), 6.57 (1H, s, H-14*), 5.85 and 5.81 (2H, 2d, J$_{AB}$=1.4, OCH$_2$O), 5.83 (1H, d, J$_{3-2}$=9.6, H-3), 5.75 (1H, dq, J$_{c-b}$=15.2, J$_{c-d}$=6.5, H-c), 5.55 (1H, m, J$_{b-c}$=15.3, H-b), 5.02 (1H, s, H-1), 4.46 and 4.38 (2H, 2dd, J$_{AB}$=12.3, J$_{a-b}$=6.5, CH$_2$-a), 3.77 (1H, d, J$_{4-3}$=9.7, H-4), 3.65 (3H, s, OCH$_3$), 3.23 (1H, m, H-11β), 3.09 (1H, m, H-8α), 2.95 (1H, m, H-10α), 2.61 (2H, m, H-8β+H-10β), 2.40 (1H, dd, J$_{AB}$=14.2, J=6.6, H-11α), 2.13 and 1.78 (2H, 2d, J$_{AB}$=14.3, C$\underline{H}_2$CO$_2$), 2.01 (1H, m, H-6$_A$), 1.90 (1H, m, H-6$_B$), 1.76 (2H, m, CH$_2$-7), 1.71 (3H, dd, J$_{d-c}$=6.5, J$_{d-b}$=1.1, CH$_{3-d}$),1.55-1.2 (6H, m, 3×CH$_2$), 1.11 (3H, s, CH$_3$), 1.01 (3H, s, CH$_3$).

2°) Method B

Sodium hydride 60% (10 mg, 0.228 mmol) was added to a solution of anhydro-epi-homoharringtonine (100 mg, 0.18 mmol) resulting from Example 1 in crotyl alcohol (1 ml) and the resulting mixture-was stirred at ambient temperature for 72 hours. After neutralization by addition of hydrochloric acid 1N, dilution with water (5 ml) and saturation with sodium chloride, the resulting aqueous layer was extracted with dichloromethane (3×5 ml). The combined organic layers were dried over magnesium sulfate and evaporated to dryness. The resulting crude product was purified by column chromatography (silica 15-40 µm (2 g), dichloromethane then dichloromethane/methanol, 99:1) to provide, the expected product (66 mg, 62%). The product thus obtained showed identical characteristics to this obtained with method A.

EXAMPLE 21

Preparation of (−)-cephalotaxyl (2'R)-2-(but-2-enyl) oxycarbonylmethyl-6,6-dimethyl-2-tetrahydropyrane carboxylate or 4'-(but-2-enyl)-4'-demethyl-anhydro-homoharringtonine

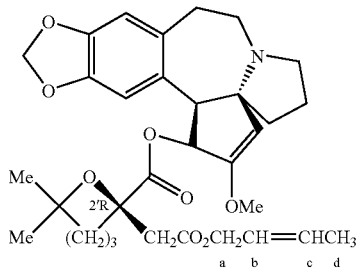

Sodium hydride 60% (21.9 mg, 0.9 mmol) was added to a solution of anhydro-homoharringtonine (400 mg, 0.767 mmol) in 3-methyl-2-butenol (4 ml) and the resulting mixture was stirred at ambient temperature for 36 hours under argon. After dilution with water (50 ml) the aqueous layer was extracted with dichloromethane (3×20 ml). The combined organic layers were diluted with dichloromethane (150 ml), washed with water (50 ml), dried over magnesium sulfate and evaporated to dryness (350 mg crude, 81%). The crude product thus obtained was purified by column chromatography (silica 15-40 µm (5 g), dichloromethane then dichloromethane/methanol, 95:5) to provide the expected product (105 mg, 24.5%). The product thus obtained showed the following characteristics:

$^1$H NMR 400 MHz (CDCl$_3$) (δ ppm, J Hz): 6.61 (1H, s, H-17*), 6.57 (1H, s, H-14*), 5.91 (1H, d, J$_{3-2}$=9.4, H-3), 5.86 and 5.78 (2H, 2d, JAB=1.4, OCH$_2$O), 5.72 (1H, m, H-c), 5.55 (1H, m, H-b), 5.03 (1H, s, H-1), 4.43 (2H, m, CH$_2$-a), 3.78 (1H, d, J$_{4-3}$=9.7, H-4), 3.69 (3H, s, OCH$_3$), 3.11 (2H, m, H-11β+H-8α), 2.94 (1H, m, H-10α), 2.59 (2H, H-8β+H-10β), 2.36 (1H, dd, J$_{AB}$=14.1, J=6.9, H-11α), 2.13 and 1.60 (2H, 2d, J$_{AB}$=14.43, C$\underline{H}_2$CO$_2$), 2.0 (1H, m, H-6$_A$), 1.89 (1H, m, H-6$_B$), 1.75 (2H, m, CH$_2$-7), 1.71 (3H, dd, J$_{d-c}$=5.5, J$_{d-b}$=1.1, CH$_3$-d), 1.7-1.2 (6H, m, 3×CH$_2$), 1.10 (3H, s, CH$_3$), 1.04 (3H, s, CH$_3$).

EXAMPLE 22

Preparation of 4'-demethyl-epi-homoharringtonine from epi-homoharringtonine

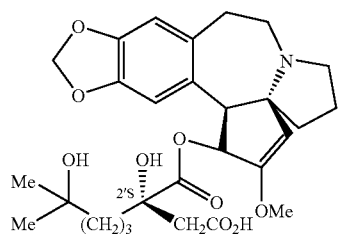

To a stirred solution of epi-homoharringtonine (266 mg, 0.488 mmol) in methanol (6.7 ml) was added lithium hydroxide (119 mg, 0.488 mmol) and water (2.2 ml). After stirring 5 hours at ambient temperature 1N hydrochloric acid was added to pH 7 and ethanol was evaporated under reduced pressure. After addition of dichloromethane (10 ml), the residual aqueous layer is exhausted by triturition with magnesium sulfate. The solid removed by filtration was washed with dichloromethane (4×2 ml) and the combined organic layers were dried over magnesium sulfate and evaporated to dryness to provide the expected compound (128 mg crude, 49%). The crude product thus obtained showed the following characteristics:

$^1$H NMR 400 MHz (DMSA-d$_6$) (δ ppm, J Hz): 6.64 (1H, s, H-17*), 6.57 (1H, s, H-14*), 5.90 (2H, s, OCH$_2$O), 5.75 (1H, d, J$_{3-4}$=9.5, H-3), 5.11 (1H, s, H-1), 3.95 (1H, s, 2'-OH), 3.78 (1H, d, J$_{4-3}$=9.7, H-4), 3.58 (3H, s, OCH$_3$), 3.06 (1H, m, H-11β), 2.81 (1H, m, H-8α), 2.68 (1H, m, H-10α), 2.52 (2H, m, H-8β+H-10β), 2.33 (1H, dd, J$_{AB}$=13.4, J=6.3, H-11α), 2.0 (2H, m, C$\underline{H}_2$CO$_2$), 1.9-0.6 (10H, m, CH$_2$-6+CH$_2$-7+3×CH$_2$), 0.99 (3H, s, CH$_3$), 0.97 (3H, s, CH$_3$).

EXAMPLE 23

Preparation of 4'-demethyl-homoharringtonine from homoharringtonine

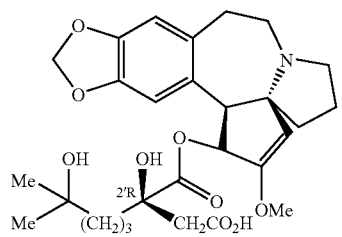

To a stirred solution of homoharringtonine (60 mg, 0.11 mmol) in methanol (1.5 ml) was added lithium hydroxide (27 mg, 1.1 mmol) and water (0.5 ml). After stirring 15 hours at ambient temperature 1N hydrochloric acid was added to pH 7-8 and ethanol was evaporated under reduced pressure. After addition of dichloromethane (5 ml), the residual aqueous layer is exhausted by triturition with magnesium sulfate. The solid removed by filtration was washed with dichloromethane (4×2 ml) and the combined organic layers were dried over magnesium sulfate and evaporated to dryness to provide the expected compound (28 mg crude, 48%). The crude product thus obtained showed the following characteristics:

IR (film) (cm$^{-1}$): 3600–2800 (CO$_2$H, OH), 1738 (CO$_2$), 1657 (C=C—O), 1505 (Ar), 1223 (C—O), 1166 (C—O), 1080 (C—O), 1041 (C—O), 912. $^1$H NMR 400 MHz (DMSO-d$_6$) (δ ppm, J Hz): 6.63 (1H, s, H-17*), 6.54 (1H, s, H-14*), 5.89+5.86 (2H, 2s, OCH$_2$O), 5.70 (1H, d, J$_{3-4}$=9.6, H-3), 5.13 (1H, s, H-1), 4.02 (1H, s, 2'-OH), 3.77 (1H, d, J$_{4-3}$=9.6, H-4), 3.59 (3H, s, OCH$_3$), 3.04 (1H, m, H-11β), 2.81 (1H, td, J=8.7 and 3.6, H-8α), 2.69 (1H, m, H-10α), 2.52 (2H, m, H-8β+H-10β), 2.33 (1H, dd, J$_{AB}$=14.0, J=7.0, H-11α), 1.86 (1H, m, H-6$_A$), 1.81 (1H, m, H-6$_B$), 1.68–1.57 (4H, 2m, CH$_2$-7+C$\underline{H}_2$CO$_2$), 1.16 (6H, m, 3×CH$_2$), 1.02 (3H, s, CH$_3$), 1.01 (3H, s, CH$_3$).

EXAMPLE 24

Preparation of (2'S)-4'-ethyl-4'-demethyl-epi-homo-harringtonine

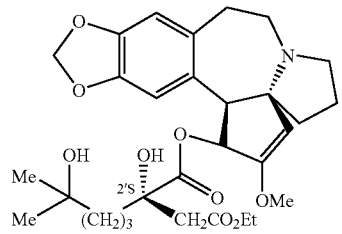

1°) Method A

To a stirred solution of 4'-ethyl-4'-demethyl-anhydro-epi-homoharringtonine (59 mg, 0.109 mmol) resulting from Example 3 in dry dichloromethane (0.3 ml) under nitrogen was added at −10° C. a commercial solution of hydrobromic acid in acetic acid (0.195 ml, 0.98 mmol, HBr 30% w/w) .After stirring at −10° C. for 3 hours, was added water (2.8 ml) and the temperature was raised to 20° C. After stirring at 20° C. for 3 hours, was added a sodium carbonate solution (0.76 M, 6 ml) up to pH 8. The resulting aqueous layer, after saturation with sodium chloride, was extracted with dichloromethane (3×10 ml) and the combined organic layers were dried over magnesium sulfate and evaporated to dryness to provide the expected compound (46 mg crude, 76%). The crude product thus obtained showed the following characteristics:

$^1$H NMR 400 MHz (CDCl$_3$) (δ ppm, J Hz): 6.64 (1H, s, H-17*), 6.59 (1H, s, H-14*), 5.95 and 5.85 (2H, 2d, J$_{AB}$=1.3, OCH$_2$O), 5.94 (1H, d, J$_{3-4}$=9.3, H-3), 5.03 (1H, s, H-1), 4.11 (2H, m, OC$\underline{H}_2$CH$_3$), 3.78 (1H, d, J$_{4-3}$=9.8, H-4), 3.65 (3H, s, OCH$_3$), 3.52 (1H, s, 2'-OH), 3.09 (2H, m, H-11β+H-8α), 2.93 (1H, m, H-10α), 2.59 and 2.51 (2H, 2d, J$_{AB}$=16.6, C$\underline{H}_2$CO$_2$), 2.57 (2H, m, H-8β+H-10β), 2.38 (1H, dd, J$_{AB}$=14.2, J=6.8, H-11α), 2.02 (1H, m, H-6$_A$), 1.89 (1H, m, H-6$_B$), 1.71 (2H, m, CH$_2$-7), 1.5-0.6 (6H, m, 3×CH$_2$), 1.24 (3H, t, J=7.2, OCH$_2$CH$_3$), 1.16 (3H, s, C$\underline{H}_3$), 1.15 (3H, s, CH$_3$).

2°) Method B

To a stirred mixture of 4'-demethyl-epi-homoharringtonine (40 mg, 0.075 mmol) resulting from Example 22 in dry dichloromethane (0.26 ml) was added at 0° C. triethylamine (dried over potassium hydroxide),(10 µl, 0.075 mmol) and 2,4,6-trichlorobenzoyl chloride (12 µl, 0.075 mmol) over a period of 10 minutes. After stirring at ambient temperature for 2.5 hours a solution of 4-dimethylaminopyridine (18.4 mg, 0.15 mmol) and ethanol (8 µl, 0.138 mmol) in dry dichloromethane (0.16 ml) was added. After stirring at ambient temperature for 15 hours, the reaction mixture was diluted with dichloromethane (10 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product was purified by column chromatography (silica 15-40 □m (1 g), dichloromethane then dichloromethane/methanol, 99:1 to 98:2) to provide the expected compound (11 mg, 26%). The product thus obtained showed identical characteristics to this obtained with method A.

EXAMPLE 25

Preparation of (2'R)-4'-ethyl-4'-demethyl-homoharringtonine

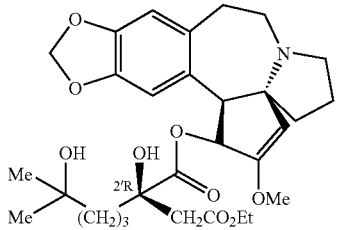

1°) Method A

To a stirred solution of 4'-ethyl-4'-demethyl-anhydro-homoharringtonine (220 mg, 0.406 mmol) resulting from Example 4 in dry dichloromethane (1.1 ml) under nitrogen was added at −10° C. a commercial solution of hydrobromic acid in acetic acid (0.728 ml, 3.6 mmol, HBr 30% w/w). After stirring at −10° C. for 3 hours, was added water (10 ml) and the temperature was raised to 20° C. After stirring at 20° C. for 3 hours, was added a sodium carbonate solution (0.76 M, 31.5 ml) up to pH 8-9. The resulting aqueous layer, after saturation with sodium chloride, was extracted with dichloromethane (3×20 ml) and the combined organic layers were dried over magnesium sulfate and evaporated to dryness. The resulting crude product was purified by column chromatography (silica 15-40 µm (8 g), dichloromethane then dichloromethane/methanol, 99:1 to 98:2) to provide the expected compound (125 mg, 55%). The product thus obtained showed the following characteristics:

HRMS calcd for C$_{30}$H$_{42}$NO$_9$ [M+H]$^+$ 560.2860, obsd 560.2863

IR (film) (cm$^{-1}$): 3516 (OH), 3427 (OH), 1741 (CO$_2$), 1656 (C=C—O), 1504 (Ar), 1224 (C—O), 1183 (C—O), 1114 (C—O), 1083 (C—O), 1035 (C—O), 911. $^1$H NMR 400 MHz (CDCl$_3$) (δ ppm, J Hz): 6.62 (1H, s, H-17*), 6.55 (1H, s, H-14*), 5.98 (1H, d, J$_{3-4}$=9.7, H-3), 5.86 (2H, m, OCH$_2$O), 5.05 (1H, s, H-1), 4.02 (2H, m, OC$\underline{H}_2$CH$_3$), 3.78 (1H, d, J$_{4-3}$=9.7, H-4), 3.68 (3H, s, OCH$_3$), 3.53 (1H, s, 2'-OH), 3.10 (2H, m, H-11β+H-8α), 2.96 (1H, m, H-10α), 2.60 (2H, m, H-8β+H-10β), 2.38 (1H, m, H-11α), 2.24 and 1.90 (2H, 2d, J$_{AB}$=16.2, C$\underline{H}_2$CO$_2$), 2.02 (1H, m, H-6$_A$), 1.90

(1H, m, H-6$_B$), 1.76 (2H, m, CH$_2$-7), 1.5-1.15 (6H, m, 3×CH$_2$),1.21 (3H, t, J=7.2, OCH$_2$CH$_3$), 1.19 (6H, 2s, 2×CH3),

2°) Method B

Sodium hydride 60% (2.4 mg, 0.1 mmol) was added to a solution of homoharringtonine (300 mg, 0.55 mmol) in dry ethanol (30 ml) and the resulting mixture was stirred at ambient temperature for 27 hours. After addition of water (10 ml) the resulting aqueous layer was saturated with sodium chloride and extracted with dichloromethane (3×20 ml). The combined organic layers were dried over magnesium sulfate and evaporated to dryness. The crude product thus obtained was purified by phase-reversed chromatography (octadecylsilane 12 μm (65 g), buffer NH$_4$Cl—HCl/methanol, 82:18). After removal of methanol in vacuo the resulting aqueous layer was alkalinized to pH 8-9 and extracted with dichloromethane (3×50 ml). The combined organic layers were dried over magnesium sulfate and evaporated to dryness to provide the expected compound (298 mg; 97%). The product thus obtained showed identical characteristics to this obtained with method A.

EXAMPLE 26

Preparation of (2'S)-4-isopropyl-4'-demethyl-epi-homoharringtonine

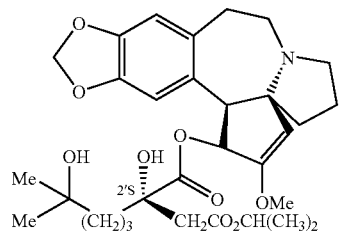

To a stirred solution of 4'-isopropyl-4'-demethyl-anhydro-epi-homoharringtonine (46 mg, 0.083 mmol) resulting from Example 5 in dry dichloromethane (0.23 ml) under nitrogen was added at –10° C. a commercial solution of hydrobromic acid in acetic acid (0.148 ml, 0.745 mmol, HBr 30% w/w). After stirring at –10° C. for 3 hours, was added water (2.2 ml) and the temperature was raised to 20° C. After stirring at 20° C. for 3 hours, was added a sodium carbonate solution (0.76 M, 4 ml) up to pH 8. The resulting aqueous layer, after saturation with sodium chloride, was extracted with dichloromethane (3×5 ml) and the combined organic layers were dried over magnesium sulfate and evaporated to dryness to provide the expected compound (30 mg crude, 64%). The crude product thus obtained showed the following characteristics:

$^1$H NMR 400 MHz (CDCl$_3$) (δ ppm, J Hz): 6.64 (1H, s, H-17*), 6.59 (1H, s, H-14*), 5.94 and 5.85 (2H, 2d, J$_{AB}$=1.3, OCH$_2$O), 5.93 (1H, d, J$_{3-4}$=9.8, H-3), 5.03 (1H, s, H-1), 4.98 (1H, m, J=6.2, OCH(CH$_3$)$_2$), 3.78 (1H, d, J$_{4-3}$=9.7, H-4), 3.65 (3H, s, OCH$_3$), 3.54 (1H, s, 2'-OH), 3.09 (2H, m, H-11β+H-8α), 2.94 (1H, m, H-10α), 2.57 and 2.49 (2H, 2d, J$_{AB}$=16.6, CH$_2$CO$_2$), 2.56 (2H, m, H-8β+H-10β), 2.38 (1H, dd, J$_{AB}$=14.0, J=7.0, H-11α), 2.02 (1H, m, H-6$_A$), 1.89 (1H, m, H-6$_B$), 1.71 (2H, m, CH$_2$-7), 1.5-0.6 (6H, m, 3×CH$_2$), 1.22 and 1.21 (6H, 2d, J=6.2, OCH(CH$_3$)$_2$), 1.16 (3H, s, CH$_3$), 1.15 (3H, s, CH$_3$).

EXAMPLE 27

Preparation of (2'R)-4'-isopropyl-4'-demethyl-homo-harringtonine

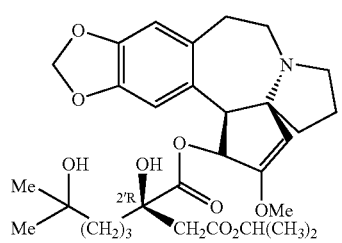

1°) Method A

To a stirred solution of 4'-isopropyl-4'-demethyl-anhydro-homoharringtonine (220 mg, 0.36 mmol) resulting from Example 6 in dry dichloromethane (1 ml) under nitrogen was added at –10° C. a commercial solution of hydrobromic acid in acetic acid (0.64 ml, 3.24 mmol, HBr 30% w/w). After stirring at –10° C. for 3 hours, was added water (9.5 ml) and the temperature was raised to 20° C. After stirring at 20° C. for 3 hours, was added a sodium carbonate solution (0.76 M, 17.4 ml) up to pH 8-9. The resulting aqueous layer, after saturation with sodium chloride, was extracted with dichloromethane (3×20 ml) and the combined organic layers were dried over magnesium sulfate and evaporated to dryness. The resulting crude product was purified by column chromatography (silica 15-40, μm (6 g), dichloromethane then dichloromethane/methanol, 99:1 to 97:3) to provide the expected compound (103 mg, 50%). The product thus obtained showed the following characteristics:

HRMS calcd for C31H$_{44}$NO$_9$ [M+H]$^+$ 574.3016, obsd 574.3012

IR (film) (cm$^{-1}$): 3519 (OH), 3430 (OH), 1735 (CO$_2$), 1655 (C=C—O), 1504 (Ar), 1224 (C—O), 1182 (C—O), 1109 (C—O), 1039 (C—O), 910. $^1$H NMR 400 MHz (CDCl$_3$) (δ ppm, J Hz): 6.63,(1H, s, H-17*), 6.56 (1H, s, H-14*), 5.96 (1H, d, J$_{3-4}$=9.8, H-3), 5.86 (2H, s, OCH$_2$O), 5.05 (1H, s, H-1), 4.88 (1H, m, J=6.2, OCH(CH$_3$)$_2$), 3.78 (1H, d, J$_{4-3}$=9.8, H-4), 3.68 (3H, s, OCH$_3$), 3.54 (1H, s, 2'-OH), 3.10 (2H, m, H-11β+H-8α), 2.95 (1H, m, H-10α), 2.60 (2H, m, H-8β+H-10β), 2.38 (1H, dd, J$_{AB}$=14.0, J=6.7, H-11α), 2.19 and 1.87 (2H, 2d, J$_{AB}$=16.0, CH$_2$CO$_2$), 2.02 (1H, m, H-6$_A$), 1.91 (1H, m, H-6$_B$), 1.76 (2H, m, CH$_2$-7), 1.5-1.16 (6H, m, 3×CH$_2$), 1.18 (12H, m, OCH(CH$_3$)2+2×CH$_3$).

2°) Method B

Sodium hydride 60% (13 mg, 0.325 mmol) was added (in 2 parts, at t=0 and t=16 hours) to a solution of homoharringtonine (440 mg, 0.807 mmol) in isopropanol (6 ml) with stirring at ambient temperature under argon. 4 hours after the last addition the mixture was adjusted to pH 1.9 by addition of hydrochloric acid 0.1N (157 ml) and the aqueous layer was washed with ether (3×8 ml). The resulting aqueous layer was alkalinized with ammonia 25% (0.3 ml) and was extracted with dichloromethane (8×8 ml). The combined organic layers were dried over magnesium sulfate and evaporated to dryness (311 mg crude, 67%). The crude product thus obtained was purified by phase-reversed chromatography (octadecylsilane 12 μm (100 g), buffer pH 3/methanol, 61:39). After removal of methanol in vacuo the resulting aqueous layer was alkalinized to pH 10 with ammonia 25% and extracted with dichloromethane (6×8 ml). The combined organic layers were dried over magnesium sulfate and evaporated to dryness to provide the expected compound (143 mg; 31%). The product. thus obtained showed identical characteristics to this obtained with method A.

EXAMPLE 28

Preparation of (2'S)-4'-benzyl-4'-demethyl-epi-homoharringtonine

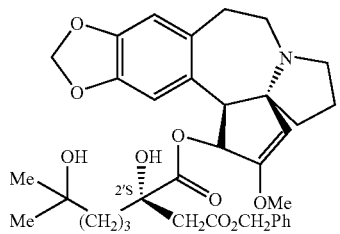

To a stirred solution of 4'-benzyl-4'-demethyl-anhydro-epi-homoharringtonine (28 mg, 0.046 mmol) resulting from Example 7 in dry dichloromethane (0.14 ml) under nitrogen was added at −10° C. a commercial solution of hydrobromic acid in acetic acid (83 µl, 0.417 mmol, HBr 30% w/w). After stirring at −10° C. for 3 hours, was added water (2 ml) and the temperature was raised to 20° C. After stirring at 20° C. for 3 hours, was added a sodium carbonate solution (0.76 M, 4 ml) up to pH 8. The resulting aqueous layer, after saturation with sodium chloride, was extracted with dichloromethane (3×3 ml) and the combined organic layers were dried over magnesium sulfate and evaporated to dryness to provide the expected compound (30 mg crude, 100%). The crude product thus obtained showed the following characteristics:

$^1$H NMR 400 MHz (CDCl$_3$) (δ ppm, J Hz): 7.34 (5H, m, Ph), 6.64 (1H, s, H-17), 6.60 (1H, s, H-14), 5.90 (3H, m, OCH$_2$O+H-3), 5.12 and 5.07 (2H, 2d, J$_{AB}$=12.4, OCH$_2$Ph), 5.01 (1H, s, H-1), 3.78 (1H, d, H-4), 3.60 (3H, s, OCH$_3$), 3.13 (2H, m, H-11β+H-8α), 2.96 (1H, m, H-10α), 2.66 and 2.57 (2H, 2d, J$_{AB}$=16.7, CH$_2$CO$_2$), 2.60 (2H, m, H-8β+H-10β), 2.40 (1H, m, H-11α), 2.04 (1H, m, H-6$_A$), 1.92 (1H, m, H-6$_B$), 1.78 (2H, m, CH$_2$-7), 1.6-0.8 (6H, m, 3×CH$_2$), 1.16 (3H, s, CH$_3$), 1.15 (3H, s, CH$_3$).

EXAMPLE 29

Preparation of (2'R)-4'-benzyl-4'-demethyl-homoharringtonine

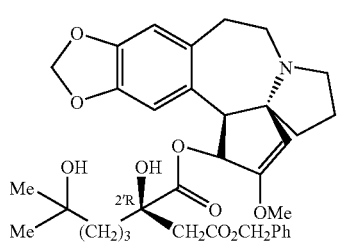

1°) Method A

To a stirred solution of 4'-benzyl-4'-demethyl-anhydro-homoharringtonine (261 mg, 0.432 mmol) resulting from Example-8 in dry dichloromethane (1.3 ml) under nitrogen was added at −10° C. a commercial solution of hydrobromic acid in acetic acid (0.775 ml, 3.89 mmol, HBr 30% w/w). After stirring at −10° C. for 3 hours, was added water (18.6 ml) and the temperature was raised to 20° C. After stirring at 20° C. for 3 hours, was added a sodium carbonate solution (0.76 M, 37 ml) up to pH 8. The resulting aqueous layer, after saturation with sodium chloride, was extracted with dichloromethane (3×20 ml) and the combined organic layers were dried over magnesium sulfate and evaporated to dryness. The resulting crude product was purified by column chromatography (silica 15-40 µm (8 g), dichloromethane then dichloromethane/methanol, 99:1 to 95:5) to provide the expected compound (80 mg, 30%). The crude product thus obtained showed the following characteristics:

IR (film) (cm$^{-1}$): 3520 (OH), 3401 (OH), 1744 (CO2), 1655 (C═C—O), 1504 (Ar), 1224 (C—O), 1173 (C—O), 1082 (C—O), 1037,(C—O), 910. $^1$H NMR 400 MHz (CDCl$_3$) (δ ppm, J Hz): 7.33 (5H, m, Ph), 6.62 (1H, s, H-17), 6.44 (1H, s, H-14), 5.96 (1H, d, J$_{3-4}$=9.7, H-3), 5.77 and 5.65 (2H, 2s, OCH$_2$O), 5.09 and 4.94 (2H, 2d, J$_{AB}$=12.4, OCH$_2$Ph), 5.05 (1H, s, H-1), 3.70 (1H, d, J$_{4-3}$=10, H-4), 3.68 (3H, s, OCH$_3$), 3.52 (1H, s, 2'-OH), 3.10 (2H, m, H-11β+H-8α), 2.93 (1H, m, H-10α), 2.59 (2H, m, H-8β+H-10β), 2.40 (1H, dd, J$_{AB}$=14, J=6.7, H-11α), 2.31 and 1.92 (2H, 2d, J$_{AB}$=16.3, CH$_2$CO$_2$), 2.0,(1H, m, H-6$_A$), 1.90 (1H, m, H-6$_B$), 1.75 (2H, m, CH$_2$-7), 1.6-1.1 (6H, m, 3×CH$_2$), 1.25 (1H, s, OH), 1.19 (3H, s, CH$_3$), 1.18 (3H, s, CH$_3$).

2)° Method B

Sodium hydride 60% (10 mg, 0.275 mmol) was added to a solution of homoharringtonine (300 mg, 0.55 mmol) in benzylic alcool (4 ml) and the resulting mixture was stirred at ambient temperature for 1.5 hours under argon. After adjusting to pH 2.5 by addition of hydrochloric acid 0.1N (15 ml) the aqueous layer was washed with ether (3×15 ml). The resulting aqueous layer was alkalinized with ammonia 25% (1.5 ml) and was extracted with dichloromethane (6×15 ml). The combined organic layers were dried over magnesium sulfate and evaporated to dryness. The crude product thus obtained was purified by phase-reversed chromatography (octadecylsilane 12 µm (100 g), buffer pH 3/methanol, 47:53). After removal of methanol in vacuo the resulting aqueous layer was alkalinized to pH 9 with ammonia 25% and extracted with dichloromethane (3×5 ml). The combined organic layers were dried over magnesium sulfate and evaporated to dryness to provide the expected compound (154 mg; 45%). The product thus obtained showed the following characteristics:

EXAMPLE 30

Preparation of (2'R)-4'-methylthio-4'-demethoxy-homoharringtonine

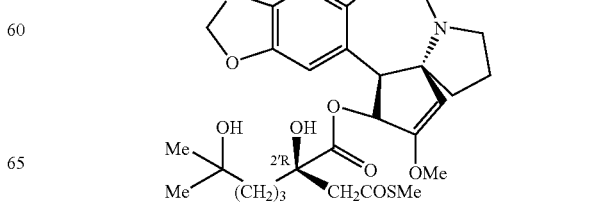

To a stirred solution of 4'-methylthio-4'-demethoxy-anhydro-homoharringtonine (209 mg, 0.384 mmol) resulting from Example 9 in dry dichloromethane (1 ml) under nitrogen was added at −10° C. a commercial solution of hydrobromic acid in acetic acid (0.608 ml, 3.46 mmol, HBr 30% w/w). After stirring at −10° C. for 3 hours, was added water (12.2 ml) and the temperature was raised to 20° C. After stirring at 20° C. for 3 hours, was added a sodium carbonate solution (0.76 M, 29 ml) up to pH 8-9. The resulting aqueous layer, after saturation with sodium chloride, was extracted with dichloromethane (3×20 ml) and the combined organic layers were dried over magnesium sulfate and evaporated to dryness. The resulting crude product was purified by reversed-phase column chromatography (n-octadecylsilane, 15 μm (20 g), methanol/buffer pH 3, 32:68) and the retained fractions were combined. After removal of methanol in vacuo the residual aqueous layer (250 ml) was adjusted to pH 8, extracted with dichloromethane (3×80 ml) and the combined organic layers were dried over magnesium sulfate and evaporated to dryness to provide the expected compound (100 mg, 46.5%). The crude product thus obtained showed the following characteristics:

HRMS calcd for $C_{29}H_{40}NO_8S$ $[M+H]^+$ 562.2475, obsd 562.2477

IR (film) ($cm^{-1}$): 3513 (OH), 3369 (OH), 1744 (CO2), 1688 (COS), 1655 (C=C—O), 1503 (Ar), 1223 (C—O), 1150 (C—O), 1081 (C—O), 1035 (C—O), 911.

$^1$H NMR 400 MHz (CDCl$_3$) (δ ppm, J Hz): 6.62 (1H, s, H-17*), 6.54 (1H, s, H-14*), 6.01 (1H, d, $J_{3-4}$=9.7, H-3), 5.87 (2H, s, OCH$_2$O), 5.05 (1H, s, H-1), 3.78 (1H, d, $J_{4-3}$=9.6, H-4), 3.68 (3H, s, OCH$_3$), 3.42 (1H, s, 2'-OH), 3.09 (2H, m, H-11β+H-8α), 2.94 (1H, m, H-10α), 2.59 (2H, m, H-8β+H-10β), 2.50 and 2.03 (2H, 2d, $J_{AB}$=15.8, C$\underline{H}_2$COS), 2.40 (1H, m, H-11α), 2.23 (3H, s, SCH$_3$), 2.03 (1H, m, H-6$_A$), 1.91 (1H, m, H-6$_B$), 1.76 (2H, m, CH$_2$-7), 1.6-1.2 (6H, m, 3×CH$_2$),1.19 (3H, s, CH$_3$),1.18 (3H, s, CH$_3$).

EXAMPLE 31

Preparation of (2'S)-4'-ethylthio-4'-demethoxy-epi-homoharringtonine

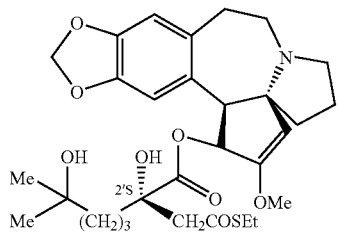

To a stirred solution of 4'-ethylthio-4'-demethoxy-anhydro-epi-homoharringtonine (18 mg, 0.032 mmol) resulting from Example 10 in dry dichloromethane (90 □l) under nitrogen was added at −10° C. a commercial solution of hydrobromic acid in acetic acid (58 μl, 0.29 mmol, HBr 30% w/w). After stirring at −10° C. for 3 hours, was added water (2 ml) and the temperature was raised to 20° C. After stirring at 20° C. for 3 hours, was added a sodium carbonate solution (0.76 M, 2 ml) up to pH 8. The resulting aqueous layer, after saturation with sodium chloride, was extracted with dichloromethane (3×2 ml) and the combined organic layers were dried over magnesium sulfate and evaporated to dryness to provide the expected compound (18 mg crude, 76%). The crude product thus obtained showed the following characteristics:

$^1$H NMR 400 MHz (CDCl$_3$) (δ ppm, J Hz): 6.66 (1H, s, H-17*), 6.59 (1H, s, H-14*), 5.95 and 5.85 (2H, 2d, $J_{AB}$=1.2, OCH$_2$O), 5.95 (1H, d, $J_{3-4}$=9.7, H-3), 5.03 (1H, s, H-1), 3.78 (1H, d, $J_{4-3}$=9.7, H-4), 3.66 (3H, s, OCH$_3$), 3.43 (1H, s, 2'-OH), 3.12 (2H, m, H-11β+H-8α), 2.94 (1H, m, H-10α), 2.89 (2H, m, SC$\underline{H}_2$CH$_3$), 2.79 (2H, m, C$\underline{H}_2$COS), 2.58 (2H, m, H-8β+H-10β), 2.40 (1H, dd, $J_{AB}$=14.2, J=6.9, H-11α), 2.02 (1H, m, H-6$_A$), 1.90 (1H, m, H-6$_B$), 1.76 (2H, m, CH$_2$-7), 1.5-0.6 (6H, m, 3×CH$_2$), 1.24 (3H, t, J=7.4, SCH$_2$CH$_3$), 1.16 (3H, s, C$\underline{H}_3$),1.15 (3H, s, CH$_3$).

EXAMPLE 32

Preparation of (2'R)-4'-ethylthio-4'-demethoxy-homoharringtonine

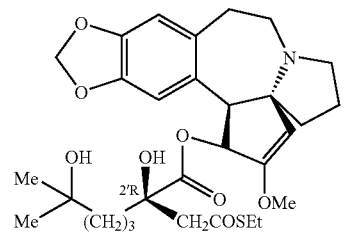

To a stirred solution of 4'-ethylthio-4'-demethoxy-anhydro-homoharringtonine (251 mg, 0.45 mmol) resulting from Example 11 in dry dichloromethane (1.1 ml) under nitrogen was added at −10° C. a commercial solution of hydrobromic acid in acetic acid (0.803 ml, 4.05 mmol, HBr 30% w/w). After stirring at −10° C. for 3 hours, was added water (14.6 ml) and the temperature was raised to 20° C. After stirring at 20° C. for 3 hours, was added a sodium carbonate solution (0.76 M, 35.9 ml) up to pH 8-9. The resulting aqueous layer, after saturation with sodium chloride, was extracted with dichloromethane (3×20 ml) and the combined organic layers were dried over magnesium sulfate and evaporated to dryness. The resulting crude product was purified by column chromatography (silica 15-40 μm (8 g), dichloromethane then dichloromethane/methanol, 99.5:0.5 to 95:5) to provide the expected compound (120 mg, 46%). The product thus obtained showed the following characteristics:

HRMS calcd for $C_{30}H_{42}NO_8S$ $[M+H]^+$ 576.2631, obsd 576.2624

IR (film) ($cm^{-1}$): 3514 (OH), 3391 (OH), 1744 (CO2), 1687 (COS), 1656 (C=C—O), 1504 (Ar), 1223 (C—O), 1159 (C—O), 1081 (C—O), 1035 (C—O), 911.

$^1$H NMR 400 MHz (CDCl$_3$) (δ ppm, J Hz): 6.63 (1H, s, H-17*), 6.54 (1H, s, H-14*), 5.99 (1H, d, $J_{3-4}$=9.8, H-3), 5.97 (2H, s, OCH$_2$O), 5.05 (1H, s, H-1), 3.78 (1H, d, $J_{4-3}$=9.8, H-4), 3.67 (3H, s, OCH$_3$), 3.43 (1H, s, 2'-OH), 3.09 (2H, m, H-11β+H-8α), 2.94 (1H, m, H-10α), 2.84 (2H, m, SC$\underline{H}_2$CH$_3$), 2.59 (2H, m, H-8β+H-10β), 2.46 and 1.98 (2H, 2d, $J_{AB}$=15.8, C$\underline{H}_2$COS), 2.38 (1H, dd, $J_{AB}$=14.0, J=6.9, H-11α), 2.02 (1H, m, H-6$_A$), 1.90 (1H, m, H-6$_B$), 1.75 (2H, m, CH$_2$-7), 1.5-1.1 (6H, m, 3×CH$_2$), 1.21 (3H, t, J=7.5, SCH$_2$C$\underline{H}_3$),1.19 (3H, s, CH$_3$),1.18 (3H, s, CH$_3$).

EXAMPLE 33

Preparation of (2'S)-4'-isopropylthio-4'-demethoxy-epi-homoharringtonine

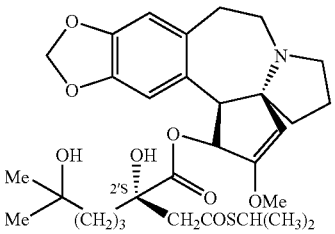

To a stirred solution of 4'-isopropylthio-4'-demethoxy-anhydro-epi-homoharringtonine (28 mg, 0.049 mmol) resulting from Example 12 in dry dichloromethane (0.14 ml) under nitrogen was added at −10° C. a commercial solution of hydrobromic acid in acetic acid (88 µl, 0.44 mmol, HBr 30% w/w). After stirring at −10° C. for 3 hours, was added water (2 ml) and the temperature was raised to 20° C. After stirring at 20° C. for 3 hours, was added a sodium carbonate solution (0.76 M, 4 ml) up to pH 8-9. The resulting aqueous layer, after saturation with sodium chloride, was extracted with dichloromethane (3×3 ml) and the combined organic layers were dried over magnesium sulfate and evaporated to dryness to provide the expected compound (19 mg crude, 66%). The crude product thus obtained showed the following characteristics:

$^1$H NMR 400 MHz (CDCl$_3$) (δ ppm, J Hz): 6.65 (1H, s, H-17), 6.59 (1H, s, H-14), 5.94 (1H, d, J3-4=10.0, H-3), 5.94 and 5.88 (2H, 2d, J$_{AB}$=1.4, OCH$_2$O), 5.03 (1H, s, H-1), 3.78 (1H, d, J$_{4-3}$=9.7, H-4), 3.66 (3H, s, OCH$_3$), 3.64 (1H, m, C$\underline{H}$(CH$_3$)$_2$), 3.41 (1H, s, OH), 3.11 (2H, m, H-11β+H-8α), 2.96 (1H, m, H-10α), 2.77 (2H, m, C$\underline{H}_2$COS), 2.59 (2H, m, H-8β+H-10β), 2.40 (1H, dd, J$_{AB}$=14.2, J=6.9, H-11α), 2.04 (1H, m, H-6$_A$), 1.90 (1H, m, H-6$_B$), 1.76 (2H, m, CH$_2$-7), 1.7-0.6 (6H, m, 3×CH$_2$), 1.29 and 1.27 (6H, 2d, J=6.8, CH(C$\underline{H}_3$)$_2$), 1.16 (3H, s, CH$_3$), 1.15 (3H, s, CH$_3$).

EXAMPLE 34

Preparation of (2'R)-4'-isopropylthio-4'-demethoxy-homoharringtonine

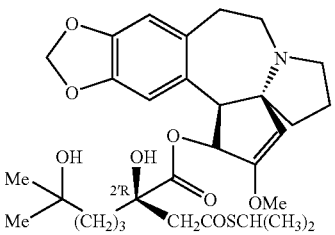

To a stirred solution of 4'-isopropylthio-4'-demethoxy-anhydro-homoharringtonine (267 mg, 0.467 mmol) resulting from Example 13 in dry dichloromethane (1.1 ml) under nitrogen was added at −10° C. a commercial solution of hydrobromic acid in acetic acid (0.839 ml, 4.2 mmol, HBr 30% w/w). After stirring at −10° C. for 3 hours, was added water (15.6 ml) and the temperature was raised to 20° C. After stirring at 20° C. for 3 hours, was added a sodium carbonate solution (0.76 M, 38.2 ml) up to pH 8-9. The resulting aqueous layer, after saturation with sodium chloride, was extracted with dichloromethane (3×20 ml) and the combined organic layers were dried over magnesium sulfate and evaporated to dryness. The resulting crude product was purified by column chromatography (silica 15-40 µm (8 g), dichloromethane then dichloromethane/methanol, 99:1) to provide the expected compound (118 mg, 43%). The product thus obtained showed the following characteristics:

HRMS calcd for C$_{31}$H$_{44}$NO$_8$S [M+H]$^+$ 590.2788, obsd 590.2789 IR (film) (cm$^{-1}$) 3521 (OH), 3385 (OH), 1743 (CO2), 1681 (COS), 1656 (C═C—O), 1504 (Ar), 1223 (C—O), 1159 (C—O), 1082 (C—O), 1039 (C—O), 910.

$^1$H NMR 400 MHz (CDCl3) (δ ppm, J Hz): 6.64 (1H, s, H-17), 6.55 (1H, s, H-14), 5.97 (1H, d, J$_{3-4}$=9.8, H-3), 5.88 (2H, s, OCH$_2$O), 5.05 (1H, s, H-1), 3.79 (1H, d, J$_{4-3}$=9.8, H-4), 3.67 (3H, s, OCH$_3$), 3.56 (1H, m, J=6.9, C$\underline{H}$(CH$_3$)$_2$), 3.44 (1H, s, 2'-OH), 3.10 (2H, m, H-11β+H-8α), 2.95 (1H, td, J=11.1 and 6.8, H-10α), 2.59 (2H, m, H-8β+H-10β), 2.40 and 1.92 (2H, 2d, J$_{AB}$=15.6, C$\underline{H}_2$COS), 2.38 (1H, dd, J$_{AB}$=13.9, J=6.7, H-11α), 2.02 (1H, m, H-6$_A$), 1.90 (1H, m, H-6$_B$), 1.76 (2H, m, CH$_2$-7), 1.6-1.1 (6H, m, 3×CH$_2$): 1.27 and 1.25 (6H, 2d, J=6.9, CH(C$\underline{H}_3$)$_2$), 1.18 (6H, 2s, 2×CH$_3$).

EXAMPLE 35

Preparation of (2'S)-4'-tert-butylthio-4'-demethoxy-epi-homoharringtonine

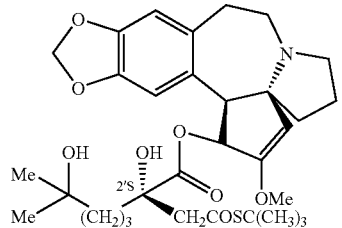

To a stirred solution of 4'-tert-butylthio-4'-demethoxy-anhydro-epi-homoharringtonine (60 mg, 0.102 mmol) resulting from Example 14 in dry dichloromethane (0.3 ml) under nitrogen was added at −10° C. a commercial solution of hydrobromic acid in acetic acid (0.183 ml, 0.44 mmol, HBr 30% w/w). After stirring at −10° C. for 3 hours, was added water (3 ml) and the temperature was raised to 20° C. After stirring at 20° C. for 3 hours, was added a sodium carbonate solution (0.76 M, 8.6 ml) up to pH 8-9. The resulting aqueous layer, after saturation with sodium chloride, was extracted with dichloromethane (3×8 ml) and the combined organic layers were dried over magnesium sulfate and evaporated to dryness to provide the expected compound (30 mg crude, 48%). The crude product thus obtained showed the following characteristics:

$^1$H NMR 400 MHz (CDCl$_3$) (δ ppm, J Hz): 6.65 (1H, s, H-17), 6.59 (1H, s, H-14), 5.96 and 5.89 (2H, 2d, J=1.3, OCH$_2$O), 5.96 (1H, d, J$_{3-4}$=9.9, H-3), 5.03 (1H, s, H-1), 3.78 (1H, d, J$_{4-3}$=9.7, H-4), 3.66 (3H, s, OCH$_3$), 3.39 (1H, s, 2'-OH), 3.13 (2H, m, H-11β+H-8α), 2.96 (1H, m, H-10α), 2.74 (2H, m, C$\underline{H}_2$COS), 2.62 (2H, m, H-8β+H-10β), 2.41 (1H, dd, J$_{AB}$=14.0, J=6.7, H-11α), 2.04 (1H, m, H-6$_A$), 1.91 (1H, m, H-6$_B$), 1.71 (2H, m, CH$_2$-7), 1.6-0.8 (6H, m, 3×CH$_2$), 1.44 (9H, s, C(CH$_3$)$_3$), 1.16 (3H, s, CH$_3$), 1.15 (3H, s, CH$_3$).

EXAMPLE 36

Preparation of (2'R)-4'-tert-butylthio-4'-demethoxy-homoharringtonine

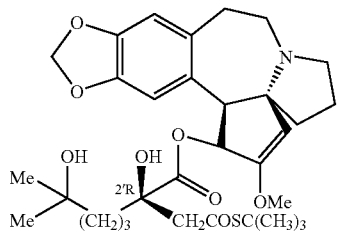

To a stirred solution of 4'-tert-butylthio-4'-demethoxy-anhydro-homoharringtonine (216 mg, 0.37 mmol) resulting from Example 15 in dry dichloromethane (1.1 ml) under nitrogen was added at −10° C. a commercial solution of hydrobromic acid in acetic acid (0.658 ml, 3.33 mmol, HBr 30% w/w). After stirring at −10° C. for 3 hours, was added water (12.6 ml) and the temperature was raised to 20° C. After stirring at 20° C. for 3 hours, was added a sodium carbonate solution (0.76 M, 31.5 ml) up to pH 8-9. The resulting aqueous layer, after saturation with sodium chloride, was extracted with dichloromethane (3×30 ml) and the combined organic layers were dried over magnesium sulfate and evaporated to dryness. The resulting crude product was purified by column chromatography (silica 15-40 □m (8 g), dichloromethane then dichloromethane/methanol, 99:1 to 95:5) to provide the expected compound (70 mg, 31.5%). The crude product thus obtained showed the following characteristics:

HRMS calcd for $C_{32}H_{46}NO_8S$ $[M+H]^+$ 604.2944, obsd 604.2940 IR (film) ($cm^{-1}$): 3514 (OH), 3369 (OH), 1744 (CO2), 1679 (COS), 1655 (C=C—O), 1504 (Ar), 1223 (C—O), 1159 (C—O), 1081 (C—O), 1035 (C—O), 910.

$^1$H NMR 400 MHz (CDCl$_3$) (δ ppm, J Hz): 6.65 (1H, s, H-17), 6.54 (1H, s, H-14), 5.96 (1H, d, $J_{3-4}$=9.7, H-3), 5.89 (2H, s, OCH$_2$O), 5.05 (1H, s, H-1), 3.78 (1H, d, $J_{4-3}$=9.9, H-4), 3.67 (3H, s, OCH$_3$), 3.46 (1H, s, 2'-OH), 3.09 (2H, m, H-11β+H-8α), 2.95 (1H, m, H-10α), 2.59 (2H, m, H-8□+H-10β), 2.32 and 1.81 (2H, 2d, $J_{AB}$=15.5, CH$_2$COS), 2.38 (1H, m, H-11α), 2.03 (1H, m, H-6$_A$), 1.91 (1H, m, H-6$_B$), 1.76 (2H, m, CH$_2$-7), 1.6-1.1 (6H, m, 3×CH$_2$), 1.42 (9H, s, C(CH$_3$)$_3$), 1.18 (3H, s, CH$_3$), 1.175 (3H, s, CH$_3$).

EXAMPLE 37

Preparation of (2'R)-4'-(but-2-enyl)-4'-demethyl-homoharringtonine

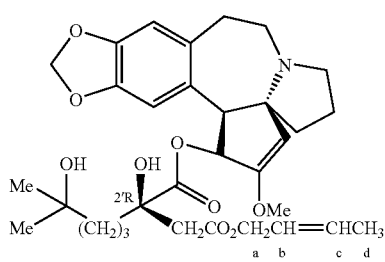

Sodium hydride 60% (15 mg, 0.366 mmol) was added to a solution of homoharringtonine (500 mg, 0.917 mmol) in crotyl alcohol (1 ml) and the resulting mixture was stirred at ambient temperature for 2.5 hours. After adjusting to pH 4 by addition of hydrochloric acid 1N the aqueous layer was flashed with ether (3×10 ml). The resulting aqueous layer was alkalinized with ammonia 25% and was extracted with dichloromethane (3×10 ml). The combined organic layers were dried over magnesium sulfate and evaporated to dryness (454 mg crude, 70%). The crude product thus obtained was purified by phase-reversed chromatography (octadecylsilane 12 μm (100 g), buffer pH 3/methanol, 55:45). After removal of methanol in vacuo the resulting aqueous layer was alkalinized to pH 9.2 with ammonia 25% and extracted with dichloromethane (6×10 ml). The combined organic layers were dried over magnesium sulfate and evaporated to dryness to provide the expected compound (122 mg; 30%). The product thus obtained showed the following characteristics:

$^1$H NMR 400 MHz (CDCl$_3$) (δ ppm, J Hz): 6.62 (1H, s, H-17*), 6.54 (1H, s, H-14*), 5.98 (1H, d, $J_{3-4}$=9.8, H-3), 5.86 and 5.85 (2H, 2d, $J_{AB}$=1.5, OCH$_2$O), 5.74 (1H, m, H-c), 5.53 (1H, m, H-b), 5.05 (1H, s, H-1), 4.46 and 4.35 (2H, 2dd, $J_{AB}$=12.3, $J_{a-b}$=6.5, CH$_2$-a), 3.77 (1H, d, $J_{4-3}$=9.8, H-4), 3.68 (3H, s, OCH$_3$), 3.55 (1H, s, 2'-OH), 3.10 (2H, m, H-11β+H-8α), 2.94 (1H, m, H-10α), 2.58 (2H, m, H-8β+H-10β), 2.38 (1H, m, H-11α), 2.25 and 1.90 (2H, 2d, $J_{AB}$32 16.4, CH$_2$CO$_2$), 2.02 (1H, m, H-6$_A$), 1.90 (1H, m, H-6$_B$), 1.76 (2H, m, CH$_2$-7), 1.72 (3H, dd, $J_{d-c}$=6.6, $J_{d-b}$=1.2, CH$_{3-d}$), 1.39 (6H, m, 3×CH$_2$), 1.18 (6H, 2s, 2×CH$_3$).

EXAMPLE 38

Preparation of (2'S)-4'-(but-2-enyl)-4'-demethyl-epi-homoharringtonine

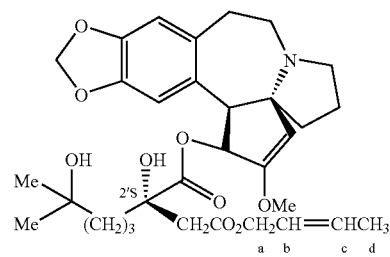

Sodium hydride 60% (15 mg, 0.366 mmol) was added to a solution of homoharringtonine (500 mg, 0.917 mmol) in crotyl alcohol (5 ml) and the resulting mixture was stirred at ambient temperature for 2 hours. After adjusting to pH 4 by addition of hydrochloric acid 1N the aqueous layer was washed with ether (3×10 ml) and diluted with water (50 ml). The resulting aqueous layer was alkalinized to pH 10.6 with ammonia 25% and was extracted with dichloromethane (5×15 ml). The combined organic layers were dried over magnesium sulfate and evaporated to dryness (456 mg crude, 78%). The crude product thus obtained was purified by phase-reversed chromatography (octadecylsilane 12 μm (100 g), buffer pH 3/methanol, 65:35). After removal of methanol in vacuo the resulting aqueous layer was alkalinized to pH 9.5 with ammonia 25% and extracted with dichloromethane (56×10 ml). The combined organic layers were dried over magnesium sulfate and evaporated to dryness to provide the expected compound (188 mg: 32%). The product thus obtained showed the following characteristics:

$^1$H NMR 400 MHz (CDCl$_3$) (δ ppm, J Hz): 6.64 (1H, s, H-17*), 6.60 (1H, s, H-14*), 5.94 (1H, d, J$_{3-4}$=9.7, H-3), 5.94 and 5.85 (2H, 2d, J$_{AB}$32 1.2, OCH$_2$O), 5.76 (1H, m, H-c), 5.54 (1H, m, H-b), 5.03 (1H, s, H-1), 4.49 (2H, m, CH$_2$-a), 3.78 (1H, d, J$_{4-3}$=9.7, H-4), 3.66 (3H, s, OCH$_3$), 3.53 (1H, s, 2'-OH), 3.10 (2H, m, H-11β+H-8α), 2.94 (1H, m, H-10α), 2.61 and 2.52 (2H, 2d, J$_{AB}$32 16.7, C$\underline{H}_2$CO$_2$), 2.59 (2H, m, H-8β+H-10β), 2.39 (1H, dd, J=14.1 and 6.8, H-11α), 2.02 (1H, m, H-6$_A$), 1.90 (1H, m, H-6$_B$), 1.72 (2H, m, CH$_2$-7) and (3H, dd, J$_{d-c}$=6.5, J$_{d-b}$=0.9, CH$_{3-d}$), 1.20 (3H, m, C$\underline{H}_2$), 1.16 (3H, s, CH$_3$), 1.15 (3H, s, CH$_3$), 1.06 (1H, m, C$\underline{H}_2$), 0.93 (1H, m, CH$_2$), 0.736 (1H, m, C$\underline{H}_2$).

EXAMPLE 39

Preparation of (2'R)-4'-(3-methyl-2-butenyl)-4'-demethyl-homoharringtonine

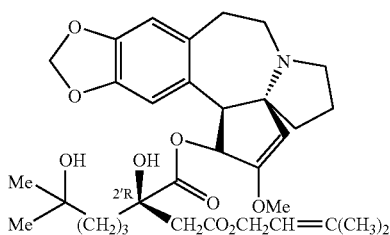

Sodium hydride 60% (29.4 mg, 0.735 mmol) was added to a solution of homoharringtonine (500 mg, 0.917 mmol) in 3-methyl-2-butenol (4 ml) and the resulting mixture was stirred at ambient temperature for 1.5 hours under argon. After adjusting to pH 2.5 by addition of hydrochloric acid 0.1N (15 ml) the aqueous layer was washed with ether (3×15 ml). The resulting aqueous layer was alkalinized with ammonia 25% (1.5 ml) and was extracted with dichloromethane (6×15 ml). The combined organic layers were dried over magnesium sulfate and evaporated to dryness (464 mg crude, 85%). The crude product thus obtained was purified by phase-reversed chromatography (octadecylsilane 12 μm (100 g), buffer pH 3/methanol, 47:53). After removal of methanol in vacuo the resulting aqueous layer was alkalinized to pH 9 with ammonia 25% and extracted with dichloromethane (3×5 ml). The combined organic layers were dried over magnesium sulfate and evaporated to dryness to provide the expected compound (266 mg; 48%). The product thus obtained showed the following characteristics:

$^1$H NMR 400 MHz (CDCl$_3$) (δ ppm, J Hz): 6.62 (1H, s, H-17), 6.54 (1H, s, H-14), 5.98 (1H, d, J$_{3-4}$=9.8, H-3), 5.86 and 5.84 (2H, 2d, J=1.5, OCH$_2$O), 5.28 (1H, m, H—C=), 5.05 (1H, s, H-1), 4.54 and 4.42 (2H, 2dd, J$_{AB}$=12.4, J=7.1, OCH$_2$), 3.77 (1H, d, J$_{4-3}$=9.8, H-4), 3.68 (3H, s, OCH$_3$), 3.54 (1H, s, 2'-OH), 3.10 (2H, m, H-11β+H-8α), 2.94 (1H, dt, J=11.5 and 7.0, H-10α), 2.58 (2H, m, H-8β+H-10β), 2.38 (1H, dd, J$_{AB}$=14.0, J=6.7, H-11α), 2.24 and 1.89 (2H, 2d, J$_{AB}$=16.4, C$\underline{H}_2$CO$_2$), 2.04 (1H, m, H-6$_A$), 1.90 (1H, m, H-6$_B$), 1.77 (2H, m, CH$_2$-7), 1.75 (3H, s, C$\underline{H}_3$—C=), 1.68 (3H, s, C$\underline{H}_3$—C=), 1.39 (6H, m, 3×CH$_2$), 1.19 (3H, s, CH$_3$), 1.18 (3H, s, CH$_3$).

EXAMPLE 40

Preparation of (2'R)-4'-(2-propenyl)-4'-demethyl-homoharringtonine

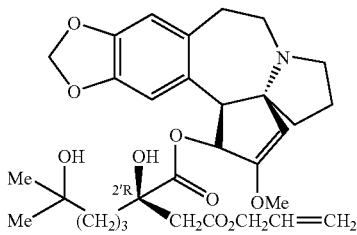

Sodium hydride 60% (29.8 mg, 0.745 mmol) was added to a solution of homoharringtonine (508 mg, 0.932 mmol) in 2-propenol (5 ml) and the resulting mixture was stirred at ambient temperature for 2 hours under argon. After adjusting to pH 2.1 by addition of hydrochloric acid 0.1N (17 ml) the aqueous layer was washed with ether (3×15 ml). The resulting aqueous layer was alkalinized with ammonia 25% (1.5 ml) and was extracted with dichloromethane (6×15 ml). The combined organic layers were dried over magnesium sulfate and evaporated to dryness (417 mg crude, 78%). The crude product thus obtained was purified by phase-reversed chromatography (octadecylsilane 12 μm (100 g), buffer pH 3/methanol, 61.5:38.5). After removal of methanol in vacuo the resulting aqueous layer was alkalinized to pH 10 with ammonia 25% and extracted with dichloromethane (5×10 ml). The combined organic layers were dried over magnesium sulfate and evaporated to dryness to provide the expected compound (289 mg; 54%). The product thus obtained showed the following characteristics:

$^1$H NMR 400 MHz (CDCl$_3$) (δ ppm, J Hz): 6.62 (1H, s, H-17), 6.54 (1H, s, H-14), 5.99 (1H, d, J$_{3-4}$=9.8, H-3), 5.87 (1H, m, HC=), 5.85 (2H, m, OCH$_2$O), 5.30 (1H, m, J=17.2, =CH$_2$), 5.22 (1H, m, J=10.4, =CH$_2$), 5.05 (1H, s, H-1), 4.53 and 4.42 (2H, 2m, J$_{AB}$=13.3, J=5.6, OCH$_2$), 3.77 (1H, d, J$_{4-3}$=9.8, H-4), 3.68 (3H, s, OCH$_3$), 3.52 (1H, s, 2'-OH), 3.10 (2H, m, H-11β+H-8α), 2.94 (1H, dt, J=11.0 and 6.9, H-10α), 2.59 (2H, m, H-8β+H-10β), 2.38 (1H, dd, J$_{AB}$=14.0, J=6.7, H-11α), 2.28 and 1.90 (2H, 2d, J$_{AB}$=16.5, CH$_2$CO$_2$), 2.05 (1H, m, H-6$_A$), 1.90 (1H, m, H-6$_B$), 1.75 (2H, CH$_2$-7), 1.5-1.1 (6H, m, 3×CH$_2$), 1.29 (1H, s, 4''-OH), 1.19 (6H, 2s, 2×CH$_3$).

EXAMPLE 41

Preparation of (2'R)-4'-(2-methyl-2-propenyl)-4'-demethyl-homoharringtonine

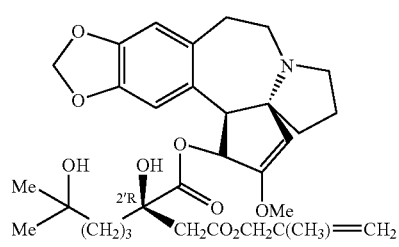

Sodium hydride 60% (23.5 mg, 0.470 mmol) was added to a solution of homoharringtonine (400 mg, 0.734 mmol) in 2-methyl-2-propenol (4 ml) and the resulting mixture was stirred at ambient temperature for 2 hours under argon. After adjusting to pH 2 by addition of hydrochloric acid 0.1N (15 ml) the aqueous layer was washed with ether (3×8 ml). The resulting aqueous layer was alkalinized with ammonia 25% (0.3 ml) and was extracted with dichloromethane (4×8 ml). The combined organic layers were dried over magnesium sulfate and evaporated to dryness (302 mg crude, 70%). The crude product thus obtained was purified by phase-reversed chromatography (octadecylsilane 12 µm (100 g), buffer pH 3/methanol, 55:45). After removal of methanol in vacuo the resulting aqueous layer was alkalinized to pH 9.8 with ammonia 25% (0.9 ml) and extracted with dichloromethane (5×10 ml). The combined organic layers were dried over magnesium sulfate and evaporated to dryness to provide the expected compound (183 mg; 43%). The product thus obtained showed the following characteristics:

$^1$H NMR 400 MHz (CDCl$_3$) (δ ppm, J Hz): 6.62 (1H, s, H-17), 6.54 (1H, s, H-14), 5.98 (1H, d, J$_{3-4}$=9.8, H-3), 5.85 (2H, s, OCH$_2$O), 5.05 (1H, s, H-1), 4.96 and 4.91 (2H, 2s, =CH$_2$), 4.47 and 4.33 (2H, 2d, J$_{AB}$=13.3, OCH$_2$), 3.77 (1H, d, J$_{4-3}$=9.8, H-4), 3.68 (3H, s, OCH$_3$), 3.51 (1H, s, 2'-OH), 3.09 (2H, m, H-11β+H-8α), 2.94 (1H, dt, J=11.0 and 6.8, H-10α), 2.59 (2H, m, H-8β+H-10β), 2.38 (1H, dd, J$_{AB}$=14.0, J=6.7, H-11α), 2.30 and 1.92 (2H, 2d, J$_{AB}$32 16.5, C$\underline{H}_2$CO$_2$), 2.02 (1H, m, H-6$_A$), 1.90 (1H, m, H-6$_B$), 1.75 (2H, m, CH$_2$-7), 1.73 (3H, s, CH$_3$—C≡), 1.5-1.1 (6H, m, 3×CH$_2$), 1.19 (6H, 2s, 2×CH$_3$).

EXAMPLE 42

Preparation of (2'R)-4'-(2-butynyl)-4'-demethyl-homoharringtonine

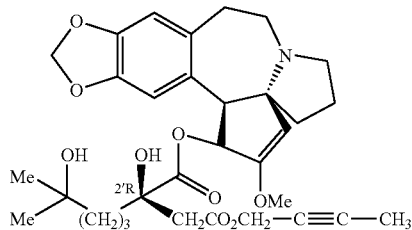

Sodium hydride 60% (30 mg, 0.75 mmol) was added (in 5 parts, at t=0, t=1.5, t=3.5, t=5 and t=24 hours) to a solution of homoharringtonine (510 mg, 0.936 mmol) in 2-butynol (2.9 ml) with stirring at ambient temperature under argon. 2 hours after the last addition the mixture was adjusted to pH 2.1 by addition of hydrochloric acid 0.1N (17 ml) and the aqueous layer was washed with ether (3×10 ml). The resulting aqueous layer was alkalinized with ammonia 25% (0.3 ml) and was extracted with dichloromethane (6×10 ml). The combined organic layers were dried over magnesium sulfate and evaporated to dryness (368 mg crude, 67.5%). The crude product thus obtained was purified by phase-reversed chromatography (octadecylsilane 12 □m (100 g), buffer pH 3/methanol, 65:35). After removal of methanol in vacuo the resulting aqueous layer was alkalinized to pH 10 with ammonia 25% (0.4 ml) and extracted with dichloromethane (6×8 ml). The combined organic layers were dried over magnesium sulfate and evaporated to dryness to provide the expected compound (171 mg; 46.5%). The product thus obtained showed the following characteristics:

$^1$H NMR 400 MHz (CDCl$_3$) (δ ppm, J Hz): 6.62 (1H, s, H-17), 6.54 (1H, s, H-14), 5.99 (1H, d, J$_{3-4}$=9.5, H-3), 5.94 and 5.87 (2H, 2d, J$_{AB}$=1.5, OCH$_2$O), 5.05 (1H, s, H-1), 4.60 and 4.48 (2H, 2dq, J$_{AB}$=15.2, J=2.4, OCH$_2$), 3.77 (1H, d, J$_{4-3}$=9.8, H-4), 3.67 (3H, s, OCH$_3$), 3.51 (1H, s, 2'-OH), 3.09 (2H, m, H-11β+H-8α), 2.94 (1H, m, H-10α), 2.59 (2H, m, H-8β+H-10β), 2.38 (1H, dd, J$_{AB}$=13.9, J=6.7, H-11α), 2.30 and 1.88 (2H, 2d, J$_{AB}$=16.5, C$\underline{H}_2$CO$_2$), 2.02 (1H, m, H-6$_A$), 1.88 (1H, m, H-6$_B$), 1.86 (3H, t, J=2.4, C$\underline{H}_3$—C≡), 1.76 (2H, m, CH$_2$-7), 1.5-1.1 (6H, m, 3×CH$_2$), 1.19 (3H, s, CH$_3$), 1.18 (3H, s, CH$_3$).

EXAMPLE 43

Preparation of (2'R)-4'-(hexa-2,4-dienyl)-4'-demethyl-homoharringtonine

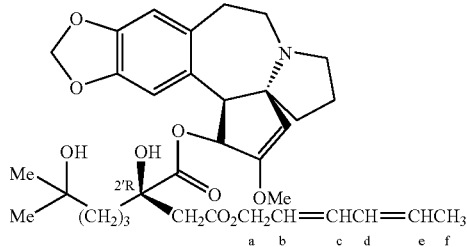

Sodium hydride 60% (8.8 mg, 0.22 mmol) was added to a solution of homoharringtonine (300 mg, 0.55 mmol) in (E,E)-hexa-1,4-dienol (3 ml) and the resulting mixture was stirred at 35° C. for 1 h 45 min under argon. After adjusting to pH 1.9 by addition of hydrochloric acid 0.1N (9 ml) the aqueous layer was washed with ether (3×6 ml). The resulting aqueous layer was alkalinized to pH 10 with ammonia 25% (0.3 ml) and was extracted with dichloromethane (4×6 ml). The combined organic layers were dried over magnesium sulfate and evaporated to dryness (224 mg crude, 67%). The crude product thus obtained was purified by phase-reversed chromatography (octadecylsilane 12 □m (100 g), buffer pH 3/methanol, 40:60). After removal of methanol in vacuo the resulting aqueous layer was washed with ether (10 ml), alkalinized to pH 9.5 with ammonia 25% (0.3 ml) and extracted with dichloromethane (6×8 ml). The combined organic layers were dried over magnesium sulfate and evaporated to dryness to provide the expected compound (175 mg; 43%). The product thus obtained showed the following characteristics:

$^1$H NMR 400 MHz (CDCl3) (δ ppm, J Hz): 6.62 (1H, s, H-17), 6.53 (1H, s, H-14), 6.22 (1H, dd, J$_{c-b}$=15.2, J$_{c-d}$=10.5, H-c), 6.06 (1H, ddd, J$_{d-e}$=15.0, J$_{d-c}$=10.6, J$_{d-f}$=1.4, H-d), 5.98 (1H, d, J$_{3-4}$=9.8, H-3), 5.84 and 5.83 (2H, 2d, J$_{AB}$=1.5, OCH$_2$O), 5.76 (1H, dq, J$_{e-d}$=15.0, J$_{e-f}$=6.8, H-e), 5.56 (1H, dt, J$_{b-c}$=15.3, J$_{b-a}$=6.6, H-b), 5.05 (1H, s, H-1), 4.53 and 4.42 (2H, 2dd, J$_{AB}$=12.8, J$_{a-b}$=6.6, CH$_2$-a), 3.70 (1H, d, J$_{4-3}$=9.8, H-4), 3.67 (3H, s, OCH$_3$), 3.52 (1H, s, 2'-OH), 3.09 (2H, m, H-11β+H-8α), 2.94 (1H, dt, J=11.5 and 6.9, H-10α), 2.58 (2H, m, H-8β+H-10β), 2.38 (1H, dd, J$_{AB}$=14.0, J=6.7, H-11α), 2.26 and 1.88 (2H, 2d, J$_{AB}$=16.4, C$\underline{H}_2$CO$_2$), 2.02 (1H, m, H-6$_A$), 1.90 (1H, m, H-6$_B$), 1.77 (3H, d, J~6, CH$_3$-f) and (2H, m, CH$_2$-7), 1.5-1.1 (6H, m, 3×CH$_2$), 1.28 (1H, s, 4" OH), 1.19 (3H, s, CH$_3$), 1.18 (3H, s, CH$_3$).

EXAMPLE 44

Preparation of (2'R)-4'-(methylcyclopropyl)methyl-4'-demethyl-homoharringtonine

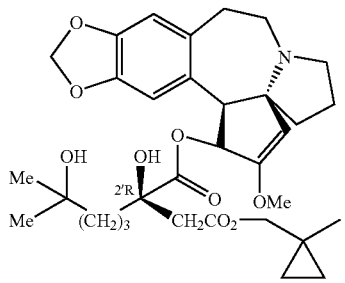

Sodium hydride 60% (3.8 mg, 0.095 mmol) was added to a solution of homoharringtonine (263 mg, 0.482 mmol) in (1-methylcyclopropyl)methanol (2.3 ml) and the resulting mixture was stirred at ambient temperature for 20 h under argon. After adjusting to pH 2 by addition of hydrochloric acid 0.1N (9 ml) the aqueous layer was washed with ether (3×10 ml). The resulting aqueous layer was alkalinized to pH 9.5 with ammonia 25% (0.3 ml) and was extracted with dichloromethane (6×8 ml). The combined organic layers were dried over magnesium sulfate and evaporated to dryness (231 mg crude, 80%). The crude product thus obtained was purified by phase-reversed chromatography (octadecylsilane 12 μm (100 g), buffer pH 3/methanol, 50:50). After removal of methanol in vacuo the resulting aqueous layer was alkalinized to pH 9.5 with ammonia 25% (0.4 ml) and extracted with dichloromethane (6×8 ml). The combined organic layers were dried over magnesium sulfate and evaporated to dryness to provide the expected compound (173 mg; 69%). The product thus obtained showed the following characteristics:

$^1$H NMR 400 MHz (CDCl3) (δ ppm, J Hz): 6.62 (1H, s, H-17), 6.55 (1H, s, H-14), 5.99 (1H, d, $J_{3-4}$=9.6, H-3), 5.86 (2H, s, OCH$_2$O), 5.06 (1H, s, H-1), 3.86 and 3.72 (2H, 2d, $J_{AB}$=11.2, CH$_2$-a), 3.78 (1H, d, $J_{4-3}$=9.6, H-4), 3.68 (3H, s, OCH$_3$), 3.53 (1H, s, 2'-OH), 3.10 (2H, m, H-11β+H-8α), 2.95 (1H, m, H-10α), 2.58 (2H, m, H-8β+H-10β), 2.39 (1H, dd, $J_{AB}$=14.0, J=6.7, H-11α), 2.28 and 1.95 (2H, 2d, $J_{AB}$=16.3, CH$_2$CO$_2$), 2.02 (1H, m, H-6$_A$), 1.90 (1H, m, H-6$_B$), 1.76 (2H, m, CH$_2$-7), 1.5-1.1 (6H, m, 3×CH$_2$), 1.29 (1H, s, 4''-OH), 1.19 (6H, 2s, 2×CH$_3$), 1.09 (3H, s, CH$_3$-c), 0.44 and 0.35 (4H, 2m, CH$_2$-d,e).

EXAMPLE 45

Preparation of (−)-cephalotaxyl (2'S)-2-(2,2,2-trifluoro-ethoxy)carbonylmethyl-6,6-dimethyl-2-tetrahydropyrane carboxylate or 4'-(2,2,2-trifluoroethyl)-4'-demethyl-anhydro-epi-homoharringtonine

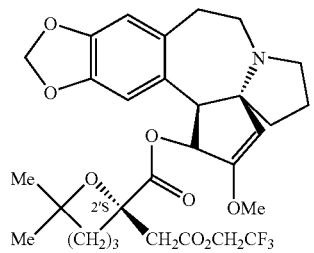

To a stirred mixture of 4'-demethyl-anhydro-epi-homoharringtonine (1 g, 1.947 mmol) in dry dichloromethane (10 ml) under argon was added at 0° C. triethylamine (dried over potassium hydroxide) (270 μl, 1.947 mmol) and 2,4,6-trichlorobenzoyl chloride (305 μl, 1.947 mmol) over a period of 10 minutes. After stirring at ambient temperature for 2.5 hours a solution of 4-dimethylaminopyridine (476 mg, 3.896 mmol) and 2,2,2-trifluoroethanol (280 μl, 3.899 mmol) in dry dichloromethane (3 ml) was added. After stirring at ambient temperature for 20 hours, the reaction mixture was diluted with dichloromethane (19 ml). The resulting organic layer was successively washed with water (27 ml), with saturated sodium hydrogen carbonate solution (27 ml), wit) brine (27 ml). After a last extraction of the combined aqueous layers with dichloromethane (27 ml) the combined organic layers were dried over magnesium sulfate and evaporated to dryness. The resulting crude product was purified by column chromatography (silica 15-40 μm (10 g), dichloromethane then dichloromethane/methanol, 99:1 to 80:20) to provide the expected compound (838 mg, 72%). The product thus obtained showed the following characteristics:

$^1$H NMR 400 MHz (CDCl$_3$) (δ ppm, J Hz): 6.61 (1H, s, H-14*), 6.57 (1H, s, H-17*), 5.83 (3H, m, H-3+OCH$_2$O), 5.02 (1H, s, H-1), 4.43 and 4.33 (2H, 2dq, $J_{AB}$=12.7, JH-F=8.6, OCH$_2$CF$_3$), 3.78 (1H, d, $J_{4-3}$=9.7, H-4), 3.65 (3H, s, OCH$_3$), 3.23 (1H, m, H-11β), 3.09 (1H, m, H-8α), 2.94 (1H, dt, J=11.6 and 7.2, H-10α), 2.60 (2H, m, H-8β+H-10β), 2.39 (1H, m, H-11α), 2.18 and 1.84 (2H, 2d, $J_{AB}$=14.5, CH$_2$CO$_2$), 2.01 (1H, m, H-6$_A$), 1.89 (1H, m, H-6$_B$), 1.74 (2H, m, CH$_2$-7), 1.5-1.2 (6H, m, 3×CH$_2$), 1.10 (3H, s, CH$_3$), 1.03 (3H, s, CH$_3$).

EXAMPLE 46

Preparation of (2'S)-4'-(2,2,2-trifluoroethyl)-4'-demethyl-epi-homoharringtonine

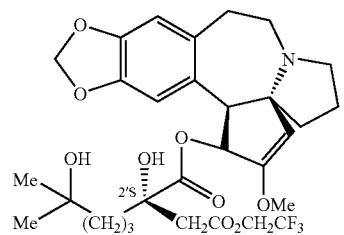

To a stirred solution of 4'-(2,2,2-trifluoroethyl)-4'-demethyl-anhydro-epi-homoharringtonine (300 mg, 0.504 mmol) resulting from Example 45 in dry dichloromethane (1.55 ml) under argon was added at −10° C. a commercial solution of hydrobromic acid in acetic acid (0.903 ml, 4.53 mmol, HBr 30% w/w). After stirring at −10° C. for 3 hours, was added water (14 ml) and the temperature was raised to 20° C. After stirring at 20° C. for 2.75 hours, was added a sodium carbonate solution (0.76 M, 25 ml) up to pH 8.7. The resulting aqueous layer, after saturation with sodium chloride, was extracted with dichloromethane (3×11.4 ml) and the combined organic layers were dried over magnesium sulfate and evaporated to dryness. The resulting crude product was purified by column chromatography (silica 15-40 μm (15 g), dichloromethane/methanol, 99:1 to 90:10) to provide the expected compound (211 mg, 68%). The product thus obtained showed the following characteristics:

¹H NMR 400 MHz (CDCl₃) (δ ppm, J Hz): 6.65 (1H, s, H-17*), 6.60 (1H, s, H-14*), 5.94 and 5.85 (2H, 2d, J$_{AB}$=1.3, OCH₂O), 5.93 (1H, d, H-3), 5.05 (1H, s, H-1), 4.53 and 4.32 (2H, 2dq, J$_{AB}$=12.6, JH-F=8.4, OCH₂CF₃), 3.79 (1H, d, J$_{4-3}$=9.6, H-4), 3.65 (3H, s, OCH₃), 3.36 (1H, s, 2'-OH), 3.08 (2H, m, H-11β+H-8α), 2.93 (1H, m, H-10α), 2.70 and 2.64 (2H, 2d, J$_{AB}$=16.8, CH₂CO₂), 2.57 (2H, m, H-8β+H-10β), 2.38 (1H, dd, J$_{AB}$=14.0, J=6.8, H-11α), 2.01 (1H, m, H-6$_A$), 1.89 (1H, m, H-6$_B$), 1.76 (2H, m, CH₂-7), 1.34 (1H, s, 4"-OH), 1.3-1.15 (3H, m, CH₂), 1.17 (3H, s, CH₃), 1.16 (3H, s, CH₃), 1.03 (1H, m, CH₂), 0.97 (1H, m, CH₂), 0.70 (1H, m, CH₂).

EXAMPLE 47

Preparation of (−)-cephalotaxyl (2'R)-2-(2,2,2-trifluoro-ethoxy)carbonylmethyl-6,6-dimethyl-2-tetrahydropyrane carboxylate or 4'-(2,2,2-trifluoroethyl)-4'-demethyl-anhydro-homoharringtonine

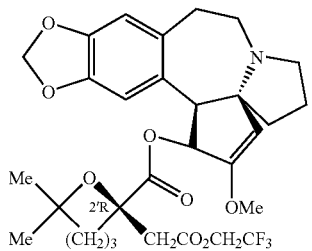

To a stirred mixture of 4'-demethyl-anhydro-homoharringtonine (723 mg, 1.407 mmol) in dry dichloromethane (5.1 ml) under argon was added at 0° C. triethylamine (dried over potassium hydroxide) (196 μl, 1.408 mmol) and 2,4,6-trichlorobenzoyl chloride (220 □l, 1.407 mmol) over a period of 10 minutes. After stirring at ambient temperature for 2.5 hours a solution of 4-dimethylaminopyridine (344 mg, 2.816 mmol) and 2,2,2-trifluoroethanol (202 μl, 2.813 mmol) in dry dichloromethane (2.2 ml) was added. After stirring at ambient temperature for 17 hours, the reaction mixture was diluted with dichloromethane (14 ml). The resulting organic layer was successively washed with water (19 ml), with saturated sodium hydrogen carbonate solution (19 ml), with brine (19 ml). After a last extraction of the combined aqueous layers with dichloromethane (19 ml) the combined organic layers were dried over magnesium sulfate and evaporated to dryness. The resulting crude product was purified by column chromatography (silica 15-40 □m (10 g), dichloromethane/methanol, 99:1 to 90:10) to provide the expected compound (523 mg, 77%). The product thus obtained showed the following characteristics:

¹H NMR 400 MHz (CDCl₃) (δ ppm, J Hz): 6.62 (1H, s, H-17), 6.58 (1H, s, H-14), 5.88 (1H, d, H-3), 5.86 and 5.79 (2H, 2d, J$_{AB}$=1.4, OCH₂O), 5.05 (1H, s, H-1), 4.41 and 4.35 (2H, 2m, OCH₂CF₃), 3.80 (1H, d, J$_{4-3}$=9.7, H-4), 3.70 (3H, s, OCH₃), 3.12 (2H, m, H-11β)+H-8α), 2.96 (1H, m, H-10α), 2.60 (2H, m, H-8β+H-10β), 2.37 (1H, dd, J=14.1 and 6.7, H-11α), 2.20 and 1.68 (2H, 2d, J$_{AB}$=14.7, CH₂CO₂), 2.01 (1H, m, H-6$_A$), 1.93 (1H, m, H-6$_B$), 1.76 (2H, m, CH₂-7), 1.7-1.2 (6H, m, 3×CH₂), 1.10 (3H, s, CH₃), 1.04 (3H, s, CH₃).

EXAMPLE 48

Preparation of (2'R)-4'-(2,2,2-trifluoroethyl)-4'-demethyl-homoharringtonine

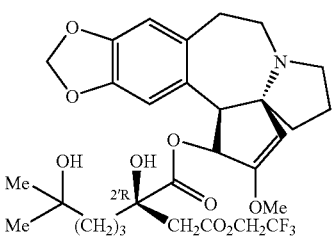

To a stirred solution of 4'-(2,2,2-trifluoroethyl)-4'-demethyl-anhydro-homoharringtonine (507 mg, 0.851 mmol) resulting from Example 47 in dry dichloromethane (2.6 ml) under argon was added at −10° C. a commercial solution of hydrobromic acid in acetic acid (1.525 ml, 7.659 mmol HBr 30% w/w). After stirring at −10° C. for 3 hours, was added water (24 ml) and the temperature was raised to 20° C. After stirring, at 20° C. for 2.75 hours, was added a sodium carbonate solution (0.76 M, 44 ml) up to pH 8.5. The resulting aqueous layer, after saturation with sodium chloride, was extracted with dichloromethane (3×19 ml) and the combined organic layers were dried over magnesium sulfate and evaporated to dryness (508 mg crude, 97%). The crude product thus obtained was purified by phase-reversed chromatography (octadecylsilane 12 μm (100 g), buffer pH 3/methanol, 60:40 to 20:80). After removal of methanol in vacuo the resulting aqueous layer was alkalinized to pH 9.6 with ammonia 25% (0.4 ml) and extracted with dichloromethane (12×10 ml). The combined organic layers were dried over magnesium sulfate and evaporated to dryness to provide the expected compound (122 mg; 23%). The product thus obtained showed the following characteristics:

¹H NMR 400 MHz (CDCl₃) (δ ppm, J Hz): 6.62 (1H, s, H-17), 6.55 (1H, s, H-14), 5.99 (1H, d, J$_{3-4}$=9.7, H-3), 5.86 and 5.84 (2H, 2d, J$_{AB}$=1.2, OCH₂O), 4.42 and 4.26 (2H, 2dd, J$_{AB}$=12.7, J$_{H-F}$=8.4, OCH₂CF₃), 5.05 (1H, s, H-1), 3.78 (1H, d, J$_{4-3}$=9.8, H-4), 3.68 (3H, s, OCH₃), 3.45 (1H, s, 2'-OH), 3.10 (2H, m, H-11β+H-8α), 2.96 (1H, m, H-10α), 2.60 (2H, m, H-8β+H-10β), 2.39 (1H, m, H-11α), 2.37 and 1.93 (2H, 2d, J$_{AB}$=16.5, CH₂CO₂), 2.03 (1H, m, H-6$_A$), 1.92 (1H, m, H-6$_B$), 1.76 (2H, m, CH₂-7), 1.55-1.15 (6H, m, 3×CH₂), 1.25 (1H, s, 4"-OH), 1.19 (6H, 2s, 2×CH₃).

EXAMPLE 49

Preparation of (2'R)-4'-cyclopropylmethyl-4'-demethyl-homoharringtonine

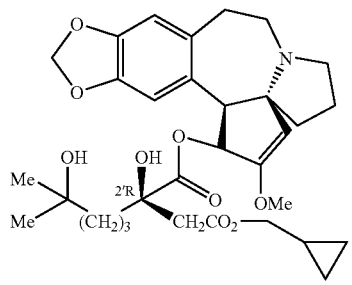

Sodium hydride 60% (3.2 mg, 0.08 mmol) was added to a solution of homoharringtonine (210 mg, 0.385 mmol) in cyclopropylmethanol (1.53 ml) and the resulting mixture was stirred at ambient temperature for 2.5 h under argon. After adjusting to pH 1.8 by addition of hydrochloric acid 0.1N (6 ml) the aqueous layer was washed with ether (3×5 ml). The resulting aqueous layer was alkalinized to pH 9.5 with ammonia 25% (0.3 ml) and was extracted with dichloromethane (6×5 ml). The combined organic layers were dried over magnesium sulfate and evaporated to dryness (175 mg crude, 78%). The crude product thus obtained was purified by phase-reversed chromatography (octadecylsilane 12 μm (100 g), buffer pH 3/methanol, 57:43). After removal of methanol in vacuo the resulting aqueous layer was alkalinized to pH 9.5 with ammonia 25% (0.4 ml) and extracted with dichloromethane (6×6 ml). The combined organic layers were dried over magnesium sulfate and evaporated to dryness to provide the expected compound (170 mg; 51%). The product thus obtained showed the following characteristics:

$^1$H NMR 400 MHz (CDCl3) (δ ppm, J Hz): 6.62 (1H, s, H-17), 6.55 (1H, s, H-14), 5.98 (1H, d, $J_{3-4}$=9.8, H-3), 5.87 and 5.86 (2H, 2d, $J_{AB}$=1.3, OCH$_2$O), 5.06 (1H, s, H-1), 3.83 and 3.77 (2H, 2dd, $J_{AB}$=11.4, $J_{a-b}$=1.3, CH$_2$-a), 3.78 (1H, d, $J_{4-3}$~10, H-4), 3.68 (3H, s, OCH$_3$), 3.55 (1H, s, 2'-OH), 3.10 (2H, m, H-11β+H-8α), 2.95 (1H, m, H-10α), 2.61 (2H, m, H-8β+H-10β), 2.39 (1H, dd, $J_{AB}$=14.1, J=6.8, H-11α), 2.27 and 1.93 (2H, 2d, $J_{AB}$=16.3, C$\underline{H}_2$CO$_2$), 2.03 (1H, m, H-6$_A$), 1.93 (1H, m, H-6$_B$), 1.76 (2H, m, CH$_2$-7), 1.5-1.1 (6H, m, 3×CH$_2$), 1.19 (3H, s, CH$_3$), 1.18 (3H, s, CH$_3$), 1.06 (1H, m, H-b), 0.55 and 0.24 (4H, 2m, CH$_2$-c, d).

EXAMPLE 50

Preparation of (2'R)-4'-butyl-4'-demethyl-homoharringtonine

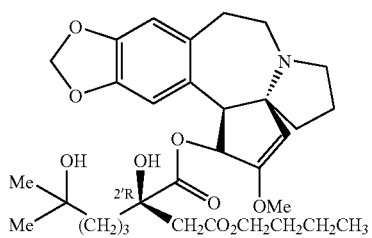

Sodium hydride 60% (4.95 mg, 0.124 mmol) was added to a solution of homoharringtonine (225 mg, 0.4125 mmol) in n-butanol (2.25 ml) and the resulting mixture was stirred at ambient temperature for 20 hours under argon. After adjusting to pH 1.9 by addition of hydrochloric acid 0.1N (6 ml) the aqueous layer was washed with ether (3×6 ml). The resulting aqueous layer was alkalinized to pH 10 with ammonia 25% (0.43 ml) and was extracted with dichloromethane (10×8 ml). The combined organic layers were dried over magnesium sulfate and evaporated to dryness (178 mg crude, 74%). The crude product thus obtained was purified by phase-reversed chromatography (octadecylsilane 12 μm (100 g), buffer pH 3/methanol, 50:50). After removal of methanol in vacuo the resulting aqueous layer was alkalinized to pH 9.5 with ammonia 25% (0.4 ml) and extracted with dichloromethane (8×10 ml). The combined organic layers were dried over magnesium sulfate and evaporated to dryness to provide the expected compound (107 mg; 44%). The product thus obtained showed the following characteristics:

$^1$H NMR 400 MHz (CDCl3) (δ ppm, J Hz): 6.62 (1H, s, H-17), 6.55 (1H, s, H-14), 5.98 (1H, d, $J_{3-4}$=9.7, H-3), 5.86 (2H, s, OCH$_2$O), 5.05 (1H, s, H-1), 4.02 and 3.92 (2H, 2dt, $J_{AB}$=10.8, $J_{a-b}$=6.8, C$\underline{H}_2$-a), 3.78 (1H, d, $J_{4-3}$=9.8, H-4), 3.68 (3H, s, OCH$_3$), 3.52 (1H, s, 2'-OH), 3.11 (2H, m, H-11β+H-8α), 2.95 (1H, m, H-10α), 2.60 (2H, m, H-8β+H-10β), 2.39 (1H, dd, J=14.1 and 6.8, H-11α), 2.25 and 1.92 (2H, 2d, $J_{AB}$=16.3, C$\underline{H}_2$CO$_2$), 2.03 (1H, m, H-6$_A$), 1.92 (1H, m, H-6$_B$), 1.76 (2H, m, CH$_2$-7), 1.55 (2H, m, CH$_2$-b), 1.45-1.15 (8H, m, CH$_2$-c and 3×CH$_2$), 1.19 (3H, s, CH$_3$), 1.18 (3H, s, CH$_3$), 0.92 (3H, t, J=7.3, CH$_3$-d)

EXAMPLE 51

Preparation of (2'R)-4'-propyl-4'-demethyl-homoharringtonine

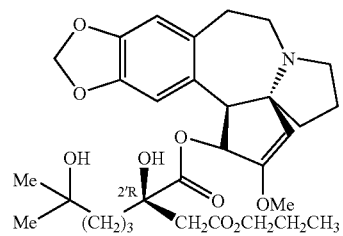

Sodium hydride 60% (8.9 mg, 0.223 mmol) was added to a solution of homoharringtonine (405 mg, 0.742 mmol) in n-propanol (4 ml) and the resulting mixture was stirred at ambient temperature for 1.5 h under argon. After adjusting to pH 1.9 by addition of hydrochloric acid 0.1N (12 ml) the aqueous layer was washed with ether (3×8 ml). The resulting aqueous layer was alkalinized to pH 9.6 with ammonia 25% (0.8 ml) and was extracted with dichloromethane (6×10 ml). The combined organic layers were dried over magnesium sulfate and evaporated to dryness (374 mg crude, 88%). The crude product thus obtained was purified by phase-reversed chromatography (octadecylsilane 12 μm (100 g), buffer pH 3/methanol, 62:38 to 50:50). After removal of methanol in vacuo the resulting aqueous layer was alkalinized to pH 9.5 with ammonia 25% (0.8 ml) and extracted with dichloromethane (6×10 ml). The combined organic layers were dried over magnesium sulfate and evaporated to dryness to provide the expected compound (244 mg; 57%). The product thus obtained showed the following characteristics:

$^1$H NMR 400 MHz (CDCl$_3$) (δ ppm, J Hz): 6.62 (1H, s, H-17), 6.54 (1H, s, H-14), 5.98 (1H, d, $J_{3-4}$=9.7, H-3), 5.86 (2H, s, OCH$_2$O), 5.05 (1H, s, H-1), 3.97 and 3.89 (2H, 2dt, $J_{AB}$=10.6, $J_{a-b}$=6.8, C$\underline{H}_2$-a), 3.78 (1H, d, $J_{4-3}$=9.8, H-4), 3.68 (3H, s, OCH$_3$), 3.52 (1H, s, 2'-OH), 3.10 (2H, m, H-11β+H-8α), 2.94 (1H, m, H-10α), 2.60 (2H, m, H-8β+H-10β), 2.38 (1H, dd, J=14.0 and 6.7, H-11α), 2.25 and 1.92 (2H, 2d, $J_{AB}$=16.3, C$\underline{H}_2$CO$_2$), 2.02 (1H, m, H-6$_A$), 1.90 (1H, m, H-6$_B$), 1.76 (2H, m, CH$_2$-7), 1.60 (2H, m, CH$_2$-b), 1.5-1.1 (6H, m, 3×CH$_2$), 1.19 (3H, s, CH$_3$), 1.18 (3H, s, CH$_3$), 0.91 (3H, t, J=7.4, CH$_3$-c)

EXAMPLE 52

Preparation of (2'R)-4'-isobutyl-4'-demethyl-homo-harringtonine

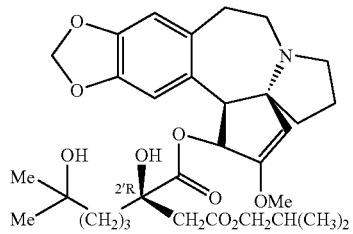

Sodium hydride 60% (8.8 mg, 0.220 mmol) was added to a solution of homoharringtonine (3975 mg, 0.7282 mmol) in iso-butanol (4 ml) and the resulting mixture was stirred at ambient temperature for 1.5 h under argon. After adjusting to pH 1.8 by addition of hydrochloric acid 0.1N (11 ml) the aqueous layer was washed with ether (3×8 ml). The resulting aqueous layer was alkalinized to pH 9.7 with ammonia 25% and was extracted with dichloromethane (6×10 ml). The combined organic layers were dried over magnesium sulfate and evaporated to dryness (316 mg crude, 768%). The crude product thus obtained was purified by phase-reversed chromatography (octadecylsilane 12 μm (135 g), buffer pH 3/methanol, 50:50). After removal of methanol in vacuo the resulting aqueous layer was alkalinized to pH 9.5 with ammonia 25% and extracted with dichloromethane (6×10 ml). The combined organic layers were dried over magnesium sulfate and evaporated to dryness to provide the expected compound (254 mg; 61%). The product thus obtained showed the following characteristics:

$^1$H NMR 400 MHz (CDCl$_3$) (δ ppm, J Hz): 6.62 (1H, s, H-17), 6.55 (1H, s, H-14), 5.98 (1H, d, J$_{3-4}$=9.5, H-3), 5.86 (2H, s, OCH$_2$O), 5.06 (1H, s, H-1), 3.81 and 3.71 (2H, 2dt, J$_{AB}$=10.7, J$_{a-b}$=6.7, CH$_2$-a), 3.78 (1H, d, J$_{4-3}$=9.5, H-4), 3.68 (3H, s, OCH$_3$), 3.52 (1H, s, 2'-OH), 3.11 (2H, m, H-11β+H-8α), 2.94 (1H, m, H-10α), 2.60 (2H, m, H-8β+H-10β), 2.38 (1H, dd, J=14.1 and 6.8, H-11α), 2.26 and 1.94 (2H, 2d, J$_{AB}$=16.3, CH$_2$CO$_2$), 2.04 (1H, m, H-6$_A$), 1.90 (1H, m, H-6$_B$), 1.85 (1H, m, H-b), 1.76 (2H, m, CH$_2$-7), 1.5-1.15 (6H, m, 3×CH$_2$), 1.19 (6H, 2s, 2×CH$_3$), 0.91 (3H, d, J$_{c-b}$=6.8, CH$_3$-c), 0.90 (3H, d, J$_{d-b}$=6.8, CH$_3$-d).

EXAMPLE 53

Preparation of (2'R)-4'-(hex-4-enyl)-4'-demethyl-homoharringtonine

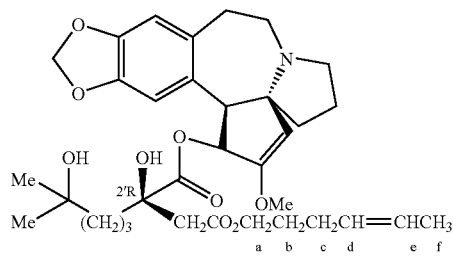

Sodium hydride 60% (10.96 mg, 0.274 mmol) was added to a solution of homoharringtonine (374 mg, 0.685 mmol) in 4-hexenol (4 ml) and the resulting mixture was stirred at ambient temperature for 45 min under argon. After adjusting to pH 1.9 by addition of hydrochloric acid 0.1N (12 ml) the aqueous layer was washed with ether (3×8 ml). The resulting aqueous layer was alkalinized to pH 10 with ammonia 25% and was extracted with dichloromethane (6×10 ml). The combined organic layers were dried over magnesium sulfate and evaporated to dryness (358 mg crude, 85%). The crude product thus obtained was purified by phase-reversed chromatography (octadecylsilane 12 μm (135 g), buffer pH 3/methanol, 30:70). After removal of methanol in vacuo the resulting aqueous layer was washed with ether (5 ml), dichloromethane (5 ml), alkalinized to pH 9.5 with ammonia 25% (0.8 ml) and extracted with dichloromethane (6×10 ml). The combined organic layers were dried over magnesium sulfate and evaporated to dryness to provide the expected compound (226 mg; 54%). The product thus obtained showed the following characteristics:

$^1$H NMR 400 MHz (CDCl$_3$) (δ ppm, J Hz): 6.62 (1H, s, H-17), 6.54 (1H, s, H-14), 5.98 (1H, d, J$_{3-4}$=9.7, H-3), 5.85 (2H, s, OCH$_2$O), 5.42 (2H, m, H-e,d), 5.05 (1H, s, H-1), 3.99 and 3.92 (2H, 2m, CH$_2$-a), 3.78 (1H, d, J$_{4-3}$=9.7, H-4), 3.68 (3H, s, OCH$_3$), 3.52 (1H, s, 2'-OH), 3.10 (2H, m, H-11β+H-8α), 2.94 (1H, m, H-10α), 2.59 (2H, m, H-8β+H-10β), 2.38 (1H, dd, J=14.0 and 6.7, H-11α), 2.24 and 1.92 (2H, 2d, J$_{AB}$=16.2, CH$_2$CO$_2$), 2.0 (3H, m, H-6$_A$ and CH$_2$-c), 1.92 (1H, m, H-6$_B$), 1.76 (2H, m, CH$_2$-7), 1.63 (5H, m, CH$_2$-b and CH$_3$-f), 1.5-1.1 (6H, m, 3×CH$_2$), 1.18 (6H, 2s, 2×CH$_3$).

EXAMPLE 54

Preparation of (2'R)-4'-hexyl-4'-demethyl-homoharringtonine

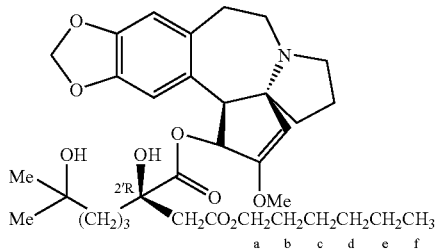

Sodium hydride 60% (6.6 mg, 0.16 mmol) was added to a solution of homoharringtonine (300 mg, 0.55 mmol) in n-hexanol (3 ml) and the resulting mixture was stirred at ambient temperature for 1.5 hours under argon. After adjusting to pH 1.9 by addition of hydrochloric acid 0.1N (5 ml) the aqueous layer was washed with ether (3×10 ml). The resulting aqueous layer was alkalinized to pH 9.5 with ammonia 25% and was extracted with dichloromethane (6×10 ml). The combined organic layers were dried over magnesium sulfate and evaporated to dryness. The crude product thus obtained was purified by phase-reversed chromatography (octadecylsilane 12 μm (135 g), buffer pH 3/methanol, 30:70). After removal of methanol in vacuo and ajusting to pH 1.9 by addition of hydrochloric acid 0.1N (5 ml), the resulting aqueous layer was washed with ether (3×5 ml), alkalinized to pH 9.5 with ammonia 25% and extracted with dichloromethane (6×10 ml). The combined organic layers were dried over magnesium sulfate and evaporated to dryness to provide the expected compound (158 mg; 47%).

The product thus obtained showed the following characteristics:

$^1$H NMR 400 MHz (CDCl$_3$) (δ ppm, J Hz): 6.62 (1H, s, H-17), 6.55 (1H, s, H-14), 5.98 (1H, d, J$_{3-4}$=9.8, H-3), 5.86 (2H, s, OCH$_2$O), 5.05 (1H, s, H-1), 4.0 and 3.91 (2H, 2m, CH$_2$-a), 3.78 (1H, d, J$_{4-3}$=9.9, H-4), 3.68 (3H, s, OCH$_3$), 3.52 (1H, s, 2'-OH), 3.10 (2H, m, H-11β+H-8α), 2.94 (1H, m, H-10α), 2.60 (2H, m, H-8β+H-10β), 2.39 (1H, dd, J=13.8 and 6.7, H-11α), 2.25 and 1.92 (2H, 2d, J$_{AB}$=16.2, CH$_2$CO$_2$), 2.17 (1H, m, H-6$_A$), 1.92 (1H, m, H-6$_B$), 1.76 (2H, m, CH$_2$-7), 1.56 (2H, m, CH$_2$-b), 1.5-1.1 (12H, m, CH$_2$c,d,e and 3×CH$_2$), 1.19 (3H, s, CH$_3$), 1.18 (3H, s, CH$_3$), 0.89 (3H, t, J=6.83, CH$_3$f)

EXAMPLE 55

Preparation of (2'R)-4'-(but-2-enyl)-4'-demethylharringtonine

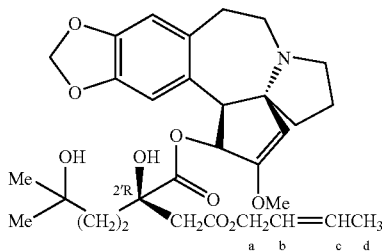

Sodium hydride 60% (7.4 mg, 0.188 mmol) was added to a solution of harringtonine (250 mg, 0.471 mmol) in crotyl alcohol (2.5 ml) and the resulting mixture was stirred at ambient temperature for 2.5 hours. After adjusting to pH 4 by addition of hydrochloric acid 1N the aqueous layer was washed with ether (3×10 ml). The resulting aqueous layer was-alkalinized with ammonia 25% and was extracted with dichloromethane (3×10 ml). The combined organic layers were dried over magnesium sulfate and evaporated to dryness (268 mg crude, 99.50%). The crude product thus obtained was purified by phase-reversed chromatography (octadecylsilane 12 μm (100 g), buffer pH 3/methanol, 65:35 to 60:40). After removal of methanol in vacuo the resulting aqueous layer was alkalinized to pH 9.2 with ammonia 25% and extracted with dichloromethane (6×15 ml). The combined organic layers were dried over magnesium sulfate and evaporated to dryness to provide the expected compound (157 mg; 58.5%). The product thus obtained showed the following characteristics:

$^1$H NMR 400 MHz (CDCl$_3$) (δ ppm, J Hz): 6.62 (1H, s, H-17), 6.55 (1H, s, H-14), 5.98 (1H, d, J$_{3-4}$=9.7, H-3), 5.85 (2H, s, OCH$_2$O), 5.75 (1H, dq, J$_{c-b}$=15.3, J$_{c-d}$=6.4, H-c), 5.55 (1H, dtq, J$_{b-c}$=15.3, J$_{b-a}$=6.4, J$_{b-d}$=1.7, H-b), 5.07 (1H, s, H-1), 4.47 and 4.35 (2H, 2dd, J$_{AB}$=12.3, J$_{a-b}$=6.5, CH$_2$-a), 3.78 (1H, d, J$_{4-3}$=9.6, H-4), 3.70 (3H, s, OCH$_3$), 3.63 (1H, s, 2'-OH), 3.10 (2H, m, H-11β+H-8α), 2.95 (1H, m, H-10α), 2.58 (2H, m, H-8β+H-10β), 2.398 (1H, m, H-11α), 2.28 and 1.89 (2H, 2d, J$_{AB}$=16.4, CH$_2$CO$_2$), 2.01 (1H, m, H-6$_A$), 1.89 (1H, m, H-6$_B$), 1.76 (2H, m, CH$_2$-7), 1.72 (3H, dd, J$_{d-c}$=6.6, J$_{d-b}$=1.2, CH$_3$-d), 1.60 (3H, m, CH$_2$), 1.25 (1H, m, CH$_2$), 1.17 (3H, s, CH$_3$), 1.14 (3H, s, CH$_3$).

EXAMPLE 56

Preparation of 4-(2-butenyl) (2R)-2-hydroxy-2-(4-hydroxy-4-methylpentyl)succinate of (−)-drupacine

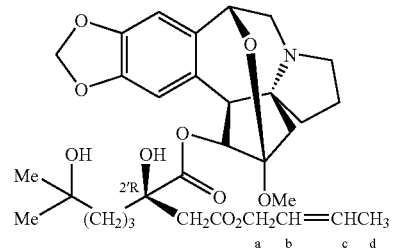

Sodium hydride 60% (14 mg, 0.358 mmol) was added to a solution of 4-methyl (2R)-2-hydroxy-2-(4-hydroxy-4-methylpentyl)succinate of (−)-drupacine (500 mg, 0.8 mmol) in crotyl alcohol (4.5 ml) and the resulting mixture was stirred at ambient temperature for 2.5 hours. After adjusting to pH 4' by addition of hydrochloric acid 1N the aqueous layer was washed with ether (3×10 ml). The resulting aqueous layer was alkalinized with ammonia 25% and was extracted with dichloromethane (3×10 ml). The combined organic layers were dried over magnesium sulfate and evaporated to dryness (366 mg crude, 74%). The crude product thus obtained was purified by phase-reversed chromatography (octadecylsilane 12 μm (100 g), buffer pH 3/methanol, 57:43). After removal of methanol in vacuo the resulting aqueous layer was alkalinized to pH 10.6 with ammonia 25% and extracted with dichloromethane (6×10 ml). The combined organic layers were dried over magnesium sulfate and evaporated to dryness to provide the expected compound (132 mg; 27%). The product thus obtained showed the following characteristics:

$^1$H NMR 400 MHz (CDCl$_3$) (δ ppm, J Hz): 6.65 (1H, s, H-17*), 6.46 (1H, s, H-14*), 5.90 and 5.87 (2H, 2d, J$_{AB}$=1.5, OCH$_2$O), 5.79 (1H, m, H-c), 5.57 (1H, m, H-b), 5.23 (1H, d, J$_{3-4}$=9.6, H-3), 4.86 (1H, d, J$_{11-10A}$=4.3, H-11), 4.56 and 4.45 (2H, 2dd, J$_{AB}$=12.3, J$_{a-b}$=6.6, CH$_2$-a), 3.56 (1H, d, J$_{4-3}$=9.6, H-4), 3.51 (1H, s, 2'-OH), 3.41 (3H, s, OCH$_3$), 3.12 (1H, dd, J$_{AB}$=13.2, J$_{10A-11}$=4.9, H-10$_A$), 3.08 (1H, m, H-8α), 2.97 (1H, d, J$_{AB}$=13.1, H-10$_B$), 2.67 (1H, d, J$_{AB}$=14.0, H-1A), 2.40 (1H, ~q, J=8.7, H-8β), 2.29 and 1.96 (2H, 2d, J$_{AB}$=16.4, CH$_2$CO$_2$), 2.19 (1H, m, H-6$_A$), 2.04 (1H, m, H-6$_B$), 1.9-1.1 (8H, m, CH$_2$-7 and 3×CH$_2$), 1.73 (3H, dd, J$_{d-c}$=6.5, J$_{d-b}$=1.1, CH$_3$-d), 1.55 (1H, d, J$_{AB}$=14.0, H-1$_B$), 1.18 (3H, s, CH$_3$), 1.16 (3H, s, CH$_3$).

EXAMPLE 57

Preparation of 4-(hexa-2,4-dienyl) (2R)-2-hydroxy-2-(4-hydroxy-4-methylpentyl)succinate of (−)-drupacine

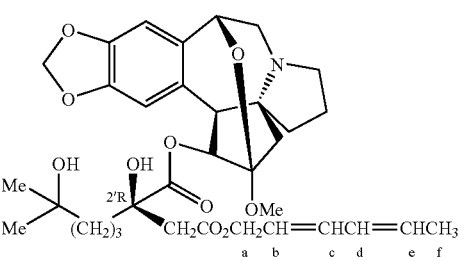

Sodium hydride 60% (6.8 mg, 0.272 mmol) was added to a solution of 4-methyl (2R)-2-hydroxy-2-(4-hydroxy-4-methylpentyl)succinate of (−)-drupacine (200 mg, 0.34 mmol) in hexa-2,4-dienol (2 ml) and the resulting mixture was stirred at ambient temperature for 2 hours. After adjusting to pH 1.5 by addition of hydrochloric acid 1N (7 ml) the aqueous layer was washed with ether (3×10 ml). The resulting aqueous layer was alkalinized to pH 9.5 with ammonia 25% and was extracted with dichloromethane (5×10 ml). The combined organic layers were dried over magnesium sulfate and evaporated to dryness (182 mg crude, 86%). The crude product thus obtained was purified by phase-reversed chromatography (octadecylsilane 12 μm (100 g), buffer pH 3/methanol, 40:60). After removal of methanol in vacuo the resulting aqueous layer was adjusted to pH 1.5 with hydrochloric acid 1N, washed with ether (3×10 ml), alkalinized to pH 10.6 with ammonia 25% and extracted with dichloromethane (5×10 ml). The combined organic layers were dried over magnesium sulfate and evaporated to dryness to provide the expected compound (50 mg; 23.5%). The product thus obtained showed the following characteristics:

$^1$H NMR 400 MHz (CDCl$_3$) (δ ppm, J Hz): 6.65 (1H, s, H-17*), 6.46 (1H, s, H-14*), 6.26 (1H, dd, J$_{c-b}$=15.2, J$_{c-d}$=10.5, H-c), 6.05 (1H, m, H-d), 5.88 and 5.85 (2H, 2d, J$_{AB}$=1.3, OCH$_2$O), 5.76 (1H, m, H-e), 5.60 (1H, m, H-b), 5.23 (1H, d, J$_{3-4}$=9.6, H-3), 4.86 (1H, d, J$_{11-10A}$=4.3, H-11), 4.63 and 4.52 (2H, 2dd, J$_{AB}$=12.9, J$_{a-b}$=6.6, CH$_2$-a), 3.55 (1H, d, J$_{4-3}$=9.6, H-4), 3.51 (1H, s, 2'-OH), 3.41 (3H, s, OCH$_3$), 3.11 (1H, dd, J$_{AB}$=13.3, J$_{10A-11}$=4.9, H-10$_A$), 3.06 (1H, m, H-8α), 2.96 (1H, d, J$_{AB}$32 13.1, H-10$_B$), 2.66 (1H, d, J$_{AB}$=14.0, H-1A), 2.42 (1H, m, H-8β), 2.30 and 1.96 (2H, 2d, J$_{AB}$=16.5, CH$_2$CO$_2$), 2.19 (1H, m, H-6$_A$), 2.05 (1H, m, H-6$_B$), 1.77 (2H, m, CH$_2$-7) and (3H, d, J$_{f-e}$=6.2, CH$_3$-f), 1.6-1.1 (6H, m, 3×CH$_2$), 1.55 (1H, d, J$_{AB}$=14.0, H-1$_B$), 1.17 (3H, s, CH$_3$), 1.16 (3H, s, CH$_3$).

EXAMPLE 58

Preparation of (2'R)-4''-Fluoro-4''-deoxy-homoharringtonine

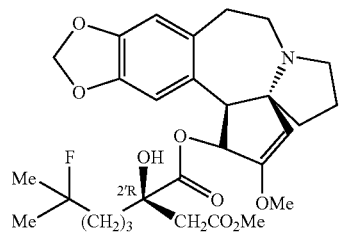

To a stirred solution of homoharringtonine (20 mg, 0.037 mmol) in dry dichloromethane (1.5 ml) under nitrogen was slowly added DAST (25 μl, 0.185 mmol) at −40° C. After stirring at −20° C. for 3 hours, was added a saturated sodium hydrogen carbonate solution (2 ml), the resulting aqueous layer was extracted with dichloromethane (3×5 ml) and the combined organic layers were washed with water (5 ml), with brine (5 ml), were dried over magnesium sulfate and evaporated to dryness. The resulting crude product (13 mg) was purified by column chromatography (silica 15-40 μm (0.2 g), dichloromethane then dichloromethane/methanol, 98:2) to provide the expected compound (4 mg, 20%). The product thus obtained showed the following characteristics:

$^1$H NMR 400 MHz (CDCl$_3$) (δ ppm, J Hz): 6.63 (1H, s, H-17), 6.54 (1H, s, H-14), 6.08 (1H, d, J$_{3-4}$=9.3, H-3), 5.87 and 5.86 (2H, 2d J$_{AB}$=1.4, OCH$_2$O), 5.04 (1H, s, H-1), 3.77 (1H, d, J$_{4-3}$=9.8, H-4), 3.67 (3H, s, OCH$_3$), 3.57 (3H, s, OCH$_3$), 3.39 (1H, s, 2'-OH), 3.10 (2H, m, H-11β+H-8α), 2.94 (1H, m, H-10α), 2.60 (2H, m, H-8β+H-10β), 2.38 (1H, m, J=14 and 6.8, H-11α), 2.26 and 1.89 (2H, 2d, J$_{AB}$=16.4, CH$_2$CO$_2$), 2.02 (1H, m, H-6$_A$), 1.91 (1H, m, H-6$_B$), 1.75 (2H, m, CH$_2$-7), 1.6-1.2 (6H, m, 3×CH$_2$), 1.34 (3H, d, J$_{H-F}$=21.4, CH$_3$), 1.28 (3H, d, J$_{H-F}$=21.4, CH$_3$).

EXAMPLE 59

Preparation of (2'R)-3''-Fluoro-3''-deoxy-harringtonine

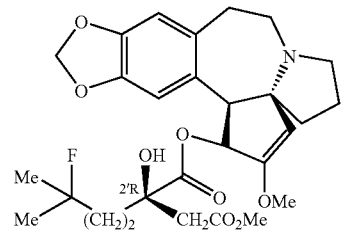

To a stirred solution of harringtonine (50 mg, 0.094 mmol) in dry dichloromethane (3.5 ml) under nitrogen was slowly added DAST (62 μl, 0.47 mmol) at −40° C. After stirring at −20° C. for 3 hours, was added a saturated sodium hydrogen carbonate solution (5 ml), the resulting aqueous layer was extracted with dichloromethane (3×5 ml). The combined organic layers were washed with water (5 ml), with brine (5 ml), dried over magnesium sulfate and evaporated to dryness. The crude product thus obtained was purified by phase-reversed chromatography (octadecylsilane 12 μm (135 g), buffer pH 3/methanol, 45:65). After removal of methanol in vacuo the resulting aqueous layer was adjusted to pH 8.6 with ammonia 25% and extracted with dichloromethane (5×10 ml). The combined organic layers were dried over magnesium sulfate and evaporated to dryness to provide the expected compound (11 mg; 22%). The product thus obtained showed the following characteristics:

$^1$H NMR 400 MHz (CDCl$_3$) (δ ppm, J Hz): 6.63 (1H, s, H-17), 6.54 (1H, s, H-14), 6.01 (1H, d, J$_{3-4}$=9.8, H-3), 5.87 and 5.856 (2H, 2d J$_{AB}$=1.4, OCH$_2$O), 5.05 (1H, s, H-1), 3.77 (1H, d, J$_{4-3}$=9.8, H-4), 3.67 (3H, s, OCH$_3$), 3.57 (3H, s, OCH$_3$), 3.54 (1H, s, 2'-OH), 3.10 (2H, m, H-11β+H-8α), 2.94 (1H, m, H-10α), 2.60 (2H, m, H-8β+H-10β), 2.38 (1H, m, J=14 and 6.8, H-11α), 2.29 and 1.90 (2H, 2d, J$_{AB}$=16.6, CH$_2$CO$_2$), 2.03 (1H, m, H-6$_A$), 1.91 (1H, m, H-6$_B$), 1.75 (2H, m, CH$_2$-7), 1.7-1.1 (4H, m, 2×CH$_2$), 1.30 (3H, d, J$_{H-F}$=21.4, CH$_3$), 1.29 (3H, d, J$_{H-F}$=21.4, CH$_3$).

EXAMPLE 60

Preparation of (2'S)-4''-Chloro-4''-deoxy-epi-homoharringtonine

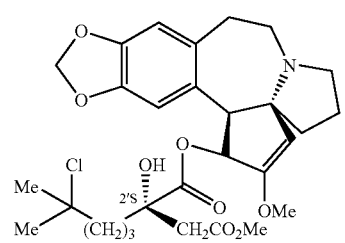

To a stirred solution of epi-homoharringtonine (100 mg, 0.18 mmol) in dry chloroform (2 ml) under nitrogen was added SOCl2 (131 µl, 1.8 mmol). After stirring at ambient temperature for 2 hours, was added a saturated sodium hydrogen carbonate solution (5 ml), the resulting aqueous layer was extracted with dichloromethane (3×5 ml) and the combined organic layers were dried over magnesium sulfate and evaporated to dryness to provide the expected compound (104 mg crude, 100%). The product thus obtained showed the following characteristics:

$^1$H NMR 400 MHz (CDCl$_3$) (δ ppm, J Hz): 6.64 (1H, s, H-17), 6.59 (1H, s, H-14), 5.95 and 5.87 (2H, 2d J$_{AB}$=1.2, OCH$_2$O), 5.94 (1H, d, J$_{3-4}$=9.8, H-3),5.04 (1H, s, H-1), 3.78 (1H, d, J$_{4-3}$=9.7, H-4), 3.67 (3H, s, OCH$_3$), 3.66 (3H, s, OCH$_3$), 3.58 (1H, s, 2'-OH), 3.11 (2H, m, H-11β+H-8α), 2.93 (1H, m, H-10α), 2.62 and 2.54 (2H, 2d, J$_{AB}$=16.5, CH$_2$CO$_2$), 2.60 (2H, m, H-8β+H-10β), 2.39 (1H, m, J=13.9 and 6.6, H-11α), 2.02 (1H, m, H-6$_A$), 1.90 (1H, m, H-6$_B$), 1.76 (2H, m, CH$_2$-7), 1.7-0.7 (6H, m, 3×CH$_2$), 1.53 (3H, s, CH$_3$), 1.52 (3H, s, CH$_3$).

EXAMPLE 61

Preparation of 4-methyl (2R)-2-hydroxy-2-(4-methyl-pent-3-enyl)succinate of (−)-cephalotaxine

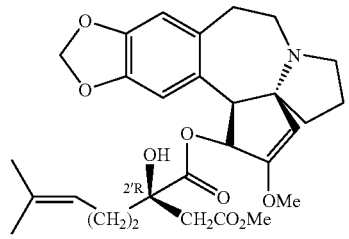

To a stirred solution of homoharringtonine (100 mg, 0.18 mmol) in dry pyridine (2 ml) under nitrogen was added POCl3 (170 µl, 1.8 mmol) at −5° C. After stirring at −5° C. for 20 hours and adjusting to pH 0.5 by addition of hydrochloric acid 50% (9 ml) the aqueous layer was washed with ether (3×10 ml). The resulting aqueous layer was alkalinized to pH 9.5 with ammonia 25% and was extracted with dichloromethane (5-10 ml). The combined organic layers were dried over magnesium sulfate and evaporated to dryness. The crude product thus obtained was purified by phase-reversed chromatography (octadecylsilane 12 µm (100 g), buffer pH 3/methanol, 45:55). After removal of methanol in vacuo the resulting aqueous layer was adjusted to pH 1.5 with hydrochloric acid 1N, washed with ether (3×10 ml), alkalinized to pH 10.6 with ammonia 25% and extracted with dichloromethane (5×10 ml). The combined organic layers were dried over magnesium sulfate and evaporated to dryness to provide the expected compound (20 mg; 21%). The product thus obtained showed the following characteristics:

$^1$H NMR 400 MHz (CDCl$_3$) (δ ppm, J Hz): 6.62 (1H, s, H-17), 6.54 (1H, s, H-14), 6.0 (1H, d, J$_{3-4}$=9.8, H-3), 5.88 and 5.83 (2H, 2d J$_{AB}$=1.4, OCH$_2$O), 5.06 (1H, s, H-1), 5.01 (1H, m, =CH), 3.78 (1H, d, J$_{4-3}$=9.8, H-4), 3.68 (3H, s, OCH$_3$), 3.58 (3H, s, OCH$_3$), 3.51 (1H, s, 2'-OH), 3.14 (2H, m, H-11β+H-8α), 2.96 (1H, m, H-10α), 2.39 (2H, m, H-8β+H-10β), 2.39 (1H, m, J=14.1 and 6.7, H-11α), 2.27 and 1.89 (2H, 2d, J$_{AB}$=16.4, CH$_2$CO$_2$), 2.1-1.9 (3H, m, CH$_2$-6+CH$_2$), 2.1-1.9 (3H, m, CH$_2$-7+CH$_2$), 1.66 (3H, s, CH$_3$), 1.56 (3H, s, CH$_3$), 1.42 (2H, m, CH$_2$).

EXAMPLE 62

Preparation of (2'R)-4'-(4-pentenyl)-4'-demethyl-homoharringtonine

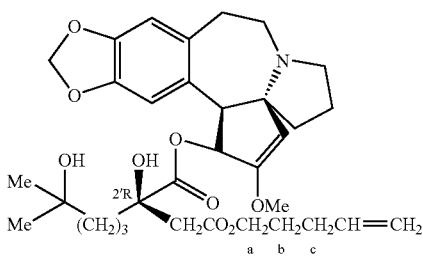

Sodium hydride 60% (7.1 mg, 0.177 mmol) was added to a solution of homoharringtonine (322 mg, 0.590 mmol) in 4-penten-1-ol (3.2 ml) and the resulting mixture was stirred at ambient temperature for 2 hours under argon. After adjusting to pH 1.9 by addition of hydrochloric acid 0.1N (11 ml), the aqueous layer was washed with ether (3×6 Ml). The resulting aqueous layer was alkalinized with ammonia 25% (five drops) and was extracted with dichloromethane (6×10 ml). The combined organic layers were dried over magnesium sulfate and evaporated to dryness (230 mg crude, 65%). The crude product thus obtained was purified by phase-reversed chromatography (octadecylsilane 12 µm (135 g), buffer pH 3/methanol, 50:50). After removal of methanol in vacuo the resulting aqueous layer was washed with ether (10 ml) and alkalinized to pH 9.5 with ammonia 25% (five drops) and extracted with dichloromethane (6×10 ml). The combined organic layers were dried over magnesium sulfate and evaporated to dryness to provide the expected compound (149 mg; 42%). The product thus obtained showed the following characteristics:

$^1$H NMR 400 MHz (CDCl$_3$) (δ ppm, J Hz): 6.62 (1H, s, H-17), 6.54 (1H, s, H-14), 5.98 (1H, d, J$_{3-4}$=9.8, H-3), 5.85 (2H, s, OCH$_2$O), 5.80 (1H, m, CH=), 5.05 (1H, s, H-1), 5.03 (2H, m, =CH$_2$), 3.98 (2H, m, CH$_2$-a), 3.77 (1H, d, J$_{4-3}$=9.8, H-4), 3.68 (3H, s, OCH$_3$) 3.52 (1H, s, 2'-OH), 3.12 (2H, m, H-11β+H-8α), 2.94 (1H, dt, J=11.2 and 6.9, H-10α), 2.58 (2H, m, H-8β+H-10β), 2.38 (1H, dd, J$_{AB}$=14.0, J=6.7, H-11α), 2.25 and 1.92 (2H, 2d, J$_{AB}$=16.3, CH$_2$CO$_2$), 2.09 (2H, q, J=7.2, CH$_2$-c), 2.03 (1H, m, H-6$_A$), 1.90 (1H, m, H-6$_B$), 1.75 (2H, m, CH$_2$-7), 1.67 (2H, qt, J=7.4, CH$_2$-b), 1.50-1.30 (6H, m, 3×CH$_2$), 1.29 (1H, s, 4"-OH), 1.18 and 1.19 (6H, 2s, 2×CH$_3$).

EXAMPLE 63

Preparation of (2'R)-4'-(dimethylamino-ethyl)-4'-demethyl-homoharring-tonine

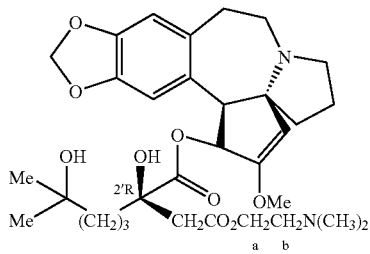

Sodium hydride 60% (5.8 mg, 0.145 mmol) was added to a solution of homoharringtonine (400 mg, 0.733 mmol) in N,N-dimethylethanol (4 ml) and the resulting mixture was stirred at ambient temperature for 2 hours under argon. After adjusting to pH 1.5 by addition of hydrocholric acid 0.1N (20 ml), the aqueous layer was washed with ether (3×8 ml). The resulting aqueous layer was alkalinized with ammonia 25% (pH=8-9) and was extracted with dichloromethane (6×10 ml). The combined organic layers were dried over magnesium sulfate and evaporated to dryness (quantitative). The crude product thus obtained was purified by phase-reversed chromatography (octadecylsilane 12 µm (135 g), buffer pH 3/methanol, 100:0 then95:5 ; 90:10 ; 80:20). After removal of methanol in vacuo the resulting aqueous layer was washed with ether (10 ml) and alkalinized to pH 9.5 with ammonia 25% and extracted with dichloromethane (6×10 ml). The combined organic layers were dried over magnesium sulfate and evaporated to dryness to provide the expected compound (266 mg; 60%). The product thus obtained showed the following characteristics:

$^1$H NMR 400 MHz (CDCl$_3$) (δ ppm, J Hz): 6.60 (1H, s, H-17), 6.54 (1H, s, H-14), 6.02 (1H, d, J$_{3-4}$=9.8, H-3), 5.84 (2H, s, OCH$_2$O), 5.04 (1H, s, H-1), 4.43 (1H, ddd, J=11.8, J=8.0, J=4.0, H-aα), 3.79 (1H, d, J$_{4-3}$=9.8, H-4), 3.74 (1H, m, H-aβ), 3.67 (3H, s, OCH$_3$), 3.12 (2H, m, H-11β+H-8α), 2.94 (1H, dt, J=11.2 and 6.9, H-10□), 2.58 (2H, m, H-8□+H-10□), 2.49 (1H, dd, J=12.6, J=8.0, J=4.3, H-b□), 2.37 (1H, dd, J$_{AB}$=14.3, J=6.7, H-11α), 2.34 (1H, m, H-6$_A$), 2.22 (6H, s, N(CH$_3$)$_2$), 2.22 and 2.11 (2H, 2d, J$_{AB}$=15.5, CH$_2$CO$_2$), 2.03 (1H, m, H-6$_B$), 1.89 (1H, ddd, J=12.1, J=7.7, J=4.3, H-bβ), 1.75 (2H, m, CH$_2$-7), 1.50-1.20 (7H, m, 3×CH$_2$ and 4"-OH), 1.19 and 1.18 (6H, 2s, 2×CH$_3$).

EXAMPLE 64

Preparation of (2'R)-4'-nonyl-4'-demethyl-homoharringtonine

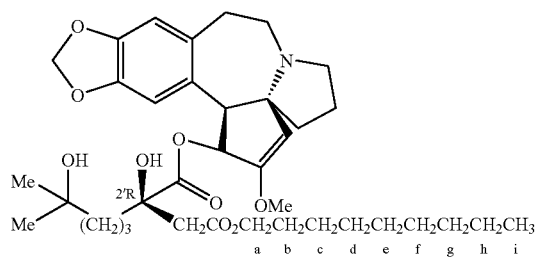

Sodium hydride 60% (8.9 mg, 0.223 mmol) was added to a solution of homoharringtonine (405 mg, 0.742 mmol) in n-nonanol (4 ml) and the resulting mixture was stirred at ambient temperature for 3 hours under argon. After adjusting to pH 1.3 by addition of hydrochloric acid 0.1N (13 ml), the aqueous layer was washed with petroleum ether (8 ml) and the resulting organic layer was extracted with hydrochloric acid 0.1 N (5 ml). This was repeated an other time. The combinated aqueous layers were washed with ether (8 ml) then were alkalinized to pH 9.6 with ammonia 25% (fifteen drops) and were extracted with dichloromethane (6×8 ml). The combined organic layers were dried over magnesium sulfate and evaporated to dryness (400 mg crude, 82%). The crude product thus obtained was purified by phase-reversed chromatography (octadecylsilane 12 µm (135 g), buffer pH 3/methanol, 20:80). After removal of methanol in vacuo the resulting aqueous layer was alkalinized to pH 9.7 with ammonia 25% and extracted with dichloromethane (6×10 ml). The combined organic layers were dried over magnesium sulfate and evaporated to dryness to provide the expected compound (256 mg; 52%) The product thus obtained showed the following characteristics:

$^1$H NMR 400 MHz (CDCl$_3$) (δ ppm, J Hz): 6.62 (1H, s, H-17), 6.54 (1H, s, H-14), 5.98 (1H, d, J$_{3-4}$=9.8, H-3), 5.86 (2H, s, OCH$_2$O), 5.05 (1H, s, H-1), 4.00 and 3.91 (2H, 2m, CH$_2$-a), 3.78 (1H, d, J$_{4-3}$=9.8, H-4), 3.68 (3H, s, OCH$_3$), 3.52 (1H, s, 2'-OH), 3.10 (2H, m, H-11β+H-8α), 2.95 (1H, m, H-10α), 2.60 (2H, m, H-8β+H-10β), 2.38 (1H, dd, J=14.1 and 6.7, H-11α), 2.24 and 1.92 (2H, 2d, J$_{AB}$=16.3, CH$_2$CO$_2$), 2.03 (1H, m, H-6$_A$), 1.92 (1H, m, H-6$_B$), 1.77 (2H, m, CH$_2$-7), 1.56 (2H, m, CH$_2$-b), 1.50-1.22 (16H, m, CH$_2$-c,d,e,f,g,h and 3×CH$_2$), 1.19 (6H, s, 2×CH$_3$), 0.88 (3H, t, J=6.8, CH$_3$-i).

EXAMPLE 65

Preparation of (2'R)-4'-pentyl-4'-demethyl-homoharringtonine

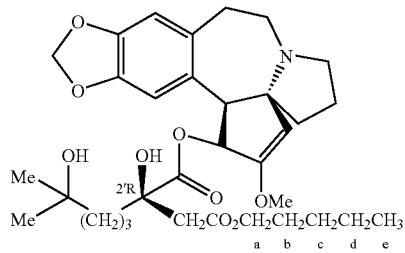

Sodium hydride 60% (10.0 mg, 0.250 mmol) was added to a solution of homoharringtonine (416 mg, 0.762 mmol) in n-pentanol (4.2 ml) and the resulting adjusting to pH 1.8 by addition of hydrochloric acid 0.1N (14 ml), the aqueous alkalinized with ammonia 25% (pH=9.5) and was extracted with dichloromethane mixture was stirred at ambient temperature for 2 hours under argon. After (6×10 ml). The combined organic layers were dried over magnesium sulfate and was purified by phase-reversed chromatography (octadecylsilane 12 µm (130 g), buffer pH 3/methanol, 40:60). After removal of methanol in vacuo the resulting alkalinized with ammonia 25% (pH=9.5) and was extracted with dichloromethane dichloromethane (6×10 ml). The combined organic layers were dried over magnesium sulfate and evaporated to dryness to provide the expected compound was purified by phase-reversed chromatography (octadecylsilane 12 µm (130 g), $^1$H NMR 400 MHz (CDCl3) (δ ppm, J Hz): 6.62 (1H, s, H-17), 6.55 (1H, s, H-14), (1H, d, J$_{3-4}$=9.7, H-3), 5.86 (2H, s, OCH$_2$O), 5.05 (1H, s, H-1), 4.00 and 3.92 (2H, 2m, C<u>H</u>$_2$-a), 3.78 (1H, d, J<u>4-3</u>=9.2, H-4), 3.68 (3H, s, OCH$_3$), 3.53 (1H, s, 2'-OH), 3.12 (2H, m, H-11β+H-8α), 2.96 (1H, m, H-10α), 2.61 (2H, m, H-8β+H-10β), 2.41 (1H, m, H-11α), 2.25 and 1.95 (2H, 2d, J$_{AB}$=16.2, C<u>H</u>$_2$CO$_2$), 2.03 (1H, m, H-6$_A$), 1.92 (1H, m, H-6$_B$), 1.78 (2H, m, CH$_2$-7); 1.57 (2H, m, CH$_2$-b), 1.50-1.22 (10H, m, CH$_2$-c,d and 3×CH$_2$), 1.19 (6H, s, 2×CH$_3$), 0.90 (3H, t, J=6.9, CH$_3$-e)

EXAMPLE 66

Preparation of (2'R)-4'-heptyl-4'-demethyl-homoharringtonine

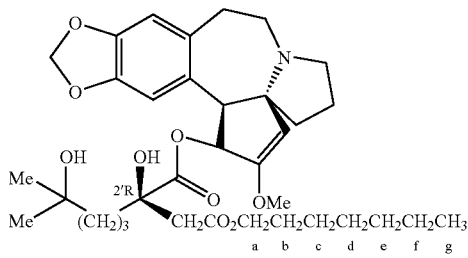

Sodium hydride 60% (8.8 mg, 0.220 mmol) was added to a solution of homoharringtonine (400 mg, 0.733 mmol) in n-heptanol (4.0 ml, 28.3 mmol) and the resulting mixture was stirred at room temperature for 3 h 30 under nitrogen. After adjusting to pH 1.8 by addition of hydrochloric acid 0.1N (15 ml), the aqueous layer was washed with petroleum ether (3×10 ml). The resulting aqueous layer was alkalinized with ammonia 25% (pH=9.3) and was extracted with dichloromethane (10×10 ml). The combined organic layers were dried over magnesium sulfate and evaporated to dryness (306 mg crude, 65.9%). The crude product thus obtained was purified by phase-reversed chromatography (octadecylsilane 12 μm (130 g), buffer pH 3/methanol, 25:75). After removal of methanol in vacuo the resulting aqueous layer was alkalinized to pH 9-10 with ammonia 25% and extracted with dichloromethane (6×10 ml). The combined organic layers were dried over magnesium sulfate and evaporated to dryness to provide the expected compound (183 mg, 40%). The product thus obtained showed the following characteristics:

$^1$H NMR 400 MHz (CDCl$_3$) (δ ppm, J Hz): 6.62 (1H, s, H-17), 6.54 (1H, s, H-14), 5.98 (1H, d, J=9.8, H-3), 5.86 (2H, s, OCH$_2$O), 5.05 (1H, s, H-1), 4.00 and 3.91 (2H, 2dt, J$_{AB}$=10.7 and J$_{a-b}$=6.8, C<u>H</u>$_2$-a), 3.78 (1H, d, J=9.7, H-4), 3.68 (3H, s, OCH$_3$), 3.52 (1H, s, 2'-OH), 3.11 (2H, m, H-11β+H-8α), 2.94 (1H, m, H-10α), 2.60 (2H, m, H-8β+H-10α), 2.38 (1H, dd, J=14.0 and J=6.8, H-11α), 2.24 and 1.91 (2H, 2d, J$_{AB}$32 16.3, C<u>H</u>$_2$CO$_2$), 2.02 (1H, m, H-6$_A$), 1.89 (1H, m, H-6$_B$), 1.76 (2H, m, CH$_2$-7), 1.58 (2H, m, CH$_2$-b), 1.50-1.10 (14H, m, CH$_2$-c-f and 3×CH$_2$), 1.19 (3H, s, CH$_3$), 1.13 (3H, s, CH$_3$), 0.89 (3H, t, J=6.8, CH$_3$-g).

EXAMPLE 67

Preparation of (2'R)-4'-octyl-4'-demethyl-homoharringtonine

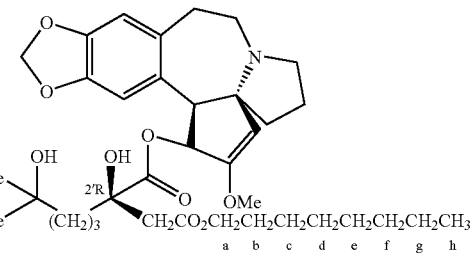

Sodium hydride 60% (9.0 mg, 0.225 mmol) was added to a solution of homoharringtonine (413 mg, 0.757 mmol) in n-octanol (4.0 ml, 25.4 mmol) and the resulting mixture was stirred at room temperature for 2 hours under nitrogen. After adjusting to pH 1.4 by addition of hydrochloric acid 0.1N (40 ml), the aqueous layer was washed with petroleum ether (4×20 ml). The organic layers were combined then extracted two times by hydrochloric acid 0.1N (10 ml). The resulting aqueous lay were combined and were alkalinized with ammonia 25% (pH=9.0) then were extracted with dichloromethane (4×10 ml). The combined organic layers were dried over magnesium sulfate and evaporated to dryness (410 mg crude). The crude product thus obtained was purified by phase-reversed chromatography (octadecylsilane 12 μm (130 g), buffer pH 3/methanol, 23:77). After removal of methanol in vacuo the resulting aqueous layer was alkalinized to pH 9-10 with ammonia 25% and extracted with dichloromethane (4×15 ml). The combined organic layers were dried over magnesium sulfate and evaporated to dryness to provide the expected compound (249 mg, 51%). The product thus obtained showed the following characteristics:

$^1$H NMR 400 MHz (CDCl$_3$) (δ ppm, J Hz): 6.62 (1H, s, H-17), 6.54 (1H, s, H-14), 5.98 (1H, d, J=9.7, H-3), 5.86 (2H, s, OCH$_2$O), 5.05 (1H, s, H-1), 3.99 and 3.92 (2H, 2m, C<u>H</u>$_2$-a), 3.78 (1H, d, J=9.8, H-4), 3.68 (3H, s, OCH$_3$), 3.11 (2H, m, H-11β+H-8α), 2.93 (1H, m, H-10α), 2.59 (2H, m, H-8β+H-10β), 2.38 (1H, m, H-11α), 2.24 and 1.91 (2H, 2d, J$_{AB}$=16.3, C<u>H</u>$_2$CO$_2$), 2.02 (1H, m, H-6$_A$), 1.91 (1H, m, H-6$_B$), 1.77 (2H, m, CH$_2$-7), 1.60-1.10 (16H, m, CH$_2$-b-g and 3×CH$_2$), 1.19 (6H, s, 2×CH$_3$), 0.88 (3H, t, J=6.8, CH$_3$-h).

EXAMPLE 68

Preparation of (2'R)-4'-decyl-4'-demethyl-homoharringtonine

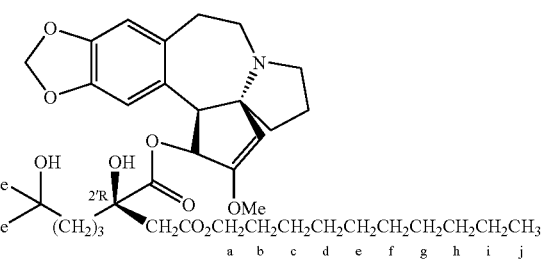

Sodium hydride 60% (6.6 mg, 0.165 mmol) was added to a solution of homoharringtonine (300 mg, 0.550 mmol) in n-decanol (6.0 ml, 31.4 mmol) and the resulting mixture was stirred at room temperature for 2 hours under nitrogen. The solution was alkalinized with ammonia 25% (pH=10.0) and was extracted with dichloromethane (3×20 ml). The combined organic layers were dried over magnesium sulfate and evaporated to dryness. The crude product thus obtained was purified by normal phase chromatography (silicagel 15-40 µm (10 g, $CH_2Cl_2$/methanol 100:0, 95:5, 90:10, 80:20) to obtain a product which was purified by phase-reversed chromatography (octadecylsilane 12 µm (130 g), buffer pH 3/methanol, 15:85). After removal of methanol in vacuo the resulting aqueous layer was alkalinized to pH 9.5 with ammonia 25% and extracted with dichloromethane (6×10 ml). The combined organic layers were dried over magnesium sulfate and evaporated to dryness to provide the expected compound (164 mg, 44%). The product thus obtained showed the following characteristics:

$^1$H NMR 400 MHz ($CDCl_3$) (δ ppm, J Hz): 6.63 (1H, s, H-17), 6.58 (1H, s, H-14), 6.00 (1H, d, J=9.7, H-3), 5.98 (2H, s, $OCH_2O$), 5.04 (1H, s, H-1), 4.01 and 3.90 (2H, 2m, $CH_2$-a), 3.79 (1H, H-4), 3.72 (3H, s, $OCH_3$), 3.55 (1H, s, 2'-OH), 3.16 (2H, m, H-11β+H-8α), 3.02 (1H, m, H-10α), 2.64 (2H, m, H-8β+H-10β), 2.44 (1H, m, H-11α), 2.28 (1H, d, $J_{AB}$=15,0, $CH_A$-$CO_2$), 1.97 (3H, m, $CH_2$-6, $CH_B CO_2$), 1.82 (2H, m, $CH_2$-7), 1.56 (2H, m, $CH_2$-b), 1.50-1.10 (6H, m, 3×$CH_2$), 1.26 (14H, m, $CH_2$-c to $CH_2$-i), 1.19 (3H, s, $CH_3$), 1.18 (3H, s, $CH_3$), 0.88 (3H, t, J=6.8, $CH_3$-j).

EXAMPLE 69

Preparation of (2'R)-4'-(methyl-2-butyl)-4'-demethyl-homoharringtonine

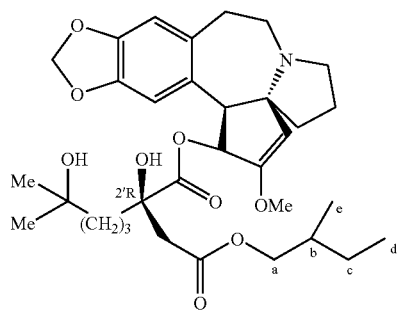

Sodium hydride 60% (8.9 mg, 0.222 mmol) was added to a solution of homoharringtonine (404 mg, 0.740 mmol) in 2-methyl-1-butanol (4.0 ml, 37 mmol) and the resulting mixture was stirred at room temperature for 3 hours under argon. After adjusting to pH 1.7 by addition of hydrochloric acid 0.1N (13 ml), the aqueous layer was washed with ether (3×8 ml). The solution was alkalinized with ammonia 25% (pH=9.7) and was extracted with dichloromethane (7×10 ml). The combined organic layers were dried over magnesium sulfate and evaporated to dryness (270 mg). The crude product thus obtained was purified by phase-reversed chromatography (octadecylsilane 12 µm (130 g), buffer pH 3/methanol, 42:58). After removal of methanol in vacuo the resulting aqueous layer was alkalinized to pH 9.0 with ammonia 25% and extracted with dichloromethane (6×10 ml). The combined organic layers were dried over magnesium sulfate and evaporated to dryness to provide the expected compound (227 mg, 51%). The product thus obtained showed the following characteristics:

$^1$H NMR 400 MHz ($CDCl_3$) (δ ppm, J Hz): 6.62 (1H, s, H-17), 6.55 (1H, s, H-14), 5.98 (1H, d, J=9.8, H-3), 5.86 (2H, s, $OCH_2O$), 5.05 (1H, s, H-1), 3.93 and 3.72 (2 dd, $J_{AB}$=10.3 and J=6.6) and 3.78 (m, 2H, $CH_2$-a), 3.82 (1H, d, J=9.8, H-4), 3.68 (3H, s, $OCH_3$), 3.51 (1H, s, 2'-OH), 3.10 (2H, m, H-11β+H-8α), 2.96 (1H, m, H-10α), 2.60 (2H, m, H-8β+H-10β), 2.38 (1H, dd, J=15.0 and J=7.1, H-11α), 2.26 and 1.93 (2H, 2d, $J_{AB}$=16.5, $CH_2$—$CO_2$), 1.91 (1H, m, H-6β), 1.76 (2H, m, $CH_2$-7), 1.70-1.10 (9H, m, $CH_2$-c, H-b, 3×$CH_2$), 1.19 (6H, s, 2×$CH_3$), 0.90 (6H, m, $CH_3$-d,e).

EXAMPLE 70

Preparation of (2'R)-4'-(pent-2-ynyl)-4'-demethyl-homoharringtonine

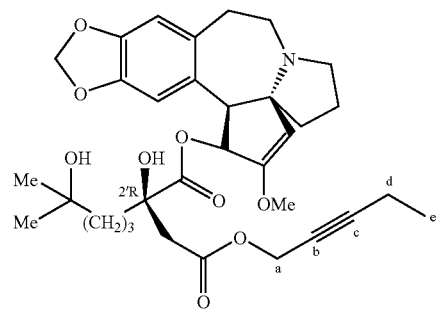

Sodium hydride 60% (11.8 mg, 0.295 mmol) was added to a solution of homoharringtonine (402 mg, 0.737 mmol) in 2-pentyn-1-ol (2.0 ml, 21.7 mmol) and the resulting mixture was stirred at room temperature for 3 h 30 under nitrogen. After adjusting to pH 1.5 by addition of hydrochloric acid 0.1N (14 ml), the aqueous layer was washed with ether (3×8 ml). The solution was alkalinized with ammonia 25% (pH=9.5) and was extracted with dichloromethane (6×10 ml). The combined organic layers were dried over magnesium sulfate and evaporated to dryness (334 mg). The crude product thus obtained was purified by phase-reversed chromatography (octadecylsilane 12 µm (130 g), buffer pH 3/methanol, 57:43). After removal of methanol in vacuo the resulting aqueous layer was alkalinized to pH 8.5 with ammonia 25% and extracted with dichloromethane (4×10 ml). Then the resulting aqueous layer was alkalinized to pH 9.5 with ammonia 25% and extracted with dichloromethane (3×10 ml). The combined organic layers were dried over magnesium sulfate and evaporated to dryness to provide the expected compound (192 mg, 43.6%). This product thus obtained was purified again by phase-reversed chromatography (octadecylsilane 12 µm (130 g), buffer pH 3/methanol, 55:45). After removal of methanol in vacuo the resulting aqueous layer was alkalinized to pH 8-9 with ammonia 25% and extracted with dichloromethane (6×10 ml). The combined organic layers were dried over magnesium sulfate and evaporated to dryness to provide the expected compound (153 mg, 35%).

The product thus obtained showed the following characteristics:

$^1$H NMR 400 MHz ($CDCl_3$) (δ ppm, J Hz): 6.62 (1H, s, H-17), 6.56 (1H, s, H-14), 6.00 (1H, d, J=9.8, H-3), 5.90 and 5.85 (2H, 2s, $OCH_2O$), 5.05 (1H, s, H-1), 4.02 (2H, m, $CH_2$-a), 3.78 (1H, d, J=9.7, H4), 3.68 (3H, s, $OCH_3$), 3.54 (1H, s, 2'-OH), 3.11 (2H, m, H-11β+H-8α), 2.95 (1H, m, H-10α), 2.41 (2H, m, H-8β+H-10β), 2.40 (3H, m, $CH_2$-d, H-11α), 2.27 and 1.94 (2H, 2d, $J_{AB}$=16.4, $CH_2$—$CO_2$), 2.02 (1H, m, H-6$_A$), 1.92 (1H, m, H-6$_B$), 1.78 (5H, m, $CH_2$-7 and $CH_3$-e), 1.42 (6H, m, 3×$CH_2$), 1.19 (6H, s, 2×$CH_3$).

EXAMPLE 71

Preparation of (2'R)-4'-hexylamino-4'-demethoxy-homoharringtonine

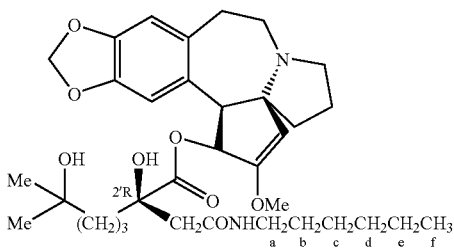

Step One

To a stirred mixture of 4'-demethyl-anhydro-homoharringtonine (830 mg, 1.616 mmol) resulting from Example 2 in dry dichloromethane (6 ml) was added at room temperature the pentafluorophenol (892 mg, 4.847 mmol). A solution of dicylohexylcarbodiimide (500 mg, 2.424 mmol) in dry dichloromethane (6 ml) was added at the above mixture. After stirring at room temperature for 2 hours, the reaction mixture was poured in sodium hydrogen carbonate solution (10%) (10 ml) and was extracted with dichloromethane (4×10 ml). Then the combined organic layers after drying over magnesium sulfate were evaporated to dryness to provide the expected compound (1.2 g, 100%). The 4'-pentafluorophenyl-4'-demethyl-anhydro-homoharringtonine thus obtained showed the following characteristics:

$^1$H NMR 400 MHz (CDCl$_3$) (δ ppm, J Hz): 6.53 (1H, s, H-17), 6.52 (1H, s, H-14), 5.95 (1H, d, J=9.5, H$_3$), 5.82 and 5.71 (2H, 2s, OCH$_2$O), 5.03 (1H, s, H-1), 3.91 (1H, d, J=9.6, H-4), 3.73 (3H, s, OCH$_3$), 3.24 (3H, m, H-11β, 8α, 10α), 2.78 (2H, m, H-8β+H-10β), 2.48 and 1.75 (2H, 2d, $J_{AB}$=14.5, $CH_2CO_2$), 2.40 (1H, m, H-11α), 2.03 (1H, m, H-6$_A$), 1.90 (1H, m, H-6$_B$), 1.75 (2H, m, $CH_2$-7), 170-1.10 (6H, m, 3×$CH_2$), 1.13 (3H, s, $CH_3$), 1.04 (3H, s, $CH_3$).

Step Two

To a stirred mixture of 4'-pentafluorophenyl-4'-demethyl-anhydro-homoharringtonine (1.165 g, 1.320 mmol) in dry tetrahydrofuran (11.6 ml) was added at room temperature hexylamine (0.260 ml, 1.968 mmol). After stirring at room temperature for 1 hour, the reaction mixture was poured in hydrochloric acid 1N (20 ml) and was washed with ether (2×15 ml). The aqueous layer was alkalinized with ammonia 25% (pH=8-9) and was extracted with dichloromethane (3×20 ml). The combined organic layers were dried over magnesium sulfate and evaporated to dryness (665 mg). The crude product thus obtained was purified by chromatography (silicagel 15-40 μm (26 g), $CH_2Cl_2$/methanol 100:0, 99:1, 98:2, 95:5, 90:10) to provide the expected 4'-hexylamino-4'-demethoxy-anhydro-homo harringtonine (549 mg, 70%).

$^1$H NMR 400 MHz (CDCl$_3$) (δ ppm, J Hz): 6.67 (1H, s, H-17), 6.59 (1H, t, NH), 6.54 (1H, s, H-14), 5.89 (1H, d, H$_3$), 5.88 (2H, s, OCH$_2$O), 5.06 (1H, s, H-1), 3.78 (1H, d, J=9.7, H-4), 3.71 (3H, s, OCH$_3$), 3.24 (1H, m, H-11α), 3.09 and 2.84 (2H, 2m, $CH_2$-a), 3.09 (1H, m, H-8α), 2.95 (1H, dt, J=11.0 and J=6.8, 10α), 2.07 and 1.73 (2H, 2d, $J_{AB}$=14.9, $CH_2$CON), 2.03 (1H, m, H-6$_A$), 1.90 (1H, m, H-6$_B$), 1.74 (2H, m, $CH_2$-7), 1.70-1.20 (14 H, m, 3×$CH_2$, $CH_2$ (b-e)), 1.19 (3H, s, $CH_3$), 1.04 (3H, s, $CH_3$), 0.87 (3H, t, J=6.2, $CH_3$f).

Step Three

To a stirred solution of 4' hexylamino-4'-demethoxy-anhydro-homoharringtonine (549 mg, 0.92 mmol) in dry dichloromethane (2.8 ml) under nitrogen was added at −10° C. a commercial solution of hydrobromic acid in acetic acid (1.65 ml, 8.28 mmol, HBr 30% w/w). After stirring at −10° C. for 3 hours, was added water (25 ml) and the temperature was raised to 20° C. After stirring at 20° C. for 3 h 30, was added a sodium carbonate solution (0.76 M, 17.4 ml) up to pH 8-9. The resulting aqueous layer was extracted with dichloromethane (3×20 ml) and the combined organic layers were dried over magnesium sulfate and evaporated to dryness. The resulting crude product was purified by phase-reversed chromatography (octadecylsilane 12 μm (130 g), buffer pH 3/methanol, 42:58, 30:70, and 0:100). After removal of methanol in vacuo the resulting aqueous layer was alkalinized to pH 9-10 with ammonia 25% and extracted with dichloromethane (6×10 ml). The combined organic layers were dried over magnesium sulfate and evaporated to dryness to provide the expected compound (237 mg, 42%).The product thus obtained showed the following characteristics:

$^1$H NMR 400 MHz (CDCl$_3$) (δ ppm, J Hz): 6.68 (1H, s, H-17), 6.59 (1H, s, H-14), 5.92 (1H, d, J=9.9, H-3), 5.90 and 5.85 (2H, 2d, $J_{AB=}$1.2, OCH$_2$O), 5.60 (1H, t, NH), 5.05 (1H, s, H-1), 4.26 (1H, s, 2'-OH), 3.78 (1H, d, J=9.7, H-4), 3.67 (3H, s, OCH$_3$), 3.13 (4H, m, H-11β, 8α and CH$_2$-a), 2.96 (1H, m, H-10α), 2.60 (2H, m, H-8β+H-10β), 2.41 (1H, dd, $J_{AB}$=14.3, J=6.9, H-11α), 2.01 (1H, m, H-6$_A$), 1.93 and 1.69 (2H, 2d, $J_{AB}$=14.8, $CH_2CO_2$), 1.89 (1H, m, H-6$_B$), 1.71 (2H, m, $CH_2$-7), 1.50-1.10 (14H, m, 3×$CH_2$, $CH_2$-(b-e)), 1.18 (6H, s, 2×$CH_3$), 0.88 (3H, t, J=6.7, $CH_3$f).

EXAMPLE 72

Preparation of (2'R)-4'-p-methylbenzyl-4'-demethyl-homoharringtonine

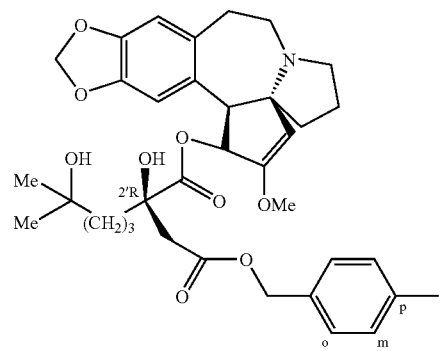

Sodium hydride 60% (11.5 mg, 0.287 mmol) was added to a solution of homoharringtonine (386 mg, 0.707 mmol) in 4-methylbenzyl alcohol (5.2 g, 42,5 mmol) at 60° C. and the resulting mixture was stirred at 60° C. for 45 min. under nitrogen. After adjusting to pH 1.4 by addition of hydrochloric acid 0.1N (30 ml), the aqueous layer was washed with ether (7×20 ml). The combined organic layers were extracted by hydrochloric acid 0.1N (2×10 ml). The combined acid aqueous layers were alkalinized with ammonia 25% (pH=8.4) and were extracted with dichloromethane (5×20 ml). The combined organic layers were dried over magnesium sulfate and evaporated to dryness. The crude product thus obtained was purified by phase-reversed chromatography (octadecylsilane 12 µm (130 g), buffer pH 3/methanol, 40:60). After removal of methanol in vacuo the resulting aqueous layer was alkalinized to pH 9.0 with ammonia 25% and extracted with dichloromethane (4×15 ml). The combined organic layers were dried over magnesium sulfate and evaporated to dryness to provide the expected compound (141 mg, 31%). The product thus obtained showed the following characteristics:

$^1$H NMR 400 MHz (CDCl$_3$) (δ ppm, J Hz): 7.22 (2H, d, J=8.1, Ph), 7.17 (2H, d, J=8.0, Ph), 6.61 (1H, s, H-17), 6.44 (1H, s, H-14), 5.96 (1H, d, J=9.8, H-3), 5.78 and 5.67 (2H, 2d, J=1.3, OCH$_2$O), 5.05 and 4.89 (2H, 2d, J=12.2, CH$_2$Ph), 5.05 (1H, s, H-1), 3.71 (1H, d, J=9.8, H-4), 3.67 (3H, s, OCH$_3$), 3.52 (1H, s, 2'-OH), 3.09 (2H, m, H-11β+H-8α), 2.94 (1H, m, H-10α), 2.59 (2H, m, H-8β+H-10β), 2.37 (1H, dd, H-11α), 2.35 (3H, s, CH$_3$), 2.29 and 1.90 (2H, 2d, J$_{AB}$=16.4, CH$_2$CO$_2$), 2.00 (1H, m, H-6$_A$), 1.88 (1H, m, H-6$_B$), 1.75 (2H, m, CH$_2$-7), 1.50-1.10 (6H, m, 3×CH$_2$), 1.18 (6H, 2s, 2×CH$_3$).

EXAMPLE 73

Preparation of (2'R)-4'-m-methylbenzyl-4'-demethyl-homoharringtonine

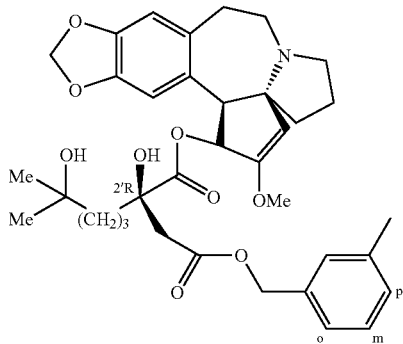

Sodium hydride 60% (9 mg, 0.225 mmol) was added to a solution of homoharringtonine (401 mg, 0.735 mmol) in 3-methylbenzyl alcohol (4.4 ml, 36.5 mmol) and the resulting mixture was stirred at room temperature for 1 h 30 under argon. After adjusting to pH 1.7 by addition of hydrochloric acid 0.1N (20 ml), the aqueous layer was washed with ether (5×20 ml). The combined organic layers were extracted by hydrochloric acid 0.1N (2×10 ml). The combined acid aqueous layers were alkalinized with ammonia 25% (pH=8.2) and were extracted with dichloromethane (7×15 ml). The combined organic layers were dried over magnesium sulfate and evaporated to dryness. The crude product thus obtained was purified by phase-reversed chromatography (octadecylsilane 12 µm (130 g), buffer pH 3/methanol, 40:60). After removal of methanol in vacuo the resulting aqueous layer was alkalinized to pH 9.0 with ammonia 25% and extracted with dichloromethane (4×15 ml). The combined organic layers were dried over magnesium sulfate and evaporated to dryness to provide the expected compound (213 mg, 45.6%). The product thus obtained showed the following characteristics:

$^1$H NMR 400 MHz (CDCl$_3$) (δ ppm, J Hz): 7.25 (1H, m, Ph), 7.12 (3H, m, Ph), 6.61 (1H, s, H-17), 6.43 (1H, s, H-14), 5.97 (1H, d, J=9.8, H-3), 5.78 and 5.66 (2H, 2d, J$_{AB}$=1.3, OCH$_2$O), 5.06 and 4.89 (2H, 2d, J$_{AB}$=12.5, CH$_2$Ph), 5.05 (1H, s, H-1), 3.71 (1H, d, J=9.8, H-4), 3.68 (3H, s, OCH$_3$), 3.53 (1H, s, 2'-OH), 3.09 (2H, m, H-11β+H-8α), 2.94 (1H, m, H-10α), 2.59 (2H, m, H-8β+H-10β), 2.37 (1H, m, H-11α), 2.36 (3H, s, CH$_3$), 2.30 and 1.91 (2H, 2d, J$_{AB}$=16.3, CH$_2$CO$_2$), 2.01 (1H, m, H-6$_A$), 1.89 (1H, m, H-6$_B$), 1.76 (2H, m, CH$_2$-7), 1.50-1.10 (6H, m, 3×CH$_2$), 1.18 (6H, 2s, 2×CH$_3$).

EXAMPLE 74

Preparation of (2'R)-4'-(5-hydroxypentyl)-4'-demethyl-homo harringtonine

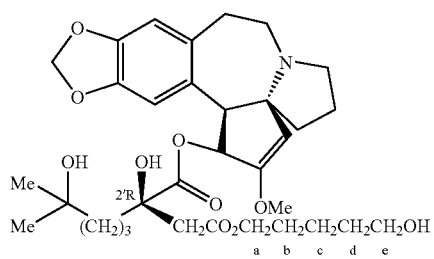

Sodium hydride 60% (44 mg, 1.10 mmol) was added by portion of 0.2 eq. all 15 min. to a solution of homoharringtonine (500 mg, 0.916 mmol) in 1,5-pentanediol (5.0 ml, 47.7 mmol) and the resulting mixture was stirred at room temperature for 2 h 15 under nitrogen. After adjusting to pH 2.1 by addition of hydrochloric acid 0.1N (23 ml), the aqueous layer was washed with ether (3×15 ml). The aqueous layer was alkalinized with ammonia 25% (pH=9.0) and was extracted with dichloromethane (6×15 ml). The combined organic layers were dried over magnesium sulfate and evaporated to dryness. The crude product thus obtained was purified by phase-reversed chromatography (octadecylsilane 12 µm (130 g), buffer pH 3/methanol, methanol, 70:30 to 20:80). After removal of methanol in vacuo the resulting aqueous layer was alkalinized to pH 9.0 with ammonia 25% and extracted with dichloromethane (4×20 ml). The combined organic layers were dried over magnesium sulfate and evaporated to dryness to provide the expected compound (245 mg, 43.3%). The product thus obtained showed the following characteristics:

$^1$H NMR 400 MHz (CDCl$_3$) (δ ppm, J Hz): 6.62 (1H, s, H-17), 6.54 (1H, s, H-14), 5.98 (1H, d, J=9.5, H-3), 5.86 (2H, s, OCH$_2$O), 5.06 (1H, s, H-1), 3.99 (2H, m, CH$_2$-a), 3.78 (1H, d, J=9.8, H-4), 3.68 (3H, s, OCH$_3$), 3.66 (2H, m, CH$_2$-e), 3.10 (2H, m, H-11β+H-8α), 2.94 (1H, dt, J=11.1 and J=6.9, H-10α), 2.60 (2H, m, H-8β+H-10β), 2.38 (1H, dd, J=14.0 and J=6.7, H-11α), 2.25 and 1.91 (2H, 2d, J$_{AB}$=16.2, CH$_2$CO$_2$), 2.02 (1H, m, H-6$_A$), 1.90 (1H, m, H-6$_B$), 1.75 (2H, m, CH$_2$-7), 1.70-1.10 (12H, m, 3×CH$_2$, CH$_2$-(b-d)), 1.19 (3H, s, CH$_3$), 1.18 (3H, s, CH$_3$).

EXAMPLE 75

Preparation of (2'R)-(4'-²H₃)homoharringtonine, from (2'R)-2',4''-anhydro-(4'-²H₃)-homoharringtonine

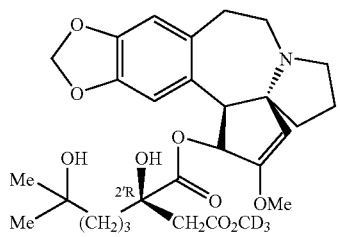

Step One

To a stirred mixture of 4'-demethyl-anhydro-homoharringtonine (180 mg, 0.35 mmol) resulting from Example 2 in dry dichloromethane (1.3 ml) was added at 0° C. triethylamine (49 µl, 0.35 mmol) and dropwise 2,4,6-trichlorobenzoyl chloride (55 µl, 0.35 mmol). After stirring at 0° C. during 10 minutes then at room temperature during 2.5 hours a solution of 4-dimethylaminopyridine (86 mg, 0.70 mmol) and methyl-d3 alcohol d (14 µl, 0.35 mmol) in dry dichloromethane (1.3 ml) was added. After stirring at room temperature for 19 hours, the reaction mixture was evaporated to dryness. The resulting crude product was purified by column chromatography (silica 15-40 µm (16 g), dichloromethane then dichloromethane/AcOEt, 70:30 to 0:100) to provide the expected compound (110 mg, 60%). The (2'R)-2',4''-anhydro-(4'-²H₃)-homoharringtonine thus obtained showed the following characteristics:

¹H NMR 400 MHz (CDCl₃) (δ ppm, J Hz): 6.61 (1H, s, H-17), 6.58 (1H, s, H-14), 5.91 (1H, d, J=9.3, H-3), 5.86 et 5.79 (2H, 2d, $J_{AB}$=1.4, OCH₂O), 5.04 (1H, s, H-1), 3.79 (1H, d, J=9.7, H-4), 3.70 (3H, s, 2-OCH₃), 3.12 (2H, m, H-11β and 8α), 2.96 (1H, m, H-10α), 2.60 (2H, m, H-8β and 10β), 2.37 (1H, dd, J=14.1 and 6.7, H-11α), 2.13 et 1.66 (2H, 2d, $J_{AB}$=14.2, CH₂CO₂), 2.02 (1H, m, H-6$_A$), 1.90 (1H, m, H-6$_B$), 1.76 (2H, m, CH₂-7),1.7-1.2 (6H, m, 3×CH₂), 1.11 (3H, J s, CH₃), 1.04 (3H, s, CH₃).

Step Two

To a stirred solution of (2'R)-2',4''-anhydro-(4'-²H₃)-homoharringtonine (85 mg, 0.16 mmol) in dry dichloromethane (0.5 ml) under nitrogen was added at −10° C. a commercial solution of hydrobromic acid in acetic acid (0.287 ml, 1.44 mmol, HBr 30% w/w). After stirring at −10° C. for 3 hours, the reaction mixture was poured in water (180 ml) cooled at 0° C. The mixture was stirred at −10° C. during 10 min then at room temperature for 3 hours. After this time was added a sodium carbonate solution (0.76 M) up to pH 9. The resulting aqueous layer was extracted with dichloromethane (4×20 ml) and the combined organic layers were dried over magnesium sulfate and evaporated to dryness. The crude product thus obtained was purified by phase-reversed chromatography (octadecylsilane 12 µm, buffer pH 3/acetonitrile, 90/10). The resulting aqueous layer was alkalinized to pH 9 with ammonia 25% and extracted with dichloromethane. The combined organic layers were evaporated to dryness to provide the expected product (60 mg, 68%). The product thus obtained showed the following characteristics:

¹H NMR 400 MHz (CDCl₃) (δ ppm, J Hz): 6.62 (1H, s, H-17), 6.55 (1H, s, H-14), 6.00 (1H, d, J=9.8, H3), 5.87 (2H, s, OCH₂O), 5.05 (1H, s, H-1), 3.78 (1H, d, J=9.8, H-4), 3.68 (3H, s, OMe), 3.53 (1H, s, 2'-OH), 3.10 (2H, m, H-11β and 8α), 2.94 (1H, m, H-10α), 2.60 (2H, m, H-8β and 10β), 2.38 (1H, dd, J=13.7 and 6.6, H-11α), 2.26 and 1.91 (2H, 2d, $J_{AB}$=16.5. CH₂CO₂), 2.02 (1H, m, H-6$_A$), 1.91 (1H, m, H-6$_B$), 1.76 (2H, m, CH₂-7), 1.5-1.1 (6H, m, 3×CH₂), 1.19 (6H, s, 2×CH₃).

Preparation of (2'R)-(4'-²H₃)homoharringtonine, from homoharringtonine

Sodium hydride 60% (2.1 mg, 52.5 µmol) was added to a solution of homoharringtonine (105 mg, 0.192 mmol) in methyl-d₃ alcohol (390 µl, 9.64 mmol) and the resulting mixture was stirred at room temperature for 2 hours. After addition water (8 ml), the aqueous layer was alkalinized with ammonia 25% (pH=10), then was extracted with dichloromethane (4×10 ml). The combined organic layers were dried over magnesium sulfate and evaporated to dryness to provide 90 mg of crude product with a purity of expected product of 88% and 1.9 % of homoharringtonine. The reaction was started again twice with this crude product to provide 56 mg, 53%, with a purity of expected product of 99.96% and 0.04% of homoharringtonine.

EXAMPLE 76

Preparation of (2'R)-(4'-²H)homoharringtonine

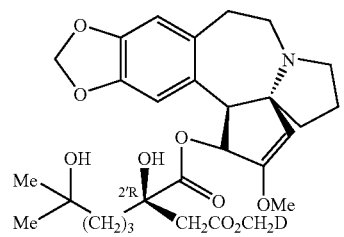

Step One

To a stirred mixture of 4'-demethyl-anhydro-homoharringtonine (100 mg, 0.19 mmol) resulting from Example 2 in dry dichloromethane (0.8 ml) was added at 0° C. triethylamine (27 µl, 0.19 mmol) and dropwise 2,4,6-trichlorobenzoyl chloride (30 µl, 0.19 mmol). After stirring at 0° C. during 10 minutes then at room temperature during 2.5 hours a solution of 4-dimethylaminopyridine (48 mg, 0.39 mmol) and methyl-d alcohol (20 µl, 0.35 mmol) in dry dichloromethane (0.8 ml) was added. After stirring at room temperature for 19 hours, the reaction mixture was evaporated to dryness. The resulting crude product was purified by column chromatography (silica 15-40 µm (13 g), dichloromethane then dichloromethane/AcOEt, 60:40 to 0:100) to provide the expected compound (56.7 mg, 56%), purity HPLC=99,7%. The (2'R)-2',4''-anhydro-(4'-²H)-homoharringtonine thus obtained showed the following characteristics:

¹H NMR 400 MHz (CDCl₃) (δ ppm, J Hz): 6.61 (1H, s, H-17), 6.57 (1H, s, H-14), 5.91 (1H, d, J=9.7, H-3), 5.86 et 5.79 (2H, 2d, $J_{AB}$=1.4, OCH₂O), 5.04 (1H, s, H-1), 3.79 (1H, d, J=9.7, H4), 3.70 (3H, s, OCH₃), 3.57 (2H, s, OCH₂D), 3.16 (1H, m, H-11β), 3.11 (1H, m, H-8α), 2.94 (1H, m, H-10α), 2.59 (2H, m, H-8β and 10β), 2.36 (1H, dd, J=14.2 and 6.9, H-11α), 2.13 et 1.66 (2H, 2d, $J_{AB}$=14.3, $CH_2CO_2$), 2.02 (1H, m, H-$6_A$), 1.99 (1H, m, H-$6_B$), 1.89 (2H, m, $CH_2$-7), 1.8-1.0 (6H, m, 3×$CH_2$), 1.11 (3H, s, $CH_3$), 1.04 (3H, s, $CH_3$).

Step Two

To a stirred solution of (2'R)-2',4''-anhydro-(4'-$^2$H)-homoharringtonine (76 mg, 0.14 mmol) in dry dichloromethane (0.4 ml) under nitrogen was added at −10° C. a commercial solution of hydrobromic acid in acetic acid (0.258 ml, 1.29 mmol, HBr 30% w/w, 9 eq.). After stirring at −10° C. for 3 hours, the reaction mixture was poured in water (3.8 ml). The mixture was stirred at −10° C. during 10 min then at room temperature for 3 hours. After this time was added a sodium carbonate solution (0.76 M) up to pH 9. The resulting aqueous layer was extracted with dichloromethane (3×15 ml) and the combined organic layers were dried over magnesium sulfate and evaporated to dryness. The crude product thus obtained was purified by phase-reversed chromatography (octadecylsilane 12 μm, buffer pH 3/acetonitrile, 90/10). The resulting aqueous layer was alkalinized to pH 9 with ammonia 25% and extracted with dichloromethane (4×100 ml). The combined organic layers were evaporated to dryness to provide the expected product (42 mg, 53%), purity HPLC=99.2%. The product thus obtained showed the following characteristics:

$^1$H NMR 400 MHz (CDCl$_3$) (δ ppm, J Hz): 6.62 (1H, s, H-17), 6.54 (1H, s, H-14), 6.00 (1H, d, J=9.8, H-3), 5.87 (2H, s, $OCH_2O$), 5.05 (1H, s, H-1), 3.78 (1H, d, J=9.8, H-4), 3.68 (3H, s, OMe), 3.56 (2H, s, O—$CH_2D$), 3.53 (1H, s, 2'-OH), 3.10 (2H, m, H-11β and 8α), 2.94 (1H, m, H-10α), 2.60 (2H, m, H-8β and 10β), 2.38 (1H, m, H-11α), 2.26 and 1.91 (2H, 2d, $J_{AB}$=16.5, $CH_2CO_2$), 2.01 (1H, m, H-$6_A$), 1.89 (1H, m, H-$6_B$), 1.76 (2H, m, $CH_2$-7), 1.7-1.1 (6H, m, 3×$CH_2$), 1.19 (6H, s, 2×$CH_3$).

EXAMPLE 77

Preparation of (2'R)-(4'-$^2$H) harringtonine, from harringtonine

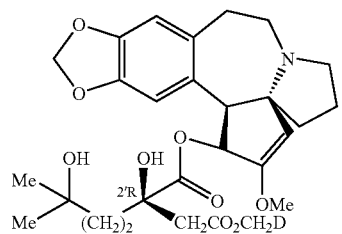

Sodium hydride 60% (2.5 mg, 0.062 mmol, 0.22 eq.) was added to a solution of harringtonine (150 mg, 0.28 mmol) in methyl-d alcohol (573 μl, 14.1 mmol) and the resulting mixture was stirred at room temperature for 1 hour. After addition water (15 ml), the aqueous layer was extracted with dichloromethane (3×15 ml). The combined organic layers were dried over magnesium sulfate and evaporated to dryness to provide 102 mg of crude product with a purity of expected product of 90% and 3.2% of harringtonine. The reaction was started again three times with this crude product to provide 92 mg. The crude product thus obtained was purified by phase-reversed chromatography (octadecylsilane 12 μm, buffer pH 3/acetonitrile, 90/10). The resulting aqueous layer was alkalinized to pH 9 with ammonia 25% and extracted with dichloromethane (4×80 ml). The combined organic layers were evaporated to dryness to provide the expected product (67 mg, 44.4%), purity HPLC=100%. The product thus obtained showed the following characteristics:

$^1$H NMR 400 MHz (CDCl$_3$) (δ ppm, J Hz): 6.62 (1H, s, H-17), 6.59 (1H, s, H-14), 6.00 (1H, d, J=9.8, H-3), 5.87 (2H, s, $OCH_2O$), 5.08 (1H, s, H-1), 3.79 (1H, d, J=9.8, H-4), 3.69 (3H, s, OMe), 3.64 (1H, s, 2'-OH), 3.57 (2H, s, O—$CH_2D$), 3.09 (2H, m, H-11β and 8β), 2.94 (1H, m, H-10α), 2.57 (2H, m, H-8β and 10β), 2.38 (1H, dd, J=14.1 and 6.8, H-11α), 2.29 and 1.90 (2H, 2d, $J_{AB}$=16.5, $CH_2CO_2$), 2.02 (1H, m, H-$6_A$), 1.91 (1H, m, H-$6_B$), 1.76 (2H, m, $CH_2$-7), 1.7-1.1 (4H, m, 2×$CH_2$), 1.17 (3H, s, $CH_3$), 1.15 (3H, s, $CH_3$).

EXAMPLE 78

Preparation of (2'R)-4'-(2-methoxyethoxy)-4'-demethyl-homoharringtonine

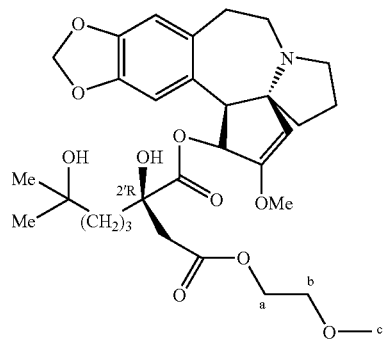

Step One

To a stirred mixture of 4'-demethyl-anhydro-homoharringtonine (200 mg, 0.389 mmol) resulting from Example 2 in dry dichloromethane (1.0 ml) was added at 0° C. triethylamine (dried over potassium hydroxide) (52 μl, 0.389 mmol) and 2,4,6-trichlorobenzoyl chloride (58 μl, 0.389 mmol) over a period of 10 minutes. After stirring at room temperature for 2.5 hours a solution of 4-dimethylaminopyridine (92 mg, 0.780 mmol) and 2-methoxyethanol (60 μl, 0.780 mmol) in dry dichloromethane (1.0 ml) was added. The reaction mixture was stirring at room temperature for 15 hours, then was purified by column chromatography (silica 15-40 μm (6 g), dichloromethane then dichloromethane/methanol, 99:1) to provide the expected compound (174 mg, 78%). The 4'-(2-methoxyethyl)-4'-demethyl-anhydro-homoharringtonine thus obtained showed the following characteristics:

$^1$H NMR 400 MHz (CDCl$_3$) (δ ppm, J Hz): 6.61 (1H, s, H-17), 6.58 (1H, s, H-14), 5.92 (1H, d, J=9.6, H-3), 5.86 and 5.81 (2H, 2d, $J_{AB}$=1.4, $OCH_2O$), 5.04 (1H, s, H-1), 4.14 (2H, m, $CO_2CH_2$), 3.79 (1H, d, J=9.7, H-4), 3.70 (3H, s, 2-OCH$_3$), 3.55 (2H, t, J=4.9, $CH_2OCH_3$), 3.36 (3H, s, OCH$_3$), 3.12 (2H, m, H-11β,8α), 2.99 (1H, m, H-10α), 2.61 (2H, m, H-8β,10β), 2.38 (1H, dd, J=14.1 et 6.8, H 11α), 2.16 et 1.67 (2H, 2d, $J_{AB}$=14.4, $CH_2CO_2$), 2.04 (1H, m, H-$6_A$), 1.91 (1H, m, H-$6_B$), 1.77 (2H, m, $CH_2$-7), 1.7-1.2 (6H, m, 3×$CH_2$), 1.19 (3H, s, $CH_3$), 1.03 (3H, s, $CH_3$).

Step Two

To a stirred solution of 4'-(2-methoxyethyl)-4'-demethyl-anhydro-homoharringtonine (144 mg, 0.250 mmol) in dry dichloromethane (0.75 ml) under nitrogen was added at −10° C. a commercial solution of hydrobromic acid in acetic acid (0.45 ml, 2.27 mmol, HBr 30% w/w, 9 eq.). After stirring at −10° C. for 2 hours, was added water (7.0 ml) and the mixture was stirred at −10° C. during 15 min then at room temperature for 2 h 45. After this time was added a sodium carbonate solution (0.76 M, 10 ml) up to pH 8. The resulting aqueous layer was extracted with dichloromethane (4×15 ml) and the combined organic layers were dried over magnesium sulfate and evaporated to dryness to provide the expected compound (138 mg crude, 93%).

The crude product thus obtained was purified by phase-reversed chromatography (Polygoprep 100-12 C18 (45 g), buffer pH 3/methanol, 70/30). After removal of methanol in vacuo the resulting aqueous layer was alkalinised to pH 9.0 with ammonia 25% and extracted with dichloromethane (5×100 ml). The combined organic layers were dried over magnesium sulfate and evaporated to dryness to provide the expected compound (43 mg, 29%). The product thus obtained showed the following characteristics:

$^1$H NMR 400 MHz (CDCl$_3$) (δ ppm, J Hz): 6.62 (1H, s, H-17*), 6.56 (1H, s, H-14*), 5.99 (1H, d, J=9.8, H-3), 5.89 and 5.85 (2H, 2d, J$_{AB}$=1.3, OCH$_2$O), 5.05 (1H, s, H-1), 4.12 (2H, m, C$\underline{H}_2$-a), 3.78 (1H, d, J=9.8, H-4), 3.68 (3H, s, OCH$_3$), 3.60 (1H, s, 2'-OH), 3.53 (2H, t, J=4.6, C$\underline{H}_2$-b), 3.37 (3H, s, CH$_3$-c), 3.09 (2H, m, H-11β+H-8α), 2.94 (1H, m, H-10α), 2.60 (2H, m, H-8β+H-10β), 2.38 (1H, dd, J$_{AB}$=14.0, J=6.7, H-11α), 2.30 and 1.93 (2H, 2d, J$_{AB}$=16.3, C$\underline{H}_2$CO$_2$), 2.02 (1H, m, H-6$_A$), 1.90 (1H, m, H-6$_B$), 1.76 (2H, m, CH$_2$-7$_{A-B}$), 1.5-1.1 (6H, m, 3×CH$_2$), 1.19 (3H, s, CH$_3$), 1.18 (3H, s, CH$_3$).

EXAMPLE 79

Preparation of (2'R)-4'-phenoxy-4'-demethylhomo-harringtonine

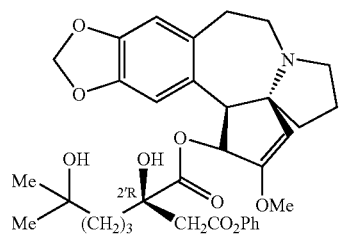

Step One

1°) Method A

To a stirred mixture of 4'-demethyl-anhydro-homoharringtonine (100 mg, 0.19 mmol) resulting from Example 2 in dry dichloromethane (0.5 ml) was added at 0° C. triethylamine (dried over potassium hydroxide) (27 µl, 0.19 mmol) and 2,4,6-trichlorobenzoyl chloride (29 µl, 0.19 mmol) over a period of 10 minutes. After stirring at room temperature for 1.0 hour a solution of 4-dimethylaminopyridine (25 mg, 0.20 mmol) and phenol (19 mg, 0.20 mmol) in dry dichloromethane (0.5 ml) was added. After stirring at room temperature for 15 hours, the reaction mixture was diluted with dichloromethane (5 ml). The resulting organic layer was successively washed with water (7 ml), with saturated sodium hydrogen carbonate solution (7 ml), with brine (5 ml). After a last extraction of the combined aqueous layers with dichloromethane (10 ml) the combined organic layers were dried over magnesium sulfate and evaporated to dryness. The resulting crude product was purified by column chromatography (silica 15-40 µm (6 g), dichloromethane then dichloromethane/methanol, 99:1 to 97:3) to provide the expected compound (46 mg, 40%). The 4' phenoxy-4'-demethyl-anhydro-homoharringtonine thus obtained showed the following characteristics:

$^1$H NMR 400 MHz (CDCl$_3$) (δ ppm, J Hz): 7.31 (2H, t, J=7.9, m-PhO), 7.21 (1H, t, J=7.5, p-PhO), 7.05 (2H, d, J=7.6, o-PhO), 6.69 (1H, s, H-17), 6.60 (1H, s, H-14), 5.86 (3H, m, OCH$_2$O, H-3), 5.02 (1H, s, H-1), 3.81 (1H, d, J=9.6, H-4), 3.66 (3H, s, OCH$_3$), 3.33 and 3.15 (3H, m, H-11β, 10β, 8α), 2.67 (2H, m, H-10β, 8β), 2.48 (1H, dd, J=14.0 et 6.2, H 11α), 2.30 et 1.96 (2H, 2d, J$_{AB}$=13.9, C$\underline{H}_2$CO$_2$), 2.05 (1H, m, H-6$_A$), 1.96 (1H, m, H-6$_B$), 1.90 to 1.10 (8H, m, CH$_2$-7, 3×CH$_2$), 1.17 (3H, s, CH$_3$), 1.06 (3H, s, CH$_3$).

1°) Method B

To a stirred mixture of 4'-demethyl-anhydro-homoharringtonine (100 mg, 0.19 mmol) resulting from Example 2 in dry dichloromethane (0.5 ml) was added at room temperature the phenol (37 mg, 0.38 mmol). A solution of dicylohexylcarbodiimide (157 mg, 0.76 mmol) in dry dichloromethane (0.5 ml) was added at the above mixture. After stirring at room temperature for 15 hours, the reaction mixture was purified by column chromatography (silica 15-40 µm (6 g), dichloromethane then dichloromethane/methanol, 99:1 to 97:3) to provide the expected compound (54 mg, 47%). The product thus obtained showed identical characteristics to this obtained with method A.

Step Two

To a stirred solution of 4'-phenoxy-4'-demethyl-anhydro-homoharringtonine (50 mg, 0.085 mmol) in dry dichloromethane (0.4 ml) under nitrogen was added at −10° C. a commercial solution of hydrobromic acid in acetic acid (0.152 ml, 0.76 mmol, HBr 30% w/w, 9 eq.). After stirring at −10° C. for 3 hours, the reaction mixture was poured in water (3 ml). The mixture was stirred at −10° C. during 10 min then at room temperature for 3 hours. After this time was added a sodium carbonate solution (0.76 M) up to pH 9. The resulting aqueous layer was extracted with dichloromethane (3×15 ml) and the combined organic layers were dried over magnesium sulfate and evaporated to dryness. The crude product thus obtained was purified by phase-reversed chromatography (octadecylsilane 12 µm, buffer pH 3/acetonitrile, 90:10). The resulting aqueous layer was alkalinized to pH 9 with ammonia 25% and extracted with dichloromethane (4×100 ml). The combined organic layers were evaporated to dryness to provide the expected product (23 mg, 45%). The product thus obtained showed the following characteristics:

$^1$H NMR 400 MHz (CDCl$_3$) (δ ppm, J Hz): 7.31 (2H, t, J=7.9, m-PhO), 7.21 (1H, t, J=7.5, p-PhO), 7.05 (2H, d, J=7.6, o-PhO), 6.62 (1H, s, H-17), 6.54 (1H, s, H-14), 6.00 (1H, d, J=9.8, H-3), 5.87 (2H, s, OCH$_2$O), 5.05 (1H, s, H-1), 3.78 (1H, d, J=9.8, H-4), 3.68 (3H, s, OMe), 3.53 (1H, s, 2'-OH), 3.10 (2H, m, H-11β and 8α), 2.94 (1H, m, H-10α), 2.60 (2H, m, H-8β and 10β), 2.38 (1H, m, H-11α), 2.40 et 2.15 (2H, 2d, J$_{AB}$=16.5, CH$_2$CO$_2$), 2.01 (1H, m, H-6$_A$), 1.89 (1H, m, H-6$_B$), 1.76 (2H, m, CH$_2$-7), 1.7-1.1 (6H, m, 3×CH$_2$), 1.19 (6H, s, 2×CH$_3$).

EXAMPLE 80

Preparation of (2'R)-4'-(2-benzyloxyethoxy)-4'-demethyl-homoharringtonine

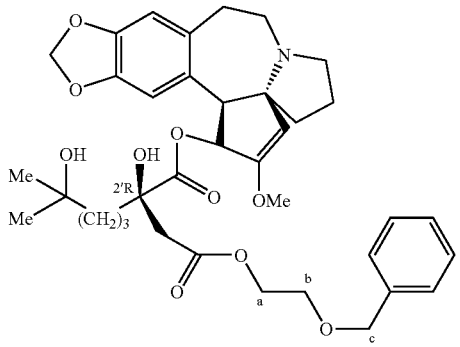

Sodium hydride 60% (3.2 mg, 0.081 mmol) was added to a solution of homoharringtonine (150 mg, 0.270 mmol) in 2-benzyloxyethanol (2 ml, 13.74 mmol) at room temperature and the resulting mixture was stirred at 25° C. for 23 h. under nitrogen. After adjusting to pH 7 by addition of hydrochloric acid 1 N (100 µl), the mixture reaction was purified by column chromatography (silica 15-40 µm, (22 g)), dichloromethane then dichloromethane/MeOH 93:7 to 80:20 to provide the compound which was again purified by phase-reversed chromatography (Polygoprep 100-12 C18 (45 g), buffer pH 3/methanol, 65:35). After removal of methanol in vacuo the resulting aqueous layer was alkalinized to pH 9.0 with ammonia 25% and extracted with dichloromethane (5×50 ml). The combined organic layers were dried over magnesium sulfate and evaporated to dryness to provide the expected compound (100 mg, 55%). The product thus obtained showed the following characteristics:

$^1$H NMR 400 MHz (CDCl$_3$) (δ ppm, J Hz): 7.36 (5H, m, Ph), 6.60 (1H, s, H-14*), 6.53 (1H, s, H-17*), 5.95 (1H, d, J=9.8, H-3), 5.82 and 5.79 (2H, 2d, J=1.2, OCH$_2$O), 5.03 (1H, s, H-1), 4.57 and 4.53 (2H, 2d, J=11.9, CH$_2$-c), 4.15 (2H, m, CH$_2$-a), 3.68 (1H, d, H-4), 3.67 (3H, s, OCH$_3$), 3.62 (1H, t, J=4.8, CH$_2$-b), 3.56 (1H, s, 2'-OH), 3.08 (2H, m, H-11β+H-8α), 2.93 (1H, m, H-10α), 2.58 (2H, m, H-8β+H-10β), 2.36 (1H, dd, J=14.0 and 6.8, H-11α), 2.28 and 1.91 (2H, 2d, J=16.3, CH$_2$CO$_2$), 1.96 (1H, m, H-6$_A$), 1.85 (1H, m, H-6$_B$), 1.74 (2H, m, CH$_2$-7), 1.50-1.10 (6H, m, 3×CH$_2$), 1.19 (3H, s, CH$_3$), 1.18 (3H, s, CH$_3$).

EXAMPLE 81

Preparation of (2'R)-4'-(1-naphtalenemethoxy)-4'-demethyl-homoharringtonine

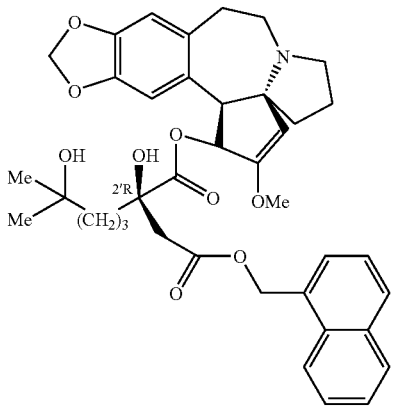

Sodium hydride 60% (3.2 mg, 0.081 mmol) was added to a solution of homoharringtonine (150 mg, 0.270 mmol) in 1-naphtalenemethanol (2.17 g, 13.74 mmol) at 70° C. and the resulting mixture was stirred at 70° C. during 1 h. under nitrogen. After adjusting to pH 7 by addition of hydrochloric acid 1 N (100 µl), the mixture reaction was purified by column chromatography (silica 15-40 µm, (22 g)), dichloromethane then dichloromethane/MeOH 98:2 to 95:5 to provide the compound which was again purified by phase-reversed chromatography (Polygoprep 100-12 C18 (45 g), buffer pH 3/methanol, 50:50). After removal of methanol in vacuo the resulting aqueous layer was alkalinized to pH 9.0 with ammonia 25% and extracted with dichloromethane (5×15 ml). The combined organic layers were dried over magnesium sulfate and evaporated to dryness to provide the expected compound (62 mg, 34%). The product thus obtained showed the following characteristics:

$^1$H NMR 400 MHz (CDCl$_3$) (δ ppm, J Hz): 7.95 (1H, d, J=8.3, H-naph), 7.88 (1H, d, J=7.8, H-naph), 7.85 (1H, d, J=8.2, H-naph), 7.58 (1H, dt, 2×J=7.5, J=1.4, H-naph), 7.53 (2H, m, 2×H-naph), 7.46 (1H, t, J=7.5, H-naph), 6.60 (1H, s, H-17*), 6.35 (1H, s, H-14*), 5.93 (1H, d, J=9.7, H-3), 5.72 and 5.60 (2H, 2d, J$_{AB}$=1.1, OCH$_2$O), 5.59 and 5.39 (2H, 2d, J$_{AB}$=12.6, CO$_2$CH$_2$), 5.04 (1H, s, H-1), 3.67 (3H, s, OCH$_3$), 3.63 (1H, d, J=9.8, H-4), 3.52 (1H, s, 2'-OH), 3.08 (2H, m, H-11β+H-8α), 2.93 (1H, m, H-10α), 2.58 (2H, m, H-8β+H-10β), 2.35 (1H, dd, J=14.0 and 6.7, H-11α), 2.30 and 1.90 (2H, 2d, J=16.3, CH$_2$CO$_2$), 1.98 and 1.89 (2H, 2m, H-6$_{A-B}$), 1.75 (2H, m, CH$_2$-7), 1.50-1.10 (6H, m, 3×CH$_2$).

EXAMPLE 82

Preparation of (2'R)-4'-(2-thiophenemethoxy)-4'-demethyl-homoharringtonine

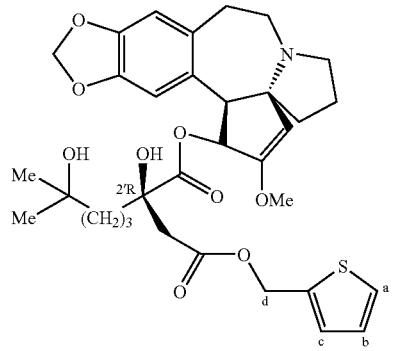

Sodium hydride 60% (6.4 mg, 0.162 mmol) was added to a solution of homoharringtonine (150 mg, 0.270 mmol) in 2-thiophenemethanol (1.3 ml, 13.74 mmol) at room temperature and the resulting mixture was stirred at 25° C. for 5 h. under nitrogen. After adjusting to pH 7 by addition of hydrochloric acid 1 N (100 µl), the mixture reaction was purified by column chromatography (silica 15-40 µm, (13 g)), dichloromethane then dichloromethane/MeOH 80:20 to provide the compound which was again purified by phase-reversed chromatography (Polygoprep 100-12 C18 (131 g), buffer pH 3/methanol, 70:30). After removal of methanol in vacuo the resulting aqueous layer was alkalinized to pH 9.0 with ammonia 25% and extracted with dichloromethane (5×25 ml). The combined organic layers were dried over magnesium sulfate and evaporated to dryness to provide the expected compound (85 mg, 49%). The product thus obtained showed the following characteristics:

$^1$H NMR 400 MHz (CDCl$_3$) (δ ppm, J Hz): 7.32 (1H, dd, Ja-b=5.1, Ja-c=1.0, H-a), 7.07 (1H, d, Jc-b=3.4, H-c), 6.98 (1H,dd, Jb-a=5.0, Jb-c=3.5, H-b), 6.62 (1H, s, H-17*), 6.48 (1H, s, H-14*), 5.98 (1H , d, J=9.7, H-3), 5.82 and 5.76 (2H, 2d, J$_{AB}$=1.3, OCH$_2$O), 5.24 and 5.07 (2H, 2d, J$_{AB}$=13.8, CH$_2$-d), 5.05 (1H, s, H-1), 3.75 (1H, d, J=9.8, H-4), 3.68 (3H, s, OCH$_3$), 3.50 (1H, s, 2'-OH), 3.09 (2H, m, H-11β+H-8α), 2.94 (1H, dt, J=11.1 and 6.9, H-10α), 2.59 (2H, m, H-8β+H-10β), 2.37 (1H, dd, J=) 14.0 and 6.7, H-11α), 2.28 and 1.89 (2H, 2d, J$_{AB}$=16.3, CH$_2$CO$_2$), 2.02 and 1.90 (2H, 2m, H-6$_{A,B}$), 1.76 (2H, m, CH$_2$-7$_{A,B}$), 1.50-1.10 (6H, m, 3×CH$_2$), 1.18 (6H, 2s, 2×CH$_3$).

EXAMPLE 83

Preparation of (2'R)-4'-furfuryl-4'-demethyl-homo-harringtonine

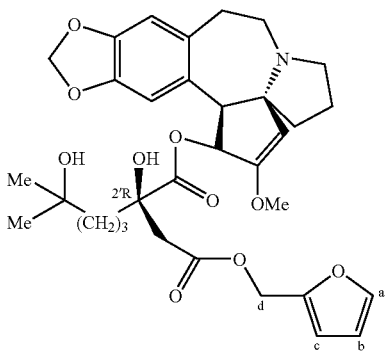

Sodium hydride 60% (16 mg, 0.400 mmol) was added to a solution of homoharringtonine (150 mg, 0.270 mmol) in furfuryl alcohol (1.2 ml, 13.74 mmol) at room temperature and the resulting mixture was stirred at 25° C. for 24 h. under nitrogen. After adjusting to pH 7 by addition of hydrochloric acid 1 N (324 μl), the mixture reaction was purified by column chromatography (silica 15-40 μm, (12 g)), dichloromethane then dichloromethane/MeOH 98:2 to 80:20 to provide the compound which was again purified by phase-reversed chromatography (Polygoprep 100-12 C18 (45 g), buffer pH 3/methanol, 65:35). After removal of methanol in vacuo the resulting aqueous layer was alkalinized to pH 9.0 with ammonia 25% and extracted with dichloromethane (5×50 ml). The combined organic layers were dried over magnesium sulfate and evaporated to dryness to provide the expected compound (47 mg, 28%). The product thus obtained showed the following characteristics:

$^1$H NMR 400 MHz (CDCl$_3$) (δ ppm, J Hz): 7.43 (1H, d, H-a), 6.62 (1H, s, H-14), 6.52 (1H, s, H-17), 6.39 (1H, d, J=3.1, H-c), 6.36 (1H, dd, J=4.9 and 1.8, H-b), 5.95 (1H, d, J=9.8, H-3), 5.84 and 5.83 (2H, 2s, OCH$_2$O), 5.05 (1H, s, H-1), 5.04 and 4.87 (2H, 2d, J=13.1, CH$_2$-d), 3.75 (1H, d, J=9.8, H-4), 3.67 (3H, s, OCH$_3$), 3.50 (1H, s, 2'-OH), 3.09 (2H, m, H-11β+H-8α), 2.94 (1H, dt, J=11.0 and 6.9, H-10α), 2.59 (2H, m, H-8β+H-10β), 2.37 (1H, dd, J=13.9 and 6.7, H-11α), 2.27 and 1.86 (2H, 2d, J$_{AB}$=16.4, CH$_2$CO$_2$), 2.02 and 1.90 (2H, m, H-6$_{A,B}$), 1.76 (2H, m, CH$_2$-7$_{A,B}$), 1.50-1.10 (6H, m, 3×CH$_2$), 1.18 (6H, 2s, 2×CH$_3$).

EXAMPLE 84

Preparation of (2' R)-4'-hexanyloxy-4'-demethyldeoxyharringtonine

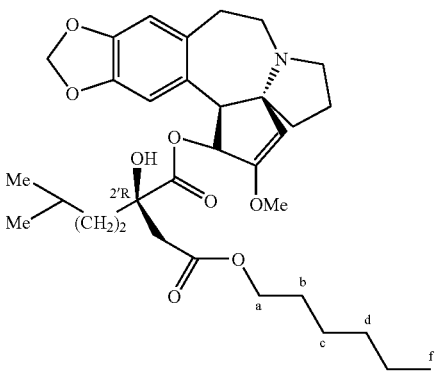

Sodium hydride 60% (3.7 mg, 0.093 mmol) was added to a solution of deoxyharringtonine (120 mg, 0.232 mmol) in 1-hexanol (1.7 ml, 13.8 mmol) at room temperature and the resulting mixture was stirred at 25° C. for 2 h. under nitrogen. After adjusting to pH 1 by addition of hydrochloric acid 0.1N (950 μl), the aqueous layer was washed with ether (5×15 ml). The combined organic layers were extracted by hydrochloric acid 0.1N (2×10 ml). The combined acid aqueous layers were alkalinized with ammonia 25% (pH=8.0) and were extracted with dichloromethane (5×20 ml). The combined organic layers were dried over magnesium sulfate and evaporated to dryness. The crude product thus obtained was purified by phase-reversed chromatography (Polygoprep 100-12 C18 (125 g), buffer pH 3/methanol, 30:70). After removal of methanol in vacuo the resulting aqueous layer was alkalinized to pH 9.0 with ammonia 25% and extracted with dichloromethane (5×25 ml). The combined organic layers were dried over magnesium sulfate and evaporated to dryness to provide the expected compound (30 mg, 22%). The product thus obtained showed the following characteristics:

$^1$H NMR 400 MHz (CDCl$_3$) (δ ppm, J Hz): 6.62 (1H, s, H-17*), 6.53 (1H, s, H-14*), 5.97 (1H, d, J=9.8, H-3), 5.86 and 5.84 (2H, 2d, J$_{AB}$=1.3, OCH$_2$O), 5.04 (1H, s, H-1), 4.00 and 3.90 (2H, 2dt, J=10.7 and 6.9, CH$_2$-a), 3.77 (1H, d, J=9.8, H-4), 3.68 (3H, s, OCH$_3$), 3.48 (1H, s, 2'-OH), 3.12 (2H, m, H-11β+H-8α), 2.95 (1H, H-10α), 2.60 (2H, m, H-8β+H-10β), 2.38 (1H, dd, J=14.0 and 6.8, H-11α), 2.24 and 1.88 (2H, 2d, J$_{AB}$=16.3, CH$_2$CO$_2$), 2.03 and 1.91 (2H, 2m, H-6$_{A,B}$), 1.76 (2H, m, CH$_2$-7$_{A,B}$), 1.56 (2H, m, CH$_2$-b), 1.41 (3H, m, CH+CH$_2$), 1.29 (7H, m, CH+CH$_2$-c,d,e), 0.98 (1H, m, 1H), 0.89 (3H, t, J=6.8, CH$_3$-f), 0.84 and 0.83 (6H, 2d, J=6.5, 2×CH$_3$).

EXAMPLE 85

Preparation of (2'R)-4'-p-nitrobenzyloxy-4'-demethyl-homoharringtonine

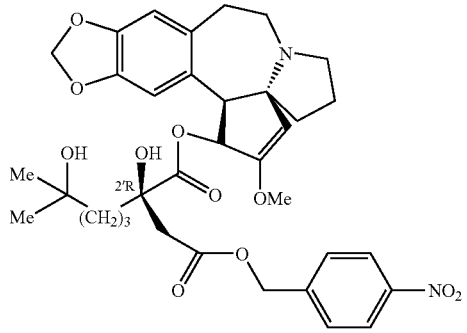

Sodium hydride 60% (3.7 mg, 0.092 mmol) was added to a solution of homoharringtonine (140 mg, 0.256 mmol), p-nitrobenzyl alcohol (780 mg, 5.09 mmol) in dichloromethane (1.0 ml) and diethyl ether (200 μl) at room temperature and the resulting mixture was stirred at 25° C. for 45 min. under nitrogen. After adjusting to pH 1.4 by addition of hydrochloric acid 0.1N (350 μl), the aqueous layer was washed with ether (3×20 ml). The combined organic layers were extracted by hydrochloric acid 0.1N (2×10 ml). The combined acid aqueous layers were alkalinized with ammonia 25% (pH=8.4) and were extracted with dichloromethane (5×20 ml). The combined organic layers were dried over magnesium sulfate and evaporated to dryness. The crude product thus obtained was purified by phase-reversed chromatography (Polygoprep 100-12 C18 μm (125 g), buffer pH 3/methanol, 47:53). After removal of methanol in vacuo the resulting aqueous layer was alkalinized to pH 9.0 with ammonia 25% and extracted with dichloromethane (4×100 ml). The combined organic layers were dried over magnesium sulfate and evaporated to dryness to provide the expected compound (100 mg, 58.6%). The product thus obtained showed the following characteristics:

$^1$H NMR 400 MHz (CDCl$_3$) (δ ppm, J Hz): 8.20 and 7.50 (2H, 2d, J=8.5, o,m-PhNO$_2$), 6.62 and 6.45 (2H, 2s, H14, H17), 5.96 (1H, d, J=9.8, H-3), 5.79 and 5.70 (2H, 2s, OCH$_2$O), 5.05 (1H, s, H-1), 5.10 and 5.00 (2H, 2d, J=12.1, OCH$_2$Ph), 3.70 (1H, d, H-4), 3.68 (3H, s, OCH$_3$), 3.51 (1H, s, 2'-OH), 3.09 (2H, m, H-11β+H-8α), 2.93 (1H, m, H-10α), 2.59 (2H, m, H-8β and H-10β), 2.38 (1H, dd, H-11α), 2.27 and 1.89 (2H, 2d, J$_{AB}$=16.2, CH$_2$CO$_2$), 2.01 and 1.89 (2H, 2m, H-6$_{A,B}$), 1.75 (2H, m, CH$_2$-7), 1.80-1.10 (6H, m, 3×CH$_2$), 1.25 (1H, s, 4"-OH), 1.18 (6H, s, 2×CH$_3$).

EXAMPLE 86

Preparation of (2'R)-4'-p-methoxybenzyloxy-4'-demethyl-homoharringtonine

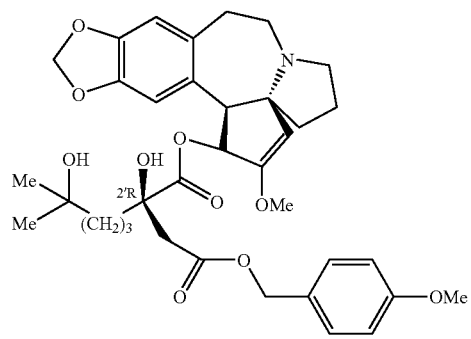

Sodium hydride 60% (3.5 mg, 0.087 mmol) was added to a solution of homoharringtonine (140 mg, 0.256 mmol) in p-methoxybenzyl alcohol (1.0 g, 7.24 mmol) at room temperature and the resulting mixture was stirred at 25° C. for 45 min. under nitrogen. After adjusting to pH 1.4 by addition of hydrochloric acid 0.1N (350 μl), the aqueous layer was washed with ether (3×20 ml). The combined organic layers were extracted by hydrochloric acid 0.1N (2×10 ml). The combined acid aqueous layers were alkalinized with ammonia 25% (pH=8.4) and were extracted with dichloromethane (5×20 ml). The combined organic layers were dried over magnesium sulfate and evaporated to dryness. The crude product thus obtained was purified by column chromatography (silica 15-40 μm (13 g)), dichloromethane then dichloromethane/MeOH 99:1 to 97:3 to provide the expected compound (90 mg, 54%). The product thus obtained showed the following characteristics:

$^1$H NMR 400 MHz (CDCl$_3$) (δ ppm, J Hz): 7.27 and 6.89 (2H, 2d, J=8.7, o,m-PhOMe), 6.62 and 6.45 (2H, 2s, H14, H17), 5.96 (1H, d, J=9.8, H-3), 5.79 and 5.70 (2H, 2s, OCH$_2$O), 5.05 (1H, s, H-1), 5.03 and 4.87 (2H, 2d, J=12.1, OCH$_2$Ph), 3.81 (3H, s, p-MeO-Ph), 3.70 (1H, d, H-4), 3.68 (3H, s, OCH$_3$), 3.51 (1H, s, 2'-OH), 3.09 (2H, m, H-11β+H-8α), 2.93 (1H, m, H-10α), 2.59 (2H, m, H-8β and H-10β), 2.38 (1H, dd, H-11α), 2.27 and 1.89 (2H, 2d, J$_{AB}$=16.2, CH$_2$CO$_2$), 2.01 and 1.89 (2H, 2m, H-6$_{A,B}$), 1.75 (2H, m, CH$_2$-7), 1.80-1.10 (6H, m, 3×CH$_2$), 1.25 (1H, s, 4"-OH), 1.18 (6H, 2s, 2×CH$_3$).

EXAMPLE 87

Preparation of (2'R)-(4'-$^2$H$_2$)homoharringtonine

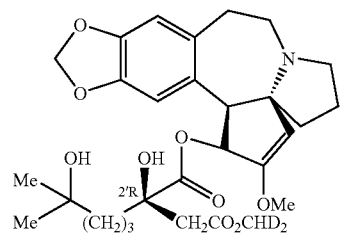

Step One

To a stirred mixture of 4'-demethyl-anhydro-homoharringtonine (100 mg, 0.19 mmol) resulting from Example 2 in dry dichloromethane (0.8 ml) was added at 0° C. triethylamine (27 μl, 0.19 mmol) and dropwise 2,4,6-trichlorobenzoyl chloride (30 μl, 0.19 mmol). After stirring at 0° C. during 10 minutes then at room temperature during 2.5 hours a solution of 4-dimethylaminopyridine (48 mg, 0.39 mmol) and methyl-d$_2$ alcohol (14.5 μl, 0.35 mmol) in dry dichloromethane (0.8 ml) was added. After stirring at room temperature for 19 hours, the reaction mixture was evaporated to dryness. The resulting crude product was purified by column chromatography (silica 15-40 μm (13 g), dichloromethane then dichloromethane/AcOEt, 60:40 to 0:100) to provide the expected compound (51.7 mg, 50%). The (2'R)-2',4"-anhydro-(4'-$^2$H$_2$)-homoharringtonine thus obtained showed the following characteristics:

$^1$H NMR 400 MHz (CDCl$_3$) (δ ppm, J Hz): 6.61 (1H, s, H-17), 6.57 (1H, s, H-14), 5.91 (1H, d, J=9.7, H-3), 5.86 et 5.79 (2H, 2d, J$_{AB}$=1.4, OCH$_2$O), 5.04 (1H, s, H-1), 3.79 (1H, d, J=9.7, H4), 3.70 (3H, s, OCH$_3$), 3.57 (1H, s, OCHD$_2$), 3.16 (1H, m, H-11β), 3.11 (1H, m, H-8α), 2.94 (1H, m, H-10α), 2.59 (2H, m, H-8β and 10β), 2.36 (1H, dd, J=14.2 and 6.9, H-11α), 2.13 et 1.66 (2H, 2d, J$_{AB}$=14.3, CH$_2$CO$_2$), 2.02 (1H, m, H-6$_A$), 1.99 (1H, m, H-6$_B$), 1.89 (2H, m, CH$_2$-7), 1.8-1.0 (6H, m, 3×CH$_2$), 1.11 (3H, s, CH$_3$), 1.04 (3H, s, CH$_3$).

Step Two

To a stirred solution of (2'R)-2',4"-anhydro-(4'-$^2$H$_2$)-homoharringtonine (50 mg, 0.09 mmol) in dry dichloromethane (0.4 ml) under nitrogen was added at −10° C. a commercial solution of hydrobromic acid in acetic acid (0.164 ml, 0.82 mmol, HBr 30% w/w, 9 éq.). After stirring at −10° C. for 3 hours, the reaction mixture was poured in water (3 ml). The mixture was stirred at −10° C. during 10 min then at room temperature for 3 hours. After this time was added a sodium carbonate solution (0.76 M) up to pH 9. The resulting aqueous layer was extracted with dichloromethane (3×15 ml) and the combined organic layers were dried over magnesium sulfate and evaporated to dryness. The crude product thus obtained was purified by phase-reversed chromatography (octadecylsilane 12 μm, buffer pH 3/acetonitrile, 90:10). The resulting aqueous layer was alkalinized to pH 9 with ammonia 25% and extracted with dichloromethane (4×100 ml). The combined organic layers were evaporated to dryness to provide the expected product (26 mg, 50%). The product thus obtained showed the following characteristics:

$^1$H NMR 400 MHz (CDCl$_3$) (δ ppm, J Hz): 6.62 (1H, s, H-17), 6.54 (1H, s, H-14), 6.00 (1H, d, J=9.8, H-3), 5.87 (2H, s, OCH$_2$O), 5.05 (1H, s, H-1), 3.78 (1H, d, J=9.8, H-4), 3.68 (3H, s, OMe), 3.56 (1H, s, O—CHD$_2$), 3.53 (1H, s, 2'-OH), 3.10 (2H, m, H-11β and 8α), 2.94 (1H, m, H-10α), 2.60 (2H, m, H-8β and 10β), 2.38 (1H, m, H-11α), 2.26 and 1.91 (2H, 2d, J$_{AB}$=16.5, CH$_2$CO$_2$), 2.01 (1H, m, H-6$_A$), 1.89 (1H, m, H-6$_B$), 1.76 (2H, m, CH$_2$-7), 1.7-1.1 (6H, m, 3×CH$_2$), 1.19 (6H, s, 2×CH$_3$).

EXAMPLE 88

Preparation of (2'R)-(4'-$^2$H$_2$) harringtonine, from harringtonine

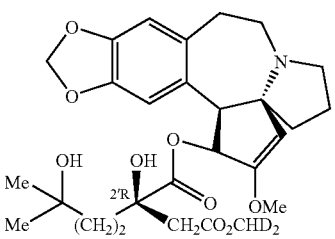

Sodium hydride 60% (2.5 mg, 0.062 mmol, 0.22 eq.) was added to a solution of harringtonine (150 mg, 0.28 mmol) in methyl-d2 alcohol (573 μl, 14.1 mmol) and the resulting mixture was stirred at room temperature for 1 hour. After addition water (15 ml), the aqueous layer was extracted with dichloromethane (3×15 ml). The combined organic layers were dried over magnesium sulfate and evaporated to dryness to provide 100 mg of crude product with a purity of expected product of 92% and 4% of harringtonine. The reaction was started again three times with this crude product to provide 90 mg. The crude product thus obtained was purified by phase-reversed chromatography (octadecylsilane 12 μm, buffer pH 3/acetonitrile, 90:10). The resulting aqueous layer was alkalinized to pH 9 with ammonia 25% and extracted with dichloromethane (4×80 ml). The combined organic layers were evaporated to dryness to provide the expected product (60 mg, 40%). The product thus obtained showed the following characteristics:

$^1$H NMR 400 MHz (CDCl$_3$) (δ ppm, J Hz): 6.62 (1H, s, H-17), 6.59 (1H, s, H-14), 6.00 (1H, d, J=9.8, H-3), 5.87 (2H, s, OCH$_2$O), 5.08 (1H, s, H-1), 3.79 (1H, d, J=9.8, H-4), 3.69 (3H, s, OMe), 3.64 (1H, s, 2'-OH), 3.57 (1H, s, O—CHD$_2$), 3.09 (2H, m, H-11β and 8α), 2.94 (1H, m, H-10α), 2.57 (2H, m, H-8β and 10β), 2.38 (1H, dd, J=14.1 and 6.8, H-11α), 2.29 and 1.90 (2H, 2d, J$_{AB}$=16.5, CH$_2$CO$_2$), 2.02 (1H, m, H-6$_A$), 1.91 (1H, m, H-6$_B$), 1.76 (2H, m, CH$_2$-7), 1.7-1.1 (4H, m, 2×CH$_2$), 1.17 (3H, s, CH$_3$), 1.15 (3H, s, CH$_3$).

EXAMPLE 89

Preparation of (2'R)-(4'-$^2$H$_3$) harringtonine, from harringtonine

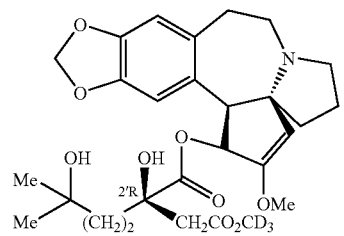

Sodium hydride 60% (2.5 mg, 0.062 mmol, 0.22 eq.) was added to a solution of harringtonine (150 mg, 0.28 mmol) in methyl-d3 alcohol (570 μl, 14.1 mmol) and the resulting mixture was stirred at room temperature for 1 hour. After addition water (15 ml), the aqueous layer was extracted with dichloromethane (3×15 ml). The combined organic layers were dried over magnesium sulfate and evaporated to dryness to provide 100 mg of crude product with a purity of expected product of 92% and 4% of harringtonine. The reaction was started again three times with this crude product to provide 90 mg. The crude product thus obtained was purified by phase-reversed chromatography (octadecylsilane 12 μm, buffer pH 3/acetonitrile, 90:10). The resulting aqueous layer was alkalinized to pH 9 with ammonia 25% and extracted with dichloromethane (4×80 ml). The combined organic layers were evaporated to dryness to provide the expected product (63 mg, 42%). The product thus obtained showed the following characteristics:

$^1$H NMR 400 MHz (CDCl$_3$) (δ ppm, J Hz): 6.62 (1H, s, H-17), 6.59 (1H, s, H-14), 6.00 (1H, d, J=9.8, H-3), 5.87 (2H, s, OCH$_2$O), 5.08 (1H, s, H-1), 3.79 (1H, d, J=9.8, H-4), 3.69 (3H, s, OMe), 3.64 (1H, s, 2'-OH), 3.09 (2H, m, H-11β and 8α), 2.94 (1H, m, H-10α), 2.57 (2H, m, H-8β and 10β), 2.38 (1H, dd, J=14.1 and 6.8, H-11α), 2.29 and 1.90 (2H, 2d, J$_{AB}$=16.5, CH$_2$CO$_2$), 2.02 (1H, m, H-6$_A$), 1.91 (1H, m, H-6$_B$), 1.76 (2H, m, CH$_2$-7), 1.7-1.1 (4H, m, 2×CH$_2$), 1.17 (3H, s, CH$_3$), 1.15 (3H, s, CH$_3$).

EXAMPLE 90

Preparation of (2'R)-4'-o-methoxybenzyloxy-4'-demethyl-homoharringtonine

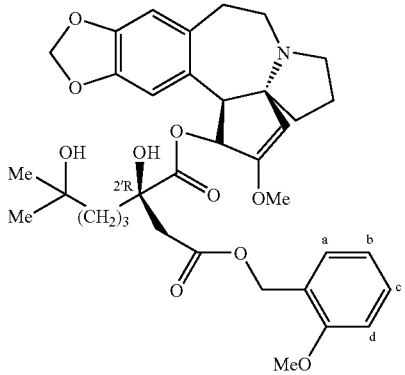

Sodium hydride 60% (29.7 mg, 0.747 mmol) was added by portion of 3.3 mg all 15 minutes to a solution of homoharringtonine (150 mg, 0.275 mmol) in o-methoxybenzyl alcohol (1.8 ml, 13.75 mmol) at room temperature and the resulting mixture was stirred at 25° C. for 1 hour under nitrogen. After adjusting to pH 7 by addition of hydrochloric acid 1 N (100 µl), the mixture reaction was purified by column chromatography (silica 15-40 µm, (12 g)), dichloromethane then dichloromethane/MeOH 99:1 to 90:10 to provide the expected compound (147 mg, 82%). The product thus obtained showed the following characteristics:

$^1$H NMR 400 MHz (CDCl$_3$) (δ ppm, J Hz): 7.30 (2H, m, H-a,c), 6.95 (1H, t, J=7.4, H-b), 6.88 (1H, d, J=6.88, H-d), 6.62 and 6.51 (2H, 2s, H14 and H17), 5.95 (1H, d, J=9.6, H-3), 5.82 and 5.73 (2H, 2s, OCH$_2$O), 5.15 and 4.99 (2H, 2d, J$_{AB}$=12.6, OCH$_2$Ph), 5.02 (1H, s, H1), 3.84 (3H, s, PhOCH$_3$), 3.69 (3H, s, OCH$_3$), 3.61 (1H, s, 2'-OH), 3.11 (2H, m, H-11β+H-8α), 2.96 (1H, m, H-10α), 2.60 (2H, m, H-8β and H-10β), 2.40 (1H, m, H-11α), 2.30 and 1.96 (2H, 2d, CH$_2$CO$_2$), 1.96 (2H, m, H-6$_{A,B}$), 1.78 (2H, 2m, H-7$_{A,B}$), 1.70-1.10 (6H, m, 3×CH$_2$), 1.27 (1H, s, 4"-OH), 1.18 (6H, 2s, 2×CH$_3$).

Biological Data

1—Materials and Methods

Structural analogues of harringtonines described in this invention were tested on K562 cell line, derived from chronic myeloid leukemia cells in blastic transformation (bcr-abl positive). The cell line was purchased from ATCC (American Tissue Culture Collection) and grown in RPMI medium supplemented with 10% heat-inactivated fetal calf serum, 2 mmol/L glutamine, 50 IU/mol penicillin and 50 IU/mol streptomycin. All tested products were initially dissolved in 2N HCl (pH=2), supplemented with ultrasound treatment during 1 h. Working concentrations were made by dilution in culture medium (pH around 7). Cells in exponential growth phase were placed into 96-microwell plates in concentration 3×10$^4$/mL (total volume 200 µL/well) and incubated with drugs for 72 h at 37° C. in 5% CO$_2$ humidified atmosphere. Following incubation, 2 µL of MTT solution (Sigma, St. Louis, Mo.) was added to each well. During the following 6 h of incubation at 37° C., the purple formazan product was formed by conversion of the yellow MTT salt in the mitochondria of the viable cells. The resulting precipitate was dissolved in DMSO and the amount of converted MTT was quantified in an ELISA reader (MR 5000, Dynatech). Each product was tested in triplicate (3×8 wells). Every test contained at least one plate with HHT as control, added in the same concentration as the tested products.

2—Results

The following table represents the results of some examples of the compounds according to the present invention in K562 cell line compared to the homoharringtonine, the harringtonine and the cephalotaxine.

TABLE 1

IC$_{50}$ Results for Structural Analogues of Harringtonines Tested on K562 Cell Line

| NAME | EXAMPLE. # | IC$_{50}$ |
|---|---|---|
| O-HEXADIENYL-DMHO[1] | 43 | 3.5 |
| O-HEXYL-DMHO | 54 | 5 |
| O-METALLYL-DMHO | 41 | 8.5 |
| O-HEXENYL-DMHO | 53 | 8.5 |

TABLE 1-continued

IC$_{50}$ Results for Structural Analogues of Harringtonines Tested on K562 Cell Line

| NAME | EXAMPLE. # | IC$_{50}$ |
|---|---|---|
| O-HEXADIENYL-DMHD | 57 | 9 |
| O-BUTYNYL-DMHO | 42 | 10.5 |
| O-CROTYL-DMHO | 37 | 12.5 |
| O-BUTYL-DMHO | 50 | 13 |
| O-CROTYL-DMHD[2] | 56 | 13.5 |
| FLUORODESOXYHARRINGTONINE | 59 | 13.5 |
| O-CROTYL-DMHA[3] | 55 | 14 |
| HOMOHARRINGTONINE | | 14 |
| O-ALLYL-DMHO | 40 | 14.5 |
| DESHYDRO-HHT | 61 | 17.5 |
| THIOTERBUTYL-DMHO | 36 | 20 |
| O-PROPYL-DMHO | 51 | 22.5 |
| O-ISOBUTYL-DMHO | 52 | 24 |
| O-SENECYL-DMHO | 39 | 28 |
| HARRINGTONINE (HHT)[4] | | 30 |
| O-ETHYL-DMHO | 25 | 41 |
| THIOISOPROPYL-DMHO | 34 | 50 |
| THIOMETHYL-DMHO | 30 | 50 |
| O-METHYLCYCLOPROPYL-DMHO | 49 | 70 |
| O-ISOPROPYL-DMHO | 27 | 80 |
| THIOETHYL-DMHO | 32 | 80 |
| O-TRIFLUOROETHYL-DMHO | 48 | 100 |
| CEPHALOTAXINE (CTX)[5] | | 2000 |
| O-C$_7$DMHO | 66 | 3 |
| O-C$_8$DMHO | 67 | 9 |
| O-AMDMHO | 69 | 29 |
| O-p-MeBNDMHO | 72 | 6 |
| O-m-MeBNDMHO | 73 | 4 |
| O-O$_5$DMHO | 74 | 24 |
| HOD$_3$ | 75 | 25 |
| HOD | 76 | 18 |
| O-MeOEDMHO | 78 | 12 |
| O-PhDMHO | 79 | 10 |
| O-BOEDMHO | 80 | 25 |
| O-NaDMHO | 81 | 8 |
| O-ThioDMHO | 82 | 5 |
| O-FuDMHO | 83 | 3 |
| O-C$_6$DDOHA | 84 | 7 |
| O-pNiBnDMHO | 85 | 18 |
| O-pMeOBNDMHO | 86 | 20 |
| HOD2 | 87 | 21 |
| O-oMeOBnDMHO | 90 | 27 |

[1] DMHO means 4'-demethyl-homoharringtonine.
[2] DMHD means 4'-demethyl-4"-hydroxydrupangtonine
[3] DMHA means 4'-demethyl-harringtonine
[4] HHT means homoharringtonine (natural or semi-synthetic source)
[5] CTX means cephalotaxines (natural source)

The same method as above was used to test the O-hexadienyl-DMHO (example 43) on K562$_{MRP}$, a subline of K562 line exhibiting a strong resistance to 50 ng/mL of homoharringtonine. The IC$_{50}$ of the O-hexadienyl-DMHO (example 43) was 16 ng/mL, i.e. a value not significantly different from homoharringtonine itself in non resistant version of K562 line (cf. above table)

What is claimed is:

1. A compound selected from the group consisting of

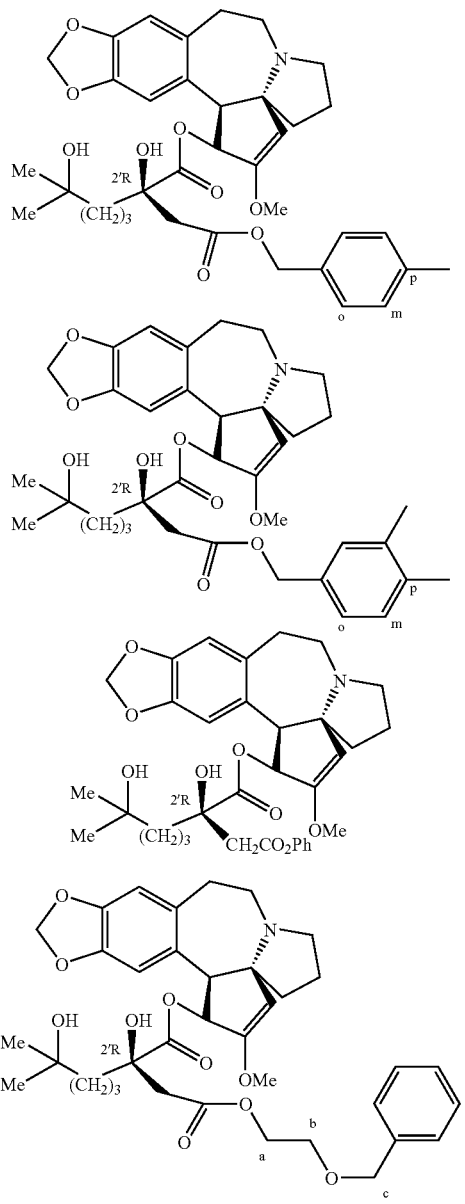

and a compound having formula (I)

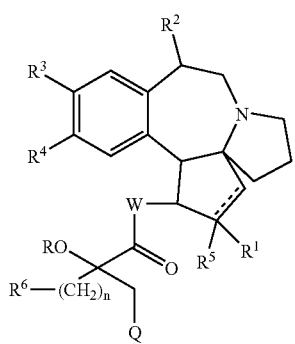

wherein
W is O or NH;
Q is COZ-$R^8$;
Z is O, S, or NH, and

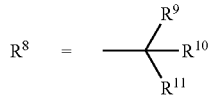

or Z-$R^8$ is $NR^{12}R^{13}$, $R^{12}$ and $R^{13}$ representing respectively $R^9$ and $R^{10}$; $R^9$, $R^{10}$ are independently H, deuterium, unbranched or branched unsubstituted $C_1$-$C_{30}$ alkyl, $C_1$-$C_{30}$ alkyl being substituted at the end of the hydrocarbonated chain by a hydroxy or alkoxy group, unsubstituted $C_3$-$C_{30}$ cycloalkyl, unsubstituted aryl, unsubstituted aryl-($C_1$-$C_{30}$)-alkyl, aryl or aryl-($C_1$-$C_{30}$) alkyl being substituted by a halogen atom, a methoxy group or a nitro group, where aryl or the aryl fragment is a mono- or poly-cyclic group, optionally containing one heteroatom selected from O, S or N, unsubstituted $C_2$-$C_{30}$ alkenyl, unsubstituted $C_2$-$C_{30}$ alkynyl, unsubstituted $C_1$-$C_{30}$ trihalogenoalkyl, unsubstituted $C_1$-$C_{30}$ alkylamino-($C_1$-$C_{30}$) alkyl, unsubstituted $C_1$-$C_{30}$ dialkylamino ($C_1$-$C_{30}$)-alkyl, or unsubstituted amino-($C_1$-$C_{30}$)-alkyl, or

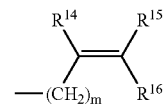

where $R^{14}$, $R^{15}$, $R^{16}$ are independently H, halogen, unsubstituted $C_1$-$C_{30}$ alkyl, unsubstituted $C_3$-$C_{30}$ cycloalkyl, unsubstituted aryl, unsubstituted aryl-($C_1$-$C_{30}$)-alkyl, unsubstituted $C_2$-$C_{30}$ alkenyl or unsubstituted $C_2$-$C_{30}$ alkynyl, unsubstituted $C_1$-$C_{30}$ trihalogenoalkyl, m is 0 to 4, and $R^{11}$ is deuterium, unbranched or branched unsubstituted $C_2$-$C_{30}$ alkyl, $C_1$-$C_{30}$ alkyl being substituted at the end of the hydrocarbonated chain by a hydroxy or alkoxy group,
unsubstituted $C_3$-$C_{30}$ cycloalkyl, unsubstituted aryl, unsubstituted aryl-($C_1$-$C_{30}$)-alkyl, aryl or aryl-($C_1$-$C_{30}$) alkyl being substituted by a halogen atom, a methoxy group or a nitro group, where aryl or the aryl fragment is a mono- or poly-cyclic group, optionally containing one heteroatorn selected from O, S or N, unsubstituted $C_2$-$C_{30}$ alkenyl, unsubstituted $C_2$-$C_{30}$ alkynyl, unsubstituted $C_1$-$C_{30}$ trihalogenoalkyl, unsubstituted $C_1$-$C_{30}$ alkylamino-($C_1$-$C_{30}$) alkyl, unsubstituted $C_1$-$C_{30}$ dialkylamino ($C_1$-$C_{30}$)-alkyl, or unsubstituted amino-($C_1$-$C_{30}$)-alkyl, or

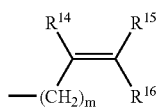

where $R^{14}, R^{15}, R^{16}$ are independently H, halogen, unsubstituted $C_1$-$C_{30}$ alkyl, unsubstituted $C_3$-$C_{30}$ cycloalkyl, unsubstituted aryl, unsubstituted aryl-($C_1$-$C_{30}$)-alkyl, unsubstituted $C_2$-$C_{30}$ alkenyl or unsubstituted $C_2$-$C_{30}$ alkynyl, unsubstituted $C_1$-$C_{30}$ trihalogenoalkyl, m is 0 to 4, and wherein $R^1$ may be $CH_3$ when Z represents S or NH; $R^1$ is H, OH, OMe, unsubstituted O—($C_1$-$C_{30}$)-alkyl, unsubstituted O-aryl-($C_1$-$C_{30}$)-alkyl, unsubstituted O—($C_2$-$C_{30}$)-alkenyl, unsubstituted O—($C_3$-$C_{30}$)-cycloalkyl or null, and $R^2$ is H or OH, or $R^1$, $R^2$ together form —O—; $R^3$ and $R^4$ are OMe, or $R^3$ and $R^4$ together form —OCH$_2$O—; R is H, unsubstituted $C_1$-$C_{30}$ alkyl or O-protecting group, and $R^6$ is —(C—Y)Me$_2$, —CH═CMe$_2$, or an unsubstituted aryl group or R and $R^6$ together form —CMe$_2$-, Y is H, OH or halogen;

n=0 to 8;

$R^5$ is H, OH, OMe, unsubstituted O—($C_1$-$C_{30}$)-alkyl, unsubstituted O-aryl-($C_1$-$C_{30}$)-alkyl, unsubstituted O—($C_2$-$C_{30}$)-alkenyl, unsubstituted O—($C_3$-$C_{30}$)-cycloalkyl or unsubstituted O-aryl; and the dotted line is null or forms a double bond depending on the meaning of $R^1$.

2. A compound of formula (I) according to claim 1, wherein the dotted line forms a double bond, $R^1$ is null, $R^2$ is H, $R^3$ and $R^4$ together form —O—CH$_2$—O—, and $R^5$ is OMe.

3. A compound of formula (I) according to claim 1, wherein the dotted line is null, $R^1$ and $R^2$ represent —O—, $R^3$ and $R^4$ together form —O—CH$_2$—O—, and $R^5$ is OMe.

4. A compound of formula (I) according to claim 2, wherein n=1 to 3.

5. A compound of formula (I) according to claim 1, wherein W is O.

6. A compound according to claim 1 selected from the group consisting of the following compounds 66 to 90:

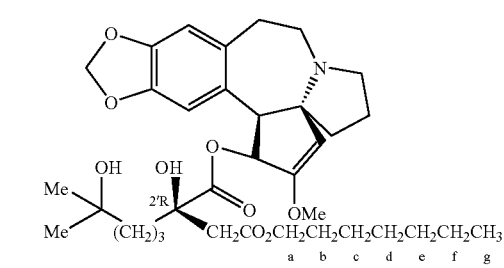

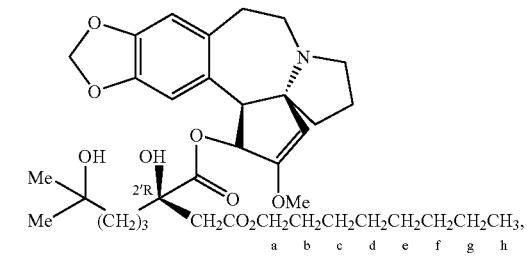

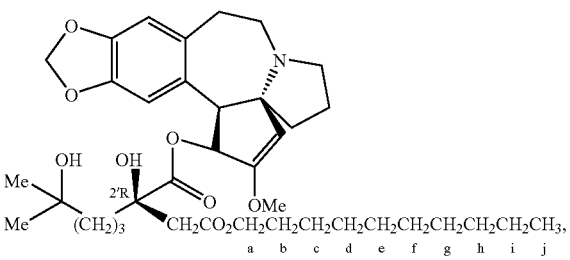

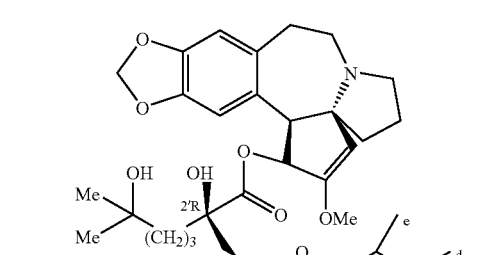

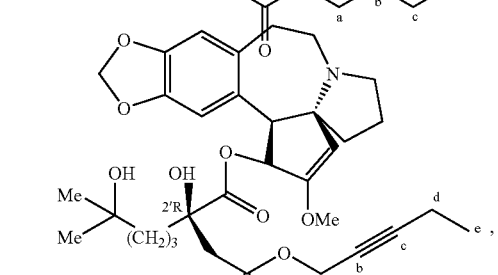

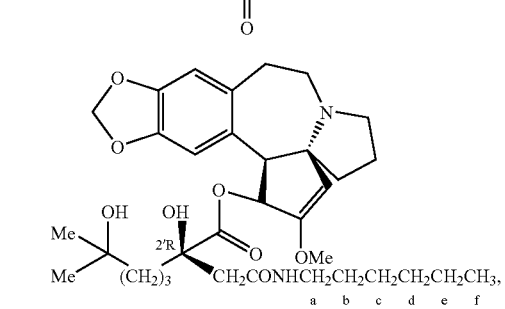

-continued

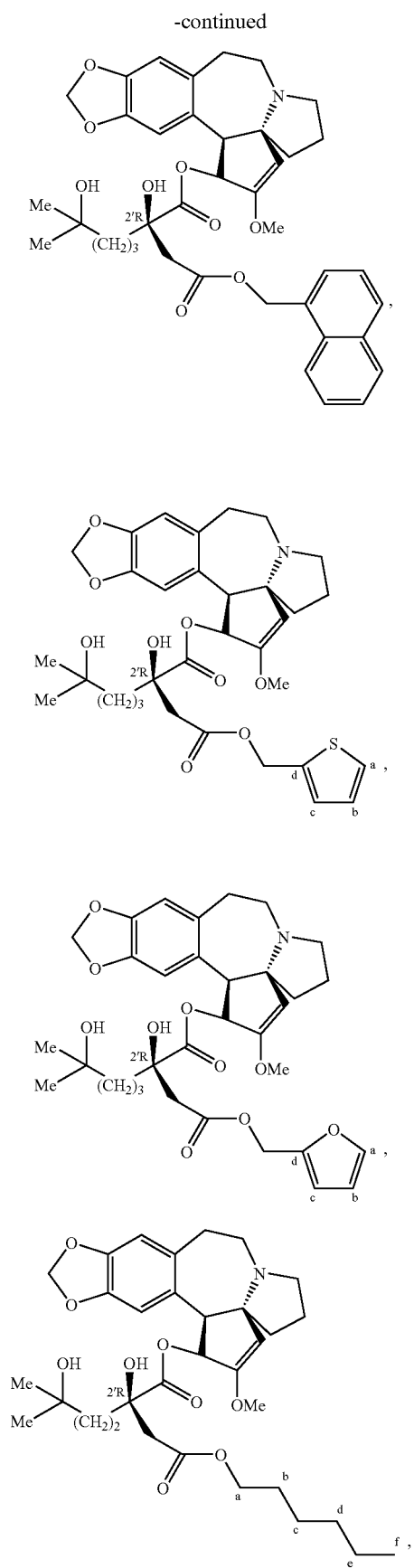
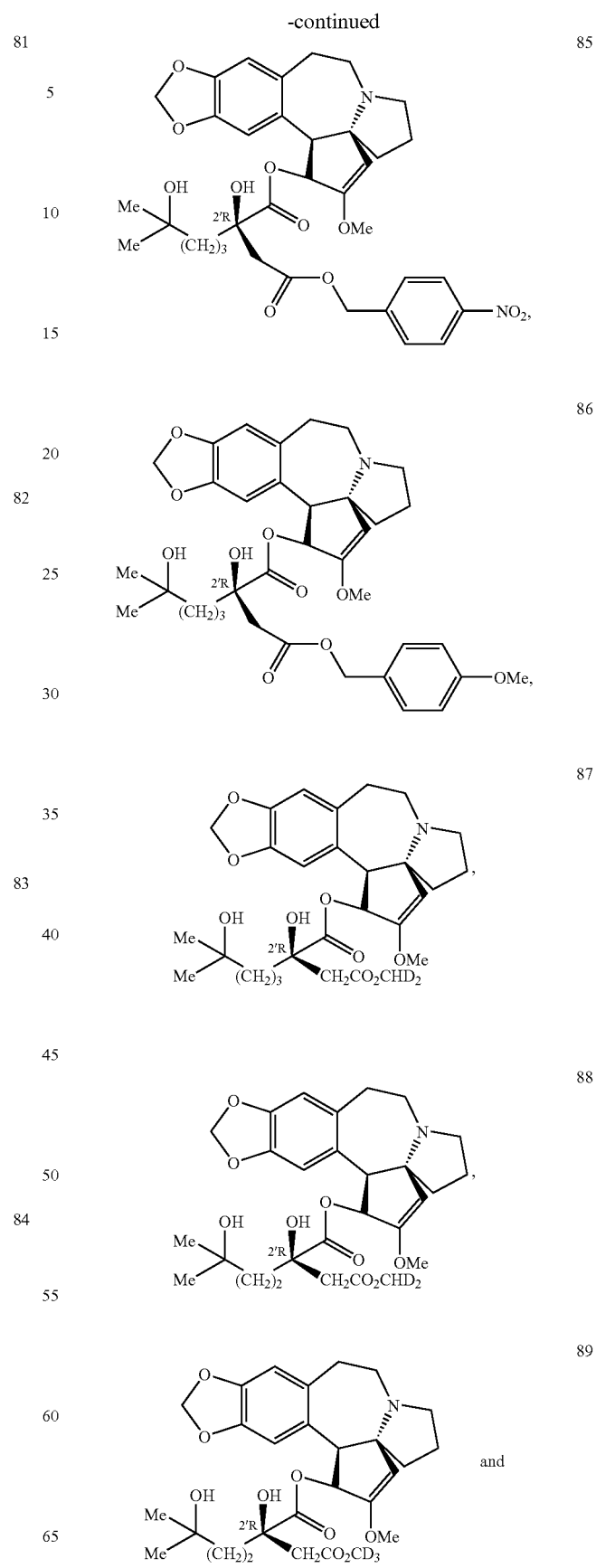

-continued

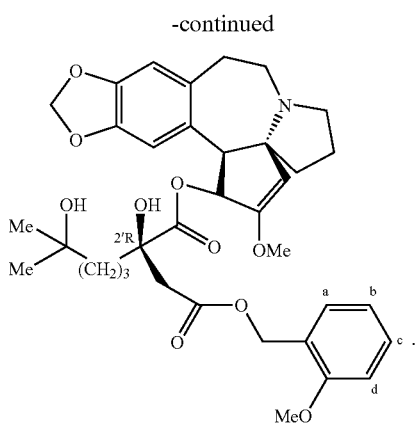
(90)

7. A process for preparing a compound of formula (I) according to claim 1, wherein W represents O, said process comprising the following steps i) and ii):
i) hydrolyzing selectively the compound of formula (II)

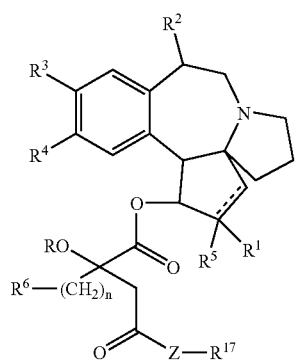
(II)

wherein
R$^1$ is H, OH, OMe, unsubstituted O—(C$_1$-C$_{30}$)-alkyl, unsubstituted O-aryl-(C$_1$-C$_{30}$)-alkyl, unsubstituted O—(C$_2$-C$_{30}$)-alkenyl, unsubstituted O—(C$_3$-C$_{30}$)-cycloalkyl or null and, R$^2$ is H or OH, or R$^1$ and R$^2$ together form —O—;
R$^3$ and R$^4$ are OMe, or R$^3$ and R$^4$ together form —OCH$_2$O—;
R is H, unsubstituted C$_1$-C$_{30}$-alkyl or O-protecting group, and
R$^6$ is —(C—Y)Me$_2$, —CH=CMe$_2$, or an unsubstituted aryl group;
or R and R$^6$ together form —CMe$_2$—;
Y is H, OH or halogen;
n=0 to 8;
R$^5$ is H, OH, OMe, unsubstituted O—(C$_1$-C$_{30}$)-alkyl, unsubstituted O-aryl-(C$_1$-C$_{30}$)-alkyl, unsubstituted O—(C$_2$-C$_{30}$)-alkenyl, unsubstituted O—(C$_3$-C$_{30}$)-cycloalkyl or unsubstituted O-aryl;
the dotted line is null or forms a double bond depending on the meaning of R$^1$;
Z is O or S; and
R$^{17}$ is unsubstituted C$_1$-C$_{30}$-alkyl, unsubstituted C$_2$-C$_{30}$-alkenyl, unsubstituted C$_3$-C$_{30}$-cycloalkyl, unsubstituted C$_2$-C$_{30}$-alkynyl, unsubstituted aryl-(C$_1$-C$_{30}$)-alkyl or unsubstituted aryl, with an agent in hydro-organic solvent mixture to give as reaction product, amphoteric acid of formula (III)

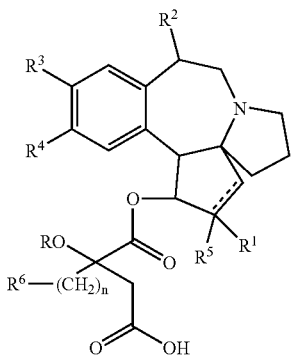
(III)

wherein R$^1$ to R$^5$, R and R$^6$ are defined as above,
ii) performing the esterification of the above obtained amphoteric acid of formula (III) with an esterification agent and a compound of formula R$^8$-ZH,
and wherein the steps (i) and ii) are carried out successively or simultaneously.

8. The process according to claim 7, wherein the esterification agent is a lewis acid or protonic acid.

9. The process according to claim 7, wherein the amphoteric acid of formula (III) is activated with an imide or by formation of a mixed anhydride or an acid chloride.

10. The process according to claim 9, wherein the imide is dicyclohexylcarbodiimide of diisopropylcarbodiimide.

11. The process according to claim 9, wherein the mixed anhydride is formed with 2,3,6-trichlorobenzoic acid by contact with 2,4,6-trichlorobenzoyl chloride in the presence of a base.

12. The process according to claim 7, wherein the steps i) and ii) are carried out simultaneously, without isolation of the amphoteric acid of formula (III), via a reaction of transesterification performed in the presence of an acidic or basic catalyst.

13. The process according to claim 12, wherein the catalyst is a base.

14. The process according to claim 12, wherein the catalyst is a lewis acid or a protonic acid.

15. The process according to claim 7, wherein Z is O and R$^{17}$ is methyl.

16. The process according to claim 13, wherein the catalyst is an alkaline hydride.

17. A pharmaceutical composition which comprises a therapeutically effective amount of at least one compound according to claim 1 associated with one or more pharmaceutically acceptable carriers.

18. A method for inhibiting mammalian parasites, which comprises administering to a mammal in need of such a treatment a therapeutically effective amount of at least one compound of claim 1.

19. A method for treating leukemia which comprises administering to a mammal in need of such treatment a therapeutically effective amount of at least one compound of claim 1.

* * * * *

UNITED STATES PATENT AND TRADEMARK OFFICE
CERTIFICATE OF CORRECTION

PATENT NO.      : 7,285,546 B2
APPLICATION NO. : 10/403506
DATED           : October 23, 2007
INVENTOR(S)     : Jean-Pierre Robin et al.

It is certified that error appears in the above-identified patent and that said Letters Patent is hereby corrected as shown below:

Column 3, lines 33 and 34, change "t-butyidiphenylsilyl" to --t-butyldiphenylsilyl--.

Column 99, claim 1, formula 73 is incorrect and should be replaced with the following formula 73:

-- 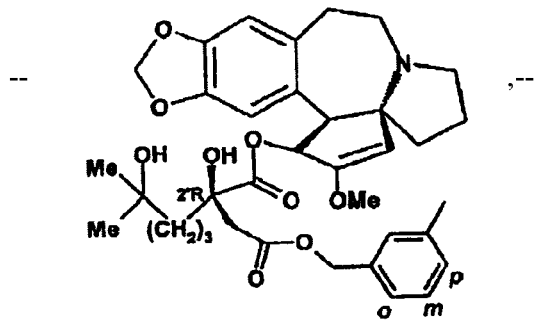 ,--

73

Column 101, claim 1, line 20, change "$R^1$ may be $CH_3$" to --$R^{11}$ may be $CH_3$--.

Column 102, claim 6, please separate formula 70 and formula 71.

UNITED STATES PATENT AND TRADEMARK OFFICE
CERTIFICATE OF CORRECTION

PATENT NO.       : 7,285,546 B2
APPLICATION NO.  : 10/403506
DATED            : October 23, 2007
INVENTOR(S)      : Jean-Pierre Robin et al.

It is certified that error appears in the above-identified patent and that said Letters Patent is hereby corrected as shown below:

Column 105, claim 6, formula 84 is incorrect and should be replaced with the following formula 84:

-- 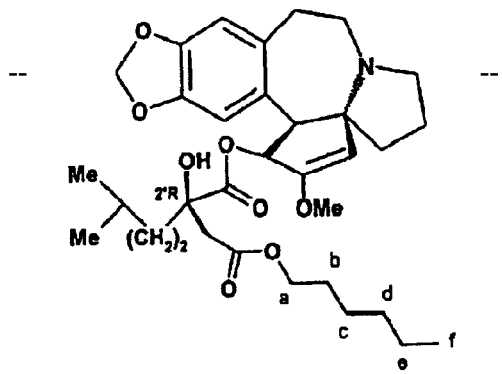 --

84

Signed and Sealed this

Twenty-seventh Day of May, 2008

JON W. DUDAS
*Director of the United States Patent and Trademark Office*